US012077810B2

(12) United States Patent
Thomann et al.

(10) Patent No.: US 12,077,810 B2
(45) Date of Patent: Sep. 3, 2024

(54) METHODS AND SYSTEMS FOR AMPLIFICATION IN COMPLEX SAMPLES

(71) Applicant: T2 Biosystems, Inc., Lexington, MA (US)

(72) Inventors: Ulrich Hans Thomann, Stow, MA (US); Jessica Lee Snyder, Arlington, MA (US); Thomas Jay Lowery, Jr., Belmont, MA (US)

(73) Assignee: T2 Biosystems, Inc., Lexington, MA (US)

( * ) Notice: Subject to any disclaimer, the term of this patent is extended or adjusted under 35 U.S.C. 154(b) by 1330 days.

(21) Appl. No.: 16/093,488

(22) PCT Filed: Apr. 12, 2017

(86) PCT No.: PCT/US2017/027210
§ 371 (c)(1),
(2) Date: Oct. 12, 2018

(87) PCT Pub. No.: WO2017/180745
PCT Pub. Date: Oct. 19, 2017

(65) Prior Publication Data
US 2021/0002715 A1 Jan. 7, 2021

Related U.S. Application Data

(60) Provisional application No. 62/322,551, filed on Apr. 14, 2016.

(51) Int. Cl.
*C12Q 1/6848* (2018.01)
*C12P 19/34* (2006.01)
*C12Q 1/6806* (2018.01)
*C12Q 1/6825* (2018.01)
*G16B 30/00* (2019.01)
*G16B 30/10* (2019.01)

(52) U.S. Cl.
CPC .......... *C12Q 1/6848* (2013.01); *C12P 19/34* (2013.01); *C12Q 1/6806* (2013.01); *C12Q 1/6825* (2013.01); *G16B 30/00* (2019.02); *G16B 30/10* (2019.02)

(58) Field of Classification Search
CPC .. C12Q 1/6848; C12Q 1/6806; C12Q 1/6825; C12Q 2521/101; C12Q 2527/119; C12Q 2527/149; C12Q 2531/113; C12P 19/34; G16B 30/00; G16B 30/10
See application file for complete search history.

(56) References Cited

U.S. PATENT DOCUMENTS

| | | | |
|---|---|---|---|
| 4,965,188 A | 10/1990 | Mullis et al. | |
| 5,702,884 A * | 12/1997 | Ekeze | G01N 33/5094 435/5 |
| 8,409,807 B2 | 4/2013 | Neely et al. | |
| 8,563,298 B2 | 10/2013 | Lowery, Jr. et al. | |
| 8,883,423 B2 | 11/2014 | Neely | |
| 9,046,493 B2 | 6/2015 | Neely et al. | |
| 9,360,457 B2 | 6/2016 | Neely et al. | |
| 9,488,648 B2 | 11/2016 | Neely et al. | |
| 9,702,852 B2 | 7/2017 | Lowery, Jr. et al. | |
| 9,714,940 B2 | 7/2017 | Lowery, Jr. et al. | |
| 2002/0115077 A1 | 8/2002 | Einsele | |
| 2009/0155777 A1 | 6/2009 | Yang et al. | |
| 2009/0286251 A1 | 11/2009 | Xu | |
| 2011/0294128 A1 | 12/2011 | Peytavi et al. | |
| 2013/0029345 A1 | 1/2013 | Neely et al. | |
| 2013/0171615 A1 | 7/2013 | Van Meerbergen et al. | |
| 2013/0260367 A1 | 10/2013 | Lowery, Jr. et al. | |
| 2013/0273522 A1 | 10/2013 | Lowery, Jr. et al. | |
| 2013/0273523 A1 | 10/2013 | Neely et al. | |
| 2013/0280708 A1 | 10/2013 | Neely | |
| 2014/0106442 A1 | 4/2014 | Lowery, Jr. et al. | |
| 2014/0295419 A1 | 10/2014 | Zhang et al. | |
| 2015/0354015 A1 | 12/2015 | Chang et al. | |
| 2017/0233798 A1 | 8/2017 | Neely et al. | |
| 2019/0085381 A1 | 3/2019 | Neely et al. | |

FOREIGN PATENT DOCUMENTS

| | | | |
|---|---|---|---|
| CN | 102286473 | * | 12/2011 |
| EP | 0751226 A2 | | 1/1997 |
| EP | 2261371 A2 | | 12/2010 |
| JP | 2014-505233 A | | 2/2014 |
| WO | WO-2002/036813 A2 | | 5/2002 |
| WO | WO-2003/064605 A2 | | 8/2003 |
| WO | WO-2012/054638 A2 | | 4/2012 |
| WO | WO-2012/054639 A2 | | 4/2012 |
| WO | WO-2013/068107 A1 | | 5/2013 |
| WO | WO-2013/158281 A1 | | 10/2013 |
| WO | WO-2014/072366 A1 | | 5/2014 |
| WO | WO-2017/127731 A1 | | 7/2017 |

OTHER PUBLICATIONS

Wang, Kit and method for directly amplifying nucleic acid in whole blood sample, 2011, English translation of CN 1022864473, published Dec. 21, 2011, pp. 1-9 (Year: 2011).*
Arai et al., "DNA Diagnosis of Ovale Malaria and Malariae Malaria Using Microtiter Plate-Hybridization," Nucleosides & Nucleotides. 13(6-7): 1363-1374 (1994).
Bu et al., "Direct Polymerase Chain Reaction (PCR) From Human Whole Blood and Filter-Paper-Dried Blood by Using a PCR Buffer With a Higher pH," Anal Biochem. 375(2):370-2 (2008).
Extended European Search Report for European Patent Application No. 17783057.7, dated Feb. 10, 2020 (19 pages).
Mercier et al., "Direct PCR From Whole Blood, Without DNA Extraction," Nucleic Acids Res 18(19):5908 (1990).
International Preliminary Report on Patentability for International Application No. PCT/US17/27210, mailed Oct. 25, 2018 (8 pages).

(Continued)

*Primary Examiner* — Narayan K Bhat
(74) *Attorney, Agent, or Firm* — Clark & Elbing LLP

(57) ABSTRACT

The invention features methods, systems, and cartridges for amplification of target nucleic acids in complex samples, for example, whole blood. The invention also features diagnostic and therapeutic methods based on amplification of target nucleic acids characteristic of pathogens present in complex samples containing cells and/or cell debris, for example, whole blood.

14 Claims, 11 Drawing Sheets

(56) References Cited

OTHER PUBLICATIONS

International Search Report and Written Opinion for International Application No. PCT/US17/27210, mailed Jul. 18, 2017 (14 pages).
Communication pursuant to Rule 164(1) EPC for European Application No. 17783057.7, dated Oct. 11, 2019 (16 pages).
Kermekchiev et al., "Mutants of Taq DNA polymerase resistant to PCR inhibitors allow DNA amplification from whole blood and crude soil samples," Nucleic Acids Res. 37(5):e40 (2009) (14 pages).
Tirasophon et al., "A novel detection of a single Plasmodium falciparum in infected blood," Biochem Biophys Res Commun. 175(1):179-84 (1991) (6 pages).
Notice of Reasons for Rejection for Japanese Patent Application No. 2018-553927, dated Mar. 30, 2021 (14 pages).
"Polymerase-Kettenreaktion" Spektrum Encyclopedia of Biology. retrieved from <https://www.spektrum.de/lexikon/biologie/polymerase-kettenreaktion/52909> (1999) (16 pages).
"User Guide for GoldBio Buffers," GioldBio, created Aug. 24, 2015 (66 pages).
Bagasra et al., "Detection of human immunodeficiency virus type 1 provirus in mononuclear cells by in situ polymerase chain reaction," N Engl J Med. 326(21):1385-91 (1992).
Burckhardt, "Amplification of DNA from Whole Blood," PCR Methods Appl. 3(4):239-43 (1994).
Certified U.S. Appl. No. 62/281,608, filed Jan. 11, 2017 (165 Pages).
Communication of Notices of Opposition Pursuant to Rule 79(1) EPC for European Patent Application No. 17783057.7 dated May 31, 2023 (2 pages).
Notice of opposition to a European Patent for European Application No. 17783057.7, dated May 16, 2023 (45 pages).
Notice of opposition to a European Patent for European Application No. 17783057.7, dated May 17, 2023 (55 pages).
Data Sheet, "Thermoscript™ RT-PCR System," Invitrogen. Jan. 2013 (4 pages).
Data Sheet: BD Vacutainer Tube Guide. Retrieved from <https://www.bd.com/resource.aspx?IDX=11068> (2009) (8 pages).
Erlich et al., "Recent Advances in the Polymerase Chain Reaction," Science. 252(5013):1643-51 (1991).
Extract of the European Patent Register for European Patent Application No. EP3405479, accessed May 4, 2023 <https://register,epo.org/application?number=EP17742048&lng=fr&tab=main> (4 pages).
Fabre et al., "High DNA stability in white blood cells and buffy coat lysates stored at ambient temperature under anoxic and anhydrous atmosphere," PLoS One. 12(11):e0188547 (Nov. 2017) (23 pages).
Gupta, "The Mechanism of Cryohemolysis: By Direct Observation with Cryomicroscope and the Electron Microscope," Cryobiology. 12(4):417-26 (1975).

Hill et al., "The Polymerase Chain Reaction in Molecular and Micro-biology," Biotechnol Genet Eng Rev. 10:343-77 (1992).
Instruction Manual, "Polymerases & Amplification," Taq PCR Kit, New England BioLabs Inc. NEB #E5000S, Version 1.4, Jul. 2011 (11 pages).
Kebelmann-Betzing et al., "Advantages of a New Taq DNA Polymerase in Multiplex PCR and Time-Release PCR," Biotechniques. 24(1):154-8 (1998).
Kim et al., "Application of Hot Start PCR Method in PCR-based Preimplantation Genetic Diagnosis," J Genet Med. 9(1):11-16 (2012).
Le et al., "An optimised direct lysis method for gene expression studies on low cell numbers," Sci Rep. 5:12859 (2015) (10 pages).
Lippi et al., "Influence of temperature and period of freezing on the generation of hemolysate and blood cell lysate," Clin Biochem. 44(14-15):1267-9 (2011).
Lorenz, "Polymerase Chain Reaction: Basic Protocol Plus Troubleshooting and Optimization Strategies," J of Visl Exper. 63:e3998 (2012) (15 pages).
Neely et al., "T2 Magnetic Resonance Enables Nanoparticle-Mediated Rapid Detection of Candidemia in Whole Blood," Sci Transl Med. 5(182):182ra54 (2013) (8 pages).
Nordvåg et al., "Direct PCR of washed blood cells," biotechniques. 12(4):490-3 (1992).
Nuovo et al., "An Improved Techique for the In Situ Detection of DNA After Polymerase Chain Reaction Amplification," Am J Pathol. 139(6):1239-44 (1991).
Nuovo et al., "Detection of Human Papillomavirus DNA in Formalin-fixed Tissues by In Situ Hybridization After Amplification by Polymerase Chain Reaction," Am J Pathol. 139(4):847-54 (1991).
Nuovo et al., "Importance of Different Variables for Enhancing In Situ Detection of PCR-amplified DNA," PCR Methods Appl. 2(4):305-12 (1993).
Product information AmpliTaq Gold®, Applied Biosystems, Dec. 7, 2000 (16 pages).
Van Pelt-Verkuil et al., "Principles and Technical Aspects of PCR Amplification," Chapters 1, 3.1.2, 6.3, and 7. Springer Science + Business Media B.V. (2008) (41 pages).
Wataya et al., "DNA diagnosis of falciparum malaria using a double PCR technique: a field trial in the Solomon Islands," Mol Biochem Parasitol 58(1):165-8 (1993) (3 pages).
Declaration of J. Snyder for European Patent No. 3443124 dated Dec. 8, 2023 (5 pages).
Response to Notices of Opposition dated Dec. 11, 2023 for European Patent Application No. 17783057.7 (113 pages).
Summons to oral proceedings dated Feb. 29, 2024 for European Patent Application No. 17783057.7 (12 pages).
Response to summons to attend oral proceedings for European Patent Application No. 17783057.7, dated Jul. 19, 2024 (16 pages).

* cited by examiner

METHODS AND SYSTEMS FOR AMPLIFICATION IN COMPLEX SAMPLES

FIELD OF THE INVENTION

The invention features methods and systems for amplification of target nucleic acids (e.g., DNA) in complex samples containing cells and/or cell debris, for example, blood samples (e.g., whole blood).

BACKGROUND OF THE INVENTION

Complex samples containing cells and/or cell debris (e.g., blood) contain interfering substances that can sometimes inhibit amplification methods (e.g., polymerase chain reaction (PCR)), which impedes direct detection of nucleic acid-based targets, whether from mammalian cells or from pathogens. This inhibition is especially problematic when specific loci must be amplified that are present only at minute concentrations, such as from one to ten microbial cells contained in a milliliter of human blood, which may be the case with pathogens that are present at low titer. For example, various heme compounds found in blood, including hemoglobin and hematin, have been shown to be inhibitory to Taq polymerase when added into PCR reactions. However, simply removing sources of heme compounds is not sufficient, as blood fractions lacking hemoglobin were also found to be inhibitory due to the presence of immunoglobulin G (IgG).

Another challenge in amplification of target nucleic acids from pathogens present in complex samples containing host cells and/or cell debris is presented by the enormous amount of mammalian DNA that is contained within the sample. For example, one milliliter of human blood contains approximately 3 to 6 million white blood cells. Since one human cell contains approximately 6 pg of nuclear DNA, 18 to 36 μg of human DNA is contained in one milliliter of crude blood lysate. In contrast, 10 bacterial cells contain 33 fg of DNA (based on a 2 Mbase genome). Thus, an approximate 8.4 billion-fold excess of human DNA over the microbial DNA of interest can exist. The inhibitory effects of high DNA concentrations in diagnostic assays aimed to detect pathogenic targets in total DNA extracted and purified from human blood is known in the art.

To reduce inhibition by interfering substances or high concentrations of non-target (e.g., host) nucleic acids, current assays for detecting pathogens in complex samples typically rely on nucleic acid isolation and fractionation/enrichment. Nucleic acid isolation is time-consuming, and loss of nucleic acids that are present in low copy numbers, such as microbial target DNA, may be lost during the process. Attempts at purifying the intact pathogen prior to nucleic acid isolation can also result in significant loss of target and reduced assay sensitivity. Another aspect of a lengthy purification process involving consumables and reagents is the danger of contamination with environmental and commensal microbial species. Therefore, minimal processing of complex samples before amplification and detection assays is desirable, and in some cases even necessary to achieve the highest levels of sensitivity and specificity.

Thus, there remains a need in the art for improved methods of amplifying target nucleic acids directly in complex samples containing cells and/or cell debris, preferably using existing commercially available enzymes such as thermostable DNA polymerases.

SUMMARY OF THE INVENTION

The invention features methods, panels, and systems for amplifying target nucleic acids in complex samples.

In one aspect, the invention features a method for amplifying a target nucleic acid in a biological sample obtained from a subject, wherein the biological sample includes subject-derived cells or cell debris, the method including: (a) lysing the cells in the biological sample to form a lysate; (b) adding to the lysate a buffer solution including a buffering agent to form a reaction mixture, wherein the buffer solution has a moderately alkaline pH at ambient temperature; (c) following step (b), heating the reaction mixture to form a denatured reaction mixture; (d) adding a thermostable nucleic acid polymerase to the denatured reaction mixture; and (e) amplifying the target nucleic acid to form an amplified solution including an amplicon. In some embodiments, the final concentration of the thermostable nucleic acid polymerase in step (d) is at least about 0.02 units per microliter of the denatured reaction mixture. In some embodiments, step (d) includes adding to the denatured reaction mixture at least about $2.4 \times 10^{-5}$ micrograms of a thermostable nucleic acid polymerase per microliter of denatured reaction mixture. In some embodiments, the biological sample is about 0.2 mL to about 5 mL (e.g., about 0.2 mL, about 0.4 mL, about 0.6 mL, about 0.8 mL, about 1 mL, about 1.5 mL, about 2 mL, about 2.5 mL, about 3 mL, about 3.5 mL, about 4 mL, about 4.5 mL, or about 5 mL). In some embodiments, the biological sample is about 0.9 mL. In some embodiments, the biological sample is selected from the group consisting of blood, bloody fluids, tissue samples, and sputum. In some embodiments, the blood is whole blood, a crude blood lysate, serum, or plasma. In some embodiments, the bloody fluid is wound exudate, phlegm, or bile. In some embodiments, the tissue sample is a tissue biopsy. In some embodiments, the tissue biopsy is a skin biopsy, muscle biopsy, or lymph node biopsy. In some embodiments, the tissue sample is a homogenized tissue sample.

In another aspect, the invention features a method for amplifying a target nucleic acid in a whole blood sample, the method including: (a) providing a crude blood lysate produced by lysing the red blood cells in a whole blood sample from a subject, centrifuging the sample to form a supernatant and a pellet including cells, discarding some or all of the supernatant, optionally washing the pellet, and lysing the cells in the pellet; (b) adding to the crude blood lysate a buffer solution including a buffering agent to form a reaction mixture, wherein the buffer solution has a moderately alkaline pH at ambient temperature; (c) following step (b), heating the reaction mixture to form a denatured reaction mixture; (d) adding a thermostable nucleic acid polymerase to the denatured reaction mixture, wherein the final concentration of the thermostable nucleic acid polymerase is at least about 0.02 units per microliter of the denatured reaction mixture; and (e) amplifying the target nucleic acid to form an amplified solution including an amplicon.

In another aspect, the invention features a method for amplifying a target nucleic acid in a whole blood sample, the method including: (a) providing a crude blood lysate produced by lysing the red blood cells in a whole blood sample from a subject, centrifuging the sample to form a supernatant and a pellet including cells, discarding some or all of the supernatant, optionally washing the pellet, and lysing the cells in the pellet; (b) adding to the crude blood lysate a buffer solution including a buffering agent to form a reaction mixture, wherein the buffer solution has a moderately alkaline pH at ambient temperature; (c) following step (b), heating the reaction mixture to form a denatured reaction mixture; (d) adding to the denatured reaction mixture at least about $2.4 \times 10^{-5}$ micrograms of a thermostable nucleic acid polymerase per microliter of denatured reaction mixture; and (e) amplifying the target nucleic acid to form an amplified solution including an amplicon.

In some embodiments of any of the preceding aspects, step (c) further includes centrifuging the denatured reaction mixture prior to step (d). In some embodiments of any of the preceding aspects, the method includes adding (i) deoxynucleotide triphosphates (dNTPs), (ii) magnesium, (iii) a forward primer, and/or (iv) a reverse primer during step (b) or during step (d). In some embodiments of any of the preceding aspects, the whole blood sample is about 0.2 mL to about 5 mL (e.g., about 0.2 mL, about 0.4 mL, about 0.6 mL, about 0.8 mL, about 1 mL, about 1.5 mL, about 2 mL, about 2.5 mL, about 3 mL, about 3.5 mL, about 4 mL, about 4.5 mL, or about 5 mL). In some embodiments of any of the preceding aspects, the whole blood sample is about 0.9 mL. In some embodiments of any of the preceding aspects, the crude blood lysate produced from the whole blood sample has a volume of about 10 µL to about 500 µL (e.g., about 10 µL, about 25 µL, about 50 µL, about 75 µL, about 100 µL, about 125 µL, about 150 µL, about 175 µL, about 200 µL, about 225 µL, about 250 µL, about 275 µL, about 300 µL, about 325 µL, about 350 µL, about 375 µL, about 400 µL, about 425 µL, about 450 µL, about 475 µL, or about 500 µL). In some embodiments, the crude blood lysate produced from the whole blood sample has a volume of about 25 µL to about 200 µL. In some embodiments of any of the preceding aspects, the crude blood lysate produced from the whole blood sample has a volume of about 50 µL. In some embodiments, the reaction mixture of step (b) contains about 1% to about 70% (e.g., about 1%, about 5%, about 10%, about 15%, about 20%, about 25%, about 30%, about 35%, about 40%, about 45%, about 50%, about 55%, about 60%, about 65%, or about 70%) crude blood lysate. In some embodiments, the reaction mixture of step (b) contains about 50% crude blood lysate.

In another aspect, the invention features a method for amplifying a target nucleic acid in a sample including unprocessed whole blood, the method including: (a) providing a mixture including a buffer solution including a buffering agent, dNTPs, magnesium, a forward primer, a reverse primer, and a thermostable nucleic acid polymerase, wherein the buffer solution has a moderately alkaline pH at ambient temperature, and wherein the final concentration of the thermostable nucleic acid polymerase is at least about 0.02 units per microliter of the mixture; (b) adding to the mixture a portion of a whole blood sample obtained from a subject to form a reaction mixture; and (c) amplifying the target nucleic acid to form an amplified solution including an amplicon. In some embodiments, the reaction mixture contains from about 1% to about 50% (e.g., about 1%, about 5%, about 10%, about 15%, about 20%, about 25%, about 30%, about 35%, about 40%, about 45%, or about 50%) (v/v) whole blood. In some embodiments, the reaction mixture contains about 30% to about 40% (v/v) whole blood.

In another aspect, the invention features a method for amplifying a target nucleic acid in a sample including whole blood, the method including: (a) providing a mixture including a buffer solution including a buffering agent, dNTPs, magnesium, a forward primer, a reverse primer, and a thermostable nucleic acid polymerase, wherein the buffer solution has a moderately alkaline pH at ambient temperature, and wherein the mixture contains at least about $2.4 \times 10^{-5}$ micrograms of the thermostable nucleic acid polymerase per microliter of the mixture; (b) adding to the mixture a portion of a whole blood sample obtained from a subject to form a reaction mixture; and (c) amplifying the target nucleic acid to form an amplified solution including an amplicon. In some embodiments, the reaction mixture contains from about 1% to about 50% (e.g., about 1%, about 5%, about 10%, about 15%, about 20%, about 25%, about 30%, about 35%, about 40%, about 45%, or about 50%) (v/v) whole blood. In some embodiments, the reaction mixture contains about 30% to about 40% (v/v) whole blood.

In some embodiments of any of the preceding aspects, the moderately alkaline pH at ambient temperature is from about pH 7.1 to about pH 10.5 (e.g., about pH 7.1, about pH 7.5, about pH 8.0, about pH 8.5, about pH 9, about pH 9.5, about pH 10, or about pH 10.5). In some embodiments, the moderately alkaline pH at ambient temperature is from about pH 7.5 to about pH 9.5. In some embodiments, the moderately alkaline pH at ambient temperature is from about pH 8 to about pH 9. In some embodiments, the moderately alkaline pH at ambient temperature is about pH 8.7.

In some embodiments of any of the preceding aspects, the pH of the buffer solution remains approximately at or above a neutral pH at 95° C. In some embodiments, the pH of the buffer solution is about 6.5 to about 9.0 (e.g., about 6.5, about 7.0, about 7.5, about 8.0, about 8.5, or about 9.0) at 95° C. In some embodiments, the pH of the buffer solution is about 7.0 to about 8.5 at 95° C. In some embodiments, the pH of the buffer solution is about 7.0 to about 7.5 at 95° C. In some embodiments, the pH of the buffer solution is about 7.2 at 95° C.

In some embodiments of any of the preceding aspects, the final concentration of the thermostable nucleic acid polymerase ranges from about 0.02 to about 0.8 units/µL (e.g., about 0.02, about 0.04, about 0.06, about 0.08, about 0.1, about 0.15, about 0.2, about 0.25, about 0.3, about 0.35, about 0.4, about 0.45, about 0.5, about 0.55, about 0.6, about 0.65, about 0.7, about 0.75, or about 0.8 units/µL). In some embodiments, the final concentration of the thermostable nucleic acid polymerase ranges from about 0.125 to about 0.5 units/µL. In some embodiments, the final concentration of the thermostable nucleic acid ranges from about 0.125 to about 0.25 units/µL.

In some embodiments of any of the preceding aspects, the final concentration of thermostable nucleic acid polymerase is from about $2.4 \times 10^{-5}$ micrograms to about 0.01 micrograms per microliter (e.g., about $2.4 \times 10^{-5}$, about $5 \times 10^{-5}$, about $7.5 \times 10^{-5}$, about $1 \times 10^{-4}$, about $2.5 \times 10^{-4}$, about $5 \times 10^{-4}$, about $7.5 \times 10^{-4}$, about $1 \times 10^{-3}$, about $2.5 \times 10^{-3}$, about $5 \times 10^{-3}$, about $7.5 \times 10^{-3}$, or about 0.01 micrograms per microliter) of denatured reaction mixture or reaction mixture. In some embodiments, the final concentration of thermostable nucleic acid polymerase is from about $2.4 \times 10^{-5}$ micrograms to about 0.001 micrograms per microliter of denatured reaction mixture or reaction mixture. In some embodiments, the final concentration of thermostable nucleic acid polymerase is from about $2.4 \times 10^{-5}$ micrograms to about 0.0001 micrograms per microliter of denatured reaction mixture or reaction mixture.

In some embodiments of any of the preceding aspects, the thermostable nucleic acid polymerase is a thermostable DNA polymerase. In some embodiments, the thermostable DNA polymerase is a wild-type thermostable DNA polymerase or a mutant thermostable DNA polymerase. In some embodiments, the wild-type thermostable DNA polymerase is *Thermus aquaticus* (Taq) DNA polymerase, *Thermus thermophilus* (Tth) DNA polymerase, *Thermus filiformis* (Tfi) DNA polymerase, *Thermus flavus* (Tfl) DNA polymerase, *Thermatoga maritima* (Tma) DNA polymerase, *Thermus* spp. Z05 DNA polymerase, or an archael polymerase. In some embodiments, the mutant thermostable DNA polymerase is selected from the group consisting of Klentaq® 1, Klentaq® LA, Cesium Klentaq® AC, Cesium Klentaq® AC LA, Cesium Klentaq® C, Cesium Klentaq® C LA, Omni Klentaq®, Omni Klentaq® 2, Omni Klentaq® LA, Omni Taq, OmniTaq LA, Omni Taq 2, Omni Taq 3, Hemo KlenTaq®, KAPA Blood DNA polymerase, KAPA3G Plant DNA polymerase, KAPA 3G Robust DNA polymerase, MyTaq™ Blood, and PHUSION® Blood II DNA polymerase. In some embodiments, the mutant thermostable DNA polymerase is a hot start thermostable DNA polymerase. In some embodiments, the hot start thermostable DNA polymerase is APTATAQ™, Hawk Z05, or PHUSION® Blood II DNA polymerase.

In some embodiments of any of the preceding aspects, the thermostable nucleic acid polymerase is inhibited by the presence of subject-derived cells or cell debris under normal reaction conditions. In some embodiments, the thermostable nucleic acid polymerase is inhibited by the presence of whole blood under normal reaction conditions. In some embodiments, the thermostable nucleic acid polymerase is inhibited by 1% (v/v) whole blood under normal reaction conditions. In some embodiments, the thermostable nucleic acid polymerase is inhibited by 8% (v/v) whole blood under normal reaction conditions. In some embodiments, the normal reaction conditions are the reaction conditions recommended by the manufacturer of the thermostable DNA polymerase.

In some embodiments of any of the preceding aspects, the method further includes amplifying one or more additional target nucleic acids in a multiplexed PCR reaction to generate one or more additional amplicons.

In some embodiments of any of the preceding aspects, an amplicon is produced in the presence of at least 10 µg of subject DNA. In some embodiments, an amplicon is produced in the presence of at least 20 µg of subject DNA. In some embodiments, an amplicon is produced in the presence of at least 35 µg of subject DNA.

In some embodiments of any of the preceding aspects, the method results in the production of at least $10^6$ copies of the amplicon. In some embodiments, the method results in the production of at least $10^9$ copies of the amplicon. In some embodiments, the method results in the production of at least $10^{10}$ copies of the amplicon. In some embodiments, the method results in the production of at least $10^{12}$ copies of the amplicon.

In some embodiments of any of the preceding aspects, the method further includes detecting the amplicon or the one or more additional amplicons. In some embodiments, the amplicon or the one or more additional amplicons is detected by optical, fluorescent, mass, density, magnetic, chromatographic, and/or electrochemical measurement. In some embodiments, detecting the amplicon includes the following steps: (a') preparing an assay sample by adding to a portion of the amplified solution from about $1\times10^6$ to about $1\times10^{13}$ magnetic particles per milliliter of the amplified solution, wherein the magnetic particles have a mean diameter of from about 700 nm to about 950 nm and binding moieties on their surface, the binding moieties operative to alter aggregation of the magnetic particles in the presence of the amplicon, wherein said magnetic particles have a $T_2$ relaxivity per particle of from about $1\times10^9$ to about $1\times10^{12}$ mM$^{-1}$ s$^{-1}$; (b') providing the assay sample in a detection tube within a device, the device including a support defining a well for holding the detection tube including the assay sample, and having an RF coil configured to detect a signal produced by exposing the mixture to a bias magnetic field created using one or more magnets and an RF pulse sequence; (c') exposing the assay sample to a bias magnetic field and an RF pulse sequence; (d') following step (c'), measuring the signal produced by the assay sample, thereby detecting the presence or absence of the amplicon. In some embodiments, the magnetic particles include a first population of magnetic particles conjugated to a first probe, and a second population of magnetic particles conjugated to a second probe, the first probe operative to bind to a first segment of the amplicon and the second probe operative to bind to a second segment of the amplicon, wherein the magnetic particles form aggregates in the presence of the amplicon. In some embodiments, the detection occurs within 4 hours from the start of step (a). In some embodiments, the detection occurs within 3 hours from the start of step (a). In some embodiments, the method is capable of detecting $10^{12}$ copies of the amplicon. In some embodiments, the method is capable of detecting $10^{10}$ copies of the amplicon. In some embodiments, the method is capable of detecting $10^9$ copies of the amplicon.

In some embodiments of any of the preceding aspects, the target nucleic acid is characteristic of a pathogen. In some embodiments, the pathogen is a fungal pathogen, a bacterial pathogen, a protozoan pathogen, or a viral pathogen. In some embodiments, the fungal pathogen is a *Candida* spp. In some embodiments, the *Candida* spp. is selected from the group consisting of *Candida albicans, Candida guilliermondii, Candida glabrata, Candida krusei, Candida lusitaniae, Candida parapsilosis,* and *Candida tropicalis*. In some embodiments, the bacterial pathogen is selected from the group consisting of *Acinetobacter baumannii, Escherichia coli, Enterococcus faecalis, Enterococcus faecium, Klebsiella pneumoniae, Pseudomonas aeruginosa, Staphylococcus aureus, Borrelia burgdorferi, Borrelia afzelii, Borrelia garinii, Rickettsia rickettsii, Anaplasma phagocytophilum, Coxiella burnetii, Ehrlichia chaffeensis, Ehrlichia ewingii, Francisella tularensis, Streptococcus pneumoniae,* and *Neisseria meningitides*. In some embodiments, the protozoan pathogen is *Babesia microti* or *Babesia divergens*. In some embodiments, the method is capable of detecting a concentration of about 10 colony-forming units (CFU)/mL of the pathogen species in the whole blood sample. In some embodiments, the method is capable of detecting a concentration of about 5 CFU/mL of the pathogen species in the whole blood sample. In some embodiments, the method is capable of detecting a concentration of about 3 CFU/mL of the pathogen species in the whole blood sample. In some embodiments, the method is capable of detecting a concentration of about 1 CFU/mL of the pathogen species in the whole blood sample. In some embodiments, the method further includes diagnosing the subject based on the detection of the amplicon, wherein the presence of the amplicon indicates that the subject is suffering from a disease associated with the pathogen. In some embodiments, the method further includes administering to the subject a suitable therapy.

Other features and advantages of the invention will be apparent from the following detailed description, drawings, and the claims.

DETAILED DESCRIPTION OF EMBODIMENTS OF THE INVENTION

Figure 1:
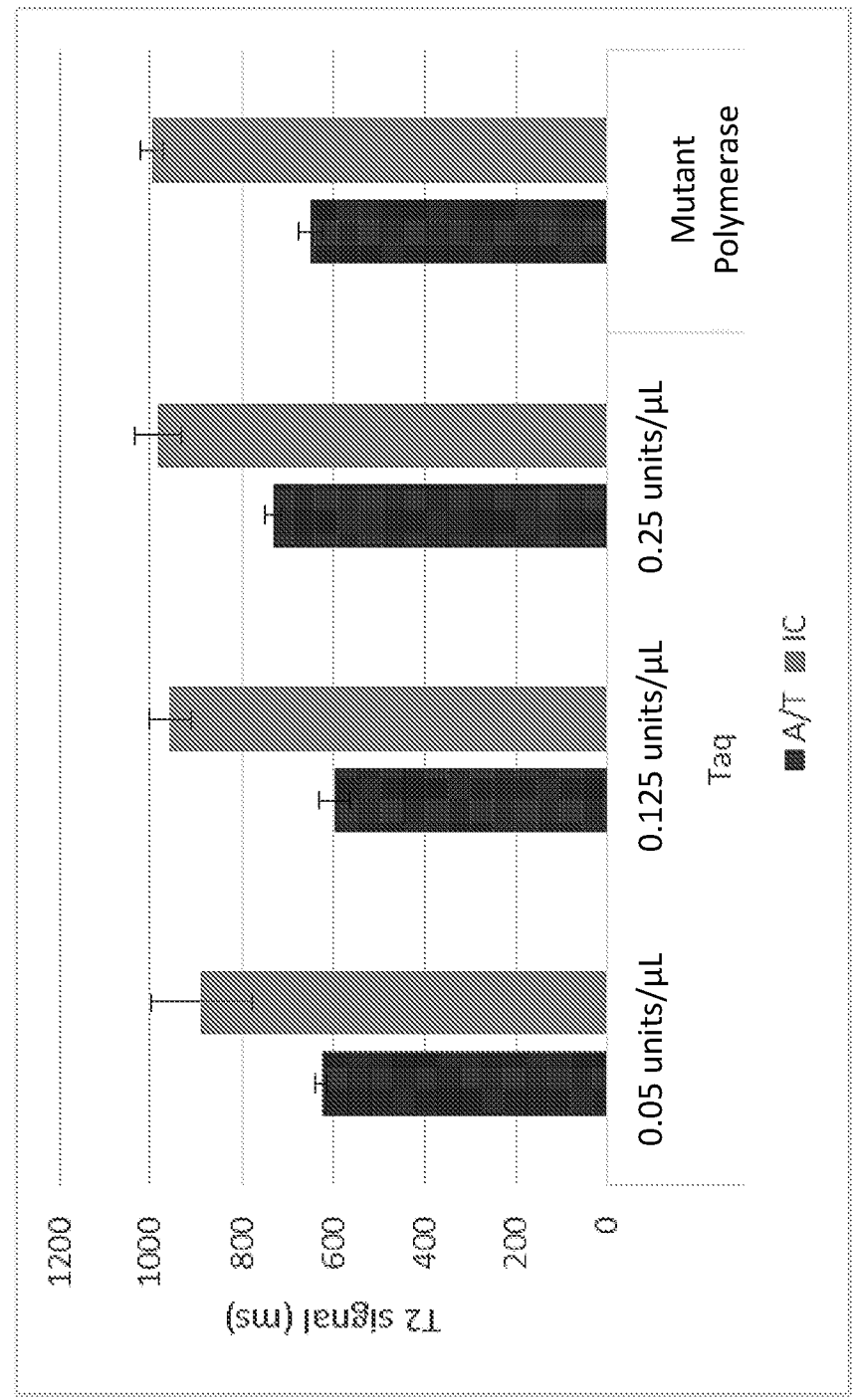
FIG. 1 is a graph showing $T_2$ magnetic resonance (T2MR) signals (ms) obtained from A/T and IC specific amplification products synthesized by Taq or a mutant thermostable DNA polymerase (n=4, "A/T" indicates *C. albicans* detection, "IC" indicates Internal Control detection).

The invention provides methods, systems, cartridges, and panels for amplification of one or more target nucleic acids in complex biological samples containing cells and/or cell debris. In some embodiments, the invention also provides methods of detecting target nucleic acid amplicons. In some embodiments, detection of the target nucleic acid amplicon(s) allows for rapid, accurate, and high sensitivity detection and identification of a microbial pathogen present in a biological sample containing host cells and/or cell debris (e.g., whole blood, processed whole blood (e.g., a crude whole blood lysate), serum, plasma, or other blood derivatives; bloody fluids such as wound exudate, phlegm, bile, and the like; tissue samples (e.g., tissue biopsies); and sputum (e.g., purulent sputum and bloody sputum)), which may be used, for example, for diagnosis of a disease (e.g., sepsis, bloodstream infections (BSIs) (e.g., bacteremia, fungemia (e.g., *Candidemia*), and viremia), Lyme disease, septic shock, and diseases that may manifest with similar symptoms to diseases caused by or associated with microbial pathogens, e.g., systemic inflammatory response syndrome (SIRS)). In some embodiments, the methods of the invention allow for amplification of target nucleic acids using nucleic acid polymerases (e.g., thermostable DNA polymerases, including commercially available thermostable DNA polymerases such as Taq) that are typically inhibited by the presence of complex samples containing cells and/or cell debris, e.g., blood.

In some embodiments, the methods and systems of the invention employ magnetic particles. In some embodiments, the methods and systems employ an NMR unit, optionally one or more magnetic assisted agglomeration (MAA) units, optionally one or more incubation stations at different temperatures, optionally one or more vortexers, optionally one or more centrifuges, optionally a fluidic manipulation station, optionally a robotic system, and optionally one or more modular cartridges, as described in International Patent Application Publication No. WO 2012/054639, which is incorporated herein by reference in its entirety. In some embodiments, the methods of the invention are performed using a fully-automated system, for example, a T2Dx® instrument. The methods, systems, devices, panels, and cartridges of the invention can be used to assay a biological sample that includes cells and/or cell debris (e.g., whole blood, processed whole blood (e.g., a crude whole blood lysate), serum, plasma, or other blood derivatives; bloody fluids such as wound exudate, phlegm, bile, and the like; tissue samples (e.g., tissue biopsies (e.g., skin biopsies, muscle biopsies, or lymph node biopsies), including homogenized tissue samples); and sputum (e.g., purulent sputum and bloody sputum). In several embodiments, the biological sample includes pathogen cell(s) and host cells and/or cell debris.

DEFINITIONS

The terms "aggregation," "agglomeration," and "clustering" are used interchangeably in the context of the magnetic particles described herein and mean the binding of two or more magnetic particles to one another, for example, via a multivalent analyte, multimeric form of analyte, antibody, nucleic acid molecule, or other binding molecule or entity. In some instances, magnetic particle agglomeration is reversible. Such aggregation may lead to the formation of "aggregates," which may include amplicons and magnetic particles bearing binding moieties.

The terms "amplification" or "amplify" or derivatives thereof as used herein mean one or more methods known in the art for copying a target or template nucleic acid, thereby increasing the number of copies of a selected nucleic acid sequence. Amplification may be exponential or linear. A target or template nucleic acid may be either DNA or RNA. The sequences amplified in this manner form an "amplified region" or "amplicon." Primers and probes can be readily designed by those skilled in the art to target a specific template nucleic acid sequence.

By "analyte" is meant a substance or a constituent of a sample to be analyzed. Exemplary analytes include one or more species of one or more of the following: a protein, a peptide, a polypeptide, an amino acid, a nucleic acid, an oligonucleotide, RNA (e.g., mRNA), DNA, an antibody, a carbohydrate, a polysaccharide, glucose, a lipid, a gas (e.g., oxygen or carbon dioxide), an electrolyte (e.g., sodium, potassium, chloride, bicarbonate, blood urea nitrogen (BUN), magnesium, phosphate, calcium, ammonia, lactate), a lipoprotein, cholesterol, a fatty acid, a glycoprotein, a proteoglycan, a lipopolysaccharide, a cell surface marker (e.g., a cell surface protein of a pathogen), a cytoplasmic marker (e.g., CD4/CD8 or CD4/viral load), a therapeutic agent, a metabolite of a therapeutic agent, a marker for the detection of a weapon (e.g., a chemical or biological weapon), an organism, a pathogen, a pathogen byproduct, a parasite (e.g., a protozoan or a helminth), a protist, a fungus (e.g., yeast or mold), a bacterium, an actinomycete, a cell (e.g., a whole cell, a tumor cell, a stem cell, a white blood cell, a T cell (e.g., displaying CD3, CD4, CD8, IL2R, CD35, or other surface markers), or another cell identified with one or more specific markers), a virus, a prion, a plant component, a plant by-product, algae, an algae by-product, plant growth hormone, an insecticide, a man-made toxin, an environmental toxin, an oil component, and components derived therefrom. In particular embodiments, the analyte is a nucleic acid (e.g., RNA (e.g., mRNA) or DNA).

A "biological sample" is a sample obtained from a subject including but not limited to blood (e.g., whole blood, processed whole blood (e.g., a crude whole blood lysate), serum, plasma, and other blood derivatives), bloody fluids (e.g., wound exudate, phlegm, bile, and the like), cerebrospinal fluid (CSF), urine, synovial fluid, breast milk, sweat, tears, saliva, semen, feces, vaginal fluid or tissue, sputum (e.g., purulent sputum and bloody sputum), nasopharyngeal aspirate or swab, lacrimal fluid, mucous, or epithelial swab (buccal swab), tissues (e.g., tissue biopsies (e.g., skin biopsies (e.g., from wounds, burns, or tick bites), muscle biopsies, or lymph node biopsies)), including tissue homogenates), organs, bones, teeth, among others. In several embodiments, the biological sample contains cells and/or cell debris derived from the subject from which the sample was obtained. In particular embodiments, the subject is a host of a pathogen, and the biological sample obtained from the subject includes subject (host)-derived cells and/or cell debris, as well as one or more pathogen cells.

As used herein, the term "small molecule" refers to a drug, medication, medicament, or other chemically synthesized compound that is contemplated for human therapeutic use.

A "biomarker" is a biological substance that can be used as an indicator of a particular disease state or particular physiological state of an organism, generally a biomarker is a protein or other native compound measured in bodily fluid whose concentration reflects the presence or severity or staging of a disease state or dysfunction, can be used to monitor therapeutic progress of treatment of a disease or disorder or dysfunction, or can be used as a surrogate measure of clinical outcome or progression. In some embodiments, the biomarker is a nucleic acid (e.g., RNA (e.g., mRNA) or DNA).

As used herein, "linked" means attached or bound by covalent bonds, non-covalent bonds, and/or linked via Van der Waals forces, hydrogen bonds, and/or other intermolecular forces.

The term "magnetic particle" refers to particles including materials of high positive magnetic susceptibility such as paramagnetic compounds, superparamagnetic compounds, and magnetite, gamma ferric oxide, or metallic iron.

As used herein, "nonspecific reversibility" refers to the colloidal stability and robustness of magnetic particles against non-specific aggregation in a liquid sample and can be determined by subjecting the particles to the intended assay conditions in the absence of a specific clustering moiety (i.e., an analyte or an agglomerator). For example, nonspecific reversibility can be determined by measuring the $T_2$ values of a solution of magnetic particles before and after incubation in a uniform magnetic field (defined as <5000 ppm) at 0.45 T for 3 minutes at 37° C. Magnetic particles are deemed to have nonspecific reversibility if the difference in $T_2$ values before and after subjecting the magnetic particles to the intended assay conditions vary by less than 10% (e.g., vary by less than 9%, 8%, 6%, 4%, 3%, 2%, or 1%). If the difference is greater than 10%, then the particles exhibit irreversibility in the buffer, diluents, and matrix tested, and manipulation of particle and matrix properties (e.g., coating and buffer formulation) may be required to produce a system in which the particles have nonspecific reversibility. In another example, the test can be applied by measuring the $T_2$ values of a solution of magnetic particles before and after incubation in a gradient magnetic field 1 Gauss/mm-10000 Gauss/mm.

As used herein, the term "NMR relaxation rate" refers to a measuring any of the following in a sample $T_1$, $T_2$, $T_1/T_2$ hybrid, $T_{1rho}$, $T_{2rho}$, and $T_2^*$. The systems and methods of the invention are designed to produce an NMR relaxation rate characteristic of whether an analyte is present in the liquid sample. In some instances the NMR relaxation rate is characteristic of the quantity of analyte present in the liquid sample.

As used herein, the term "$T_1/T_2$ hybrid" refers to any detection method that combines a $T_1$ and a $T_2$ measurement. For example, the value of a $T_1/T_2$ hybrid can be a composite signal obtained through the combination of, ratio, or difference between two or more different $T_1$ and $T_2$ measurements. The $T_1/T_2$ hybrid can be obtained, for example, by using a pulse sequence in which $T_1$ and $T_2$ are alternatively measured or acquired in an interleaved fashion. Additionally, the $T_1/T_2$ hybrid signal can be acquired with a pulse sequence that measures a relaxation rate that is comprised of both $T_1$ and $T_2$ relaxation rates or mechanisms.

A "pathogen" means an agent causing disease or illness to its host, such as an organism or infectious particle, capable of producing a disease in another organism, and includes but is not limited to bacteria, viruses, protozoa, prions, yeast and fungi or pathogen by-products. "Pathogen by-products" are those biological substances arising from the pathogen that can be deleterious to the host or stimulate an excessive host immune response, for example pathogen antigen/s, metabolic substances, enzymes, biological substances, or toxins.

By "pathogen-associated analyte" is meant an analyte characteristic of the presence of a pathogen (e.g., a bacterium, fungus, or virus) in a sample. The pathogen-associated analyte can be a particular substance derived from a pathogen (e.g., a nucleic acid (e.g., RNA (e.g., mRNA) or DNA), protein, lipid, polysaccharide, or any other material produced by a pathogen) or a mixture derived from a pathogen (e.g., whole cells, or whole viruses). In certain instances, the pathogen-associated analyte is selected to be characteristic of the genus, species, or specific strain of pathogen being detected. Alternatively, the pathogen-associated analyte is selected to ascertain a property of the pathogen, such as resistance to a particular therapy. In some embodiments, a pathogen-associated analyte may be a target nucleic acid (e.g., DNA or RNA (e.g., mRNA)) that has been amplified.

By "pulse sequence" or "RF pulse sequence" is meant one or more radio frequency pulses to be applied to a sample and designed to measure, e.g., certain NMR relaxation rates, such as spin echo sequences. A pulse sequence may also include the acquisition of a signal following one or more pulses to minimize noise and improve accuracy in the resulting signal value.

As used herein, the term "signal" refers to an NMR relaxation rate, frequency shift, susceptibility measurement, diffusion measurement, or correlation measurements.

As used herein, reference to the "size" of a magnetic particle refers to the average diameter for a mixture of the magnetic particles as determined by microscopy, light scattering, or other methods.

A "subject" is an animal, preferably a mammal (including, for example, rodents (e.g., mice or rats), farm animals (e.g., cows, sheep, horses, and donkeys), pets (e.g., cats and dogs), or primates (e.g., non-human primates and humans)). In particular embodiments, the subject is a human. A subject may be a patient (e.g., a patient having or suspected of having a disease associated with or caused by a pathogen). In some embodiments, a subject is a host of one or more pathogens.

As used herein, the term "substantially monodisperse" refers to a mixture of magnetic particles having a polydispersity in size distribution as determined by the shape of the distribution curve of particle size in light scattering measurements. The FWHM (full width half max) of the particle distribution curve less than 25% of the peak position is considered substantially monodisperse. In addition, only one peak should be observed in the light scattering experiments and the peak position should be within one standard deviation of a population of known monodisperse particles.

By "$T_2$ relaxivity per particle" is meant the average $T_2$ relaxivity per particle in a population of magnetic particles.

As used herein, "unfractionated" refers to an assay in which none of the components of the sample being tested are removed following the addition of magnetic particles to the sample and prior to the NMR relaxation measurement.

As used herein, the terms "unit" or "units," when used in reference to thermostable nucleic acid polymerases, refer to an amount of the thermostable nucleic acid polymerase (e.g., thermostable DNA polymerase). Typically a unit is defined as the amount of enzyme that will incorporate a particular amount of dNTPs (e.g., 10-20 nmol) into acid-insoluble material in 30-60 min at 65° C.-75° C. under particular assay conditions, although each manufacturer may define units differently. Unit definitions and assay conditions for commercially-available thermostable nucleic acid polymerases are known in the art. In some embodiments, one unit of thermostable nucleic acid polymerase (e.g., Taq DNA polymerase) may be the amount of enzyme that will incorporate 15 nmol of dNTP into acid-insoluble material in 30 min at 75° C. in an assay containing 1× ThermoPol® Reaction Buffer (New England Biosciences), 200 μM dNTPs including [$^3$H]-dTTP, and 15 nM primed M13 DNA.

It is contemplated that units, methods, systems, and processes of the claimed invention encompass variations and adaptations developed using information from the embodiments described herein. Throughout the description, where units and systems are described as having, including, or including specific components, or where processes and methods are described as having, including, or including specific steps, it is contemplated that, additionally, there are units and systems of the present invention that consist essentially of, or consist of, the recited components, and that there are processes and methods according to the present invention that consist essentially of, or consist of, the recited processing steps. It should be understood that the order of steps or order for performing certain actions is immaterial, unless otherwise specified, so long as the invention remains operable. Moreover, in many instances two or more steps or actions may be conducted simultaneously.

Analytes

Embodiments of the invention include methods and systems for detecting and/or measuring the concentration of one or more analytes in a complex biological sample containing cells and/or cell debris, including but not limited to blood (e.g., whole blood, a crude whole blood lysate, serum, or plasma), bloody fluids (e.g., wound exudate, phlegm, bile, and the like), tissue samples (e.g., a tissue biopsy (e.g., a skin biopsy, muscle biopsy, or lymph node biopsy), including homogenized tissue samples), or sputum. In several embodiments, the analyte may be a nucleic acid derived from an organism. In some embodiments, the nucleic acid is a target nucleic acid derived from the organism that has been amplified to form an amplicon. In some embodiments, the organism is a plant, a mammal, or a microbial species.

In several embodiments, the analyte may be derived from a microbial pathogen. In such embodiments, the biological sample may include cells and/or cell debris from the host mammalian subject as well as one or more microbial pathogen cells. In some embodiments, the analyte is derived from a Gram-negative bacterium, a Gram-positive bacterium, a fungal pathogen (e.g., a yeast (e.g., *Candida* spp.) or *Aspergillus* spp.), a protozoan pathogen, or a viral pathogen. In some embodiments, the analyte is derived from a bacterial pathogen, including *Acinetobacter* spp. (e.g., *Acinetobacter baumannii*, *Acinetobacter pittii*, and *Acinetobacter nosocomialis*), *Enterobacteriaceae* spp., *Enterococcus* spp. (e.g., *Enterococcus faecium* (including *E. faecium* with resistance marker vanA/B) and *Enterococcus faecalis*), *Klebsiella* spp. (e.g., *Klebsiella pneumoniae* (e.g., *K. pneumoniae* with resistance marker KPC) and *Klebsiella oxytoca*), *Pseudomonas* spp. (e.g., *Pseudomonas aeruginosa*), *Staphylococcus* spp. (e.g., *Staphylococcus aureus* (e.g., *S. aureus* with resistance marker mecA), *Staphylococcus haemolyticus*, *Staphylococcus lugdunensis*, *Staphylococcus maltophilia*, *Staphylococcus saprophyticus*, coagulase-positive *Staphylococcus* species, and coagulase-negative (CoNS) *Staphylococcus* species), *Streptococcus* spp. (e.g., *Streptococcus mitis*, *Streptococcus pneumoniae*, *Streptococcus agalactiae*, *Streptococcus anginosa*, *Streptococcus bovis*, *Streptococcus dysgalactiae*, *Streptococcus mutans*, *Streptococcus sanguinis*, and *Streptococcus pyogenes*), *Escherichia* spp. (e.g., *Escherichia coli*), *Stenotrophomonas* spp. (e.g., *Stenotrophomonas maltophilia*), *Proteus* spp. (e.g., *Proteus mirabilis* and *Proteus vulgaris*), *Serratia* spp. (e.g., *Serratia marcescens*), *Citrobacter* spp. (e.g., *Citrobacter freundii* and *Citrobacter koseri*), *Haemophilus* spp. (e.g., *Haemophilus influenzae*), *Listeria* spp. (e.g., *Listeria monocytogenes*), *Neisseria* spp. (e.g., *Neisseria meningitidis*), *Bacteroides* spp. (e.g., *Bacteroides fragilis*), *Burkholderia* spp. (e.g., *Burkholderia cepacia*), *Campylobacter* (e.g., *Campylobacter jejuni* and *Campylobacter coli*), *Clostridium* spp. (e.g., *Clostridium perfringens*), *Kingella* spp. (e.g., *Kingella kingae*), *Morganella* spp. (e.g., *Morganella morgana*), *Prevotella* spp. (e.g., *Prevotella buccae*, *Prevotella intermedia*, and *Prevotella melaninogenica*), *Propionibacterium* spp. (e.g., *Propionibacterium acnes*), *Salmonella* spp. (e.g., *Salmonella enterica*), *Shigella* spp. (e.g., *Shigella dysenteriae* and *Shigella flexneri*), *Borrelia* spp., (e.g., *Borrelia burgdorferi sensu lato* (*Borrelia burgdorferi*, *Borrelia afzelii*, and *Borrelia garinii*) species), *Rickettsia* spp. (including *Rickettsia rickettsii* and *Rickettsia parkeri*), *Ehrlichia* spp. (including *Ehrlichia chaffeensis*, *Ehrlichia ewingii*, and *Ehrlichia muris*-like), *Coxiella* spp. (including *Coxiella burnetii*), *Anaplasma* spp. (including *Anaplasma phagocytophi-*

*lum*), *Francisella* spp., (including *Francisella tularensis* (including *Francisella tularensis* subspp. *holarctica, mediasiatica*, and *novicida*) and *Enterobacter* spp. (e.g., *Enterobacter aerogenes* and *Enterobacter cloacae*). In some embodiments, the analyte is an antimicrobial resistance marker. Exemplary non-limiting antimicrobial resistance markers include vanA, vanB, mecA, IMP, CTX-M, KPC, NDM, OXA, VIM, and FKS. In some embodiments, the analyte is derived from a fungal pathogen, for example, *Candida* spp. (e.g., *Candida albicans, Candida guilliermondii, Candida glabrata, Candida krusei, Candida lusitaniae, Candida parapsilosis, Candida dublinensis*, and *Candida tropicalis*) and *Aspergillus* spp. (e.g., *Aspergillus fumigatus*). In some embodiments, the analyte is derived from a protozoan pathogen such as a *Babesia* spp. (e.g., *Babesia microti* and *Babesia divergens*). In some embodiments, the analyte is derived from a viral pathogen.

In some embodiments, a pathogen-associated analyte may be a nucleic acid derived from any of the organisms described above, for example, DNA or RNA (e.g., mRNA). In some embodiments, the nucleic acid is a target nucleic acid derived from the organism that has been amplified to form an amplicon. In some embodiments, the target nucleic acid may be a multi-copy locus. Use of a target nucleic acid derived from a multi-copy locus, in particular in methods involving amplification, may lead to an increase in sensitivity in the assay. Exemplary multi-copy loci may include, for example, ribosomal DNA (rDNA) operons and multi-copy plasmids. In other embodiments, the target nucleic acid may be a single-copy locus. In particular embodiments, the target nucleic acid may be derived from an essential locus, for example, an essential house-keeping gene. In particular embodiments, the target nucleic acid may be derived from a locus that is involved in virulence (e.g., a virulence gene). In any of the above embodiments, a locus may include a gene and/or an intragenic region, for example, an internally transcribed sequence (ITS) between rRNA genes (e.g., ITS1, between the 16S and 23S rRNA genes, or ITS2, between the 5S and 23S rRNA genes).

In some embodiments, a target nucleic acid may be (a) species-specific, (b) species-inclusive (in other words, present in all strains or subspecies of a given species), (c) compatible with an amplification/detection protocol, and/or (d) present in multiple copies. In particular embodiments, a target nucleic acid is chromosomally-encoded, which can help avoid loss by, for example, plasmid exchange and plasmid curing/transduction events.

Magnetic Particles and NMR-Based Detection

The methods and systems of the invention may involve use of magnetic particles and NMR. The magnetic particles can be coated with a binding moiety (e.g., oligonucleotide, antibody, etc.) such that in the presence of analyte, or multivalent binding agent, aggregates are formed. Aggregation depletes portions of the sample from the microscopic magnetic non-uniformities that disrupt the solvent's $T_2$ signal, leading to an increase in $T_2$ relaxation (see, e.g., FIG. 3 of International Patent Application Publication No. WO 2012/054639, which is incorporated herein by reference in its entirety).

The $T_2$ measurement is a single measure of all spins in the ensemble, measurements lasting typically 1-10 seconds, which allows the solvent to travel hundreds of microns, a long distance relative to the microscopic non-uniformities in the liquid sample. Each solvent molecule samples a volume in the liquid sample and the $T_2$ signal is an average (net total signal) of all (nuclear spins) on solvent molecules in the sample; in other words, the $T_2$ measurement is a net measurement of the entire environment experienced by a solvent molecule, and is an average measurement of all microscopic non-uniformities in the sample.

The observed $T_2$ relaxation rate for the solvent molecules in the liquid sample is dominated by the magnetic particles, which in the presence of a magnetic field form high magnetic dipole moments. In the absence of magnetic particles, the observed $T_2$ relaxation rates for a liquid sample are typically long (i.e., $T_2$ (water)=approximately 2000 ms, $T_2$ (blood)=approximately 1500 ms). As particle concentration increases, the microscopic non-uniformities in the sample increase and the diffusion of solvent through these microscopic non-uniformities leads to an increase in spin decoherence and a decrease in the $T_2$ value. The observed $T_2$ value depends upon the particle concentration in a non-linear fashion, and on the relaxivity per particle parameter.

In the aggregation assays of the invention, the number of magnetic particles, and if present the number of agglomerant particles, remain constant during the assay. The spatial distribution of the particles changes when the particles cluster. Aggregation changes the average "experience" of a solvent molecule because particle localization into clusters is promoted rather than more even particle distributions. At a high degree of aggregation, many solvent molecules do not experience microscopic non-uniformities created by magnetic particles and the $T_2$ approaches that of solvent. As the fraction of aggregated magnetic particles increases in a liquid sample, the observed $T_2$ is the average of the non-uniform suspension of aggregated and single (unaggregated) magnetic particles. The assays of the invention are designed to maximize the change in $T_2$ with aggregation to increase the sensitivity of the assay to the presence of analytes, and to differences in analyte concentration.

In some embodiments, the methods of the invention involve contacting a solution (e.g., a sample that includes whole blood or a crude whole blood lysate) with between from $1 \times 10^6$ to $1 \times 10^{13}$ magnetic particles per milliliter of the liquid sample (e.g., from $1 \times 10^6$ to $1 \times 10^8$, $1 \times 10^7$ to $1 \times 10^8$, $1 \times 10^7$ to $1 \times 10^9$, $1 \times 10^8$ to $1 \times 10^{10}$, $1 \times 10^9$ to $1 \times 10^{11}$, or $1 \times 10^{10}$ to $1 \times 10^{13}$ magnetic particles per milliliter).

In some embodiments, the magnetic particles used in the methods and systems of the invention have a mean diameter of from 150 nm to 1200 nm (e.g., from 150 to 250, 200 to 350, 250 to 450, 300 to 500, 450 to 650, 500 to 700 nm, 700 to 850, 800 to 950, 900 to 1050, or from 1000 to 1200 nm). For example, in some embodiments, the magnetic particles used in the methods of the invention may have a mean diameter of from 150 nm to 699 nm (e.g., from 150 to 250, 200 to 350, 250 to 450, 300 to 500, 450 to 650, or from 500 to 699 nm). In other embodiments, the magnetic particles used in the methods of the invention may have a mean diameter of from 700 nm to 1200 nm (e.g., from 700 to 850, 800 to 950, 900 to 1050, or from 1000 to 1200 nm). In particular embodiments, the magnetic particles may have a mean diameter of from 700 nm to 950 nm (e.g., from 700 to 750, 700 to 800, 700 to 850, or from 700 to 900 nm).

In some embodiments, the magnetic particles used in the methods of the invention may have a $T_2$ relaxivity per particle of from $1 \times 10^8$ to $1 \times 10^{12}$ mM$^{-1}$ s$^{-1}$ (e.g., from $1 \times 10^8$ to $1 \times 10^9$, $1 \times 10^8$ to $1 \times 10^{10}$, $1 \times 10^9$ to $1 \times 10^{10}$, $1 \times 10^9$ to $1 \times 10^{11}$, or from $1 \times 10^{10}$ to $1 \times 10^{12}$ mM$^{-1}$ s$^{-1}$). In some embodiments, the magnetic particles have a $T_2$ relaxivity per particle of from $1 \times 10^9$ to $1 \times 10^{12}$ mM$^{-1}$ s$^{-1}$ (e.g., from $1 \times 10^9$ to $1 \times 10^{10}$, $1 \times 10^9$ to $1 \times 10^{11}$, or from $1 \times 10^{10}$ to $1 \times 10^{12}$ mM$^{-1}$ s$^{-1}$).

In some embodiments, the magnetic particles may be substantially monodisperse. In some embodiments, the magnetic particles in a liquid sample (e.g., a biological sample containing cells and/or cell debris, including but not limited to blood (e.g., whole blood, a crude whole blood lysate, serum, or plasma), bloody fluids (e.g., wound exudate, phlegm, bile, and the like), tissue samples (e.g., tissue biopsies (e.g., skin biopsies, muscle biopsies, or lymph node biopsies), including homogenized tissue samples), or sputum) may exhibit nonspecific reversibility in the absence of the one or more analytes and/or multivalent binding agent. In some embodiments, the magnetic particles may further include a surface decorated with a blocking agent selected from albumin, fish skin gelatin, gamma globulin, lysozyme, casein, peptidase, and an amine-bearing moiety (e.g., amino polyethyleneglycol, glycine, ethylenediamine, or amino dextran.

Medical Conditions

The methods of the invention can also be used to monitor and diagnose diseases and other medical conditions. In some embodiments, the methods of the invention may be used to monitor and diagnose disease in a multiplexed, automated, no sample preparation system.

The methods and systems of the invention can be used to identify and monitor the pathogenesis of disease in a subject, to select therapeutic interventions, and to monitor the effectiveness of the selected treatment. For example, for a patient having or at risk of bacteremia and/or sepsis, the methods and systems of the invention can be used to identify the infectious pathogen, pathogen load, and to monitor white blood cell count and/or biomarkers indicative of the status of the infection. The identity of the pathogen can be used to select an appropriate therapy. In some embodiments, the methods may further include administering a therapeutic agent following monitoring or diagnosing an infectious disease. The therapeutic intervention (e.g., a particular antibiotic agent) can be monitored as well to correlate the treatment regimen to the circulating concentration of antibiotic agent and pathogen load to ensure that the patient is responding to treatment.

Exemplary diseases that can be diagnosed and/or monitored by the methods and systems of the invention include diseases caused by or associated with microbial pathogens (e.g., bacterial infection or fungal infection), Lyme disease, bloodstream infection (e.g., bacteremia or fungemia), pneumonia, peritonitis, osteomyeletis, meningitis, empyema, urinary tract infection, sepsis, septic shock, and septic arthritis) and diseases that may manifest with similar symptoms to diseases caused by or associated with microbial pathogens (e.g., SIRS).

For example, the methods and systems of the invention may be used to diagnose and/or monitor a disease caused by the following non-limiting examples of pathogens: bacterial pathogens, including *Acinetobacter* spp. (e.g., *Acinetobacter baumannii, Acinetobacter pittii,* and *Acinetobacter nosocomialis*), *Enterobacteriaceae* spp., *Enterococcus* spp. (e.g., *Enterococcus faecium* (including *E. faecium* with resistance marker vanA/B) and *Enterococcus faecalis*), *Klebsiella* spp. (e.g., *Klebsiella pneumoniae* (e.g., *K. pneumoniae* with resistance marker KPC) and *Klebsiella oxytoca*), *Pseudomonas* spp. (e.g., *Pseudomonas aeruginosa*), *Staphylococcus* spp. (e.g., *Staphylococcus aureus* (e.g., *S. aureus* with resistance marker mecA), *Staphylococcus haemolyticus, Staphylococcus lugdunensis, Staphylococcus maltophilia, Staphylococcus saprophyticus*, coagulase-positive *Staphylococcus* species, and coagulase-negative (CoNS) *Staphylococcus* species), *Streptococcus* spp. (e.g., *Streptococcus mitis, Streptococcus pneumoniae, Streptococcus agalactiae, Streptococcus anginosa, Streptococcus bovis, Streptococcus dysgalactiae, Streptococcus mutans, Streptococcus sanguinis,* and *Streptococcus pyogenes*), *Escherichia* spp. (e.g., *Escherichia coli*), *Stenotrophomonas* spp. (e.g., *Stenotrophomonas maltophilia*), *Proteus* spp. (e.g., *Proteus mirabilis* and *Proteus vulgaris*), *Serratia* spp. (e.g., *Serratia marcescens*), *Citrobacter* spp. (e.g., *Citrobacter freundii* and *Citrobacter koseri*), *Haemophilus* spp. (e.g., *Haemophilus influenzae*), *Listeria* spp. (e.g., *Listeria monocytogenes*), *Neisseria* spp. (e.g., *Neisseria meningitidis*), *Bacteroides* spp. (e.g., *Bacteroides fragilis*), *Burkholderia* spp. (e.g., *Burkholderia cepacia*), *Campylobacter* (e.g., *Campylobacter jejuni* and *Campylobacter coli*), *Clostridium* spp. (e.g., *Clostridium perfringens*), *Kingella* spp. (e.g., *Kingella kingae*), *Morganella* spp. (e.g., *Morganella morgana*), *Prevotella* spp. (e.g., *Prevotella buccae, Prevotella intermedia,* and *Prevotella melaninogenica*), *Propionibacterium* spp. (e.g., *Propionibacterium acnes*), *Salmonella* spp. (e.g., *Salmonella enterica*), *Shigella* spp. (e.g., *Shigella dysenteriae* and *Shigella flexneri*), and *Enterobacter* spp. (e.g., *Enterobacter aerogenes* and *Enterobacter cloacae*); and fungal pathogens including but not limited to *Candida* spp. (e.g., *Candida albicans, Candida guilliermondii, Candida glabrata, Candida krusei, Candida lusitaniae, Candida parapsilosis, Candida dublinensis,* and *Candida tropicalis*) and *Aspergillus* spp. (e.g., *Aspergillus fumigatus*). In some embodiments, the pathogen may be a *Borrelia* spp., including *Borrelia burgdorferi* sensu lato (*Borrelia burgdorferi, Borrelia afzelii,* and *Borrelia garinii*) species, *Borrelia americana, Borrelia andersonii, Borrelia bavariensis, Borrelia bissettii, Borrelia carolinensis, Borrelia californiensis, Borrelia chilensis, Borrelia* genomosp. 1 and 2, *Borrelia japonica, Borrelia kurtenbachii, Borrelia lusitaniae, Borrelia myomatoii, Borrelia sinica, Borrelia spielmanii, Borrelia tanukii, Borrelia turdi, Borrelia valaisiana* and unclassified *Borrelia* spp. In other embodiments, the pathogen may be selected from the following: *Rickettsia* spp. (including *Rickettsia rickettsii* and *Rickettsia parkeri*), *Ehrlichia* spp. (including *Ehrlichia chaffeensis, Ehrlichia ewingii,* and *Ehrlichia muris*-like), *Coxiella* spp. (including *Coxiella burnetii*), *Babesia* spp. (including *Babesia microti* and *Babesia divergens*), *Anaplasma* spp. (including *Anaplasma phagocytophilum*), *Francisella* spp., (including *Francisella tularensis* (including *Francisella tularensis* subspp. *holarctica, mediasiatica,* and *novicida*)), *Streptococcus* spp. (including *Streptococcus pneumonia*), and *Neisseria* spp. (including *Neisseria meningitidis*).

Treatment

In some embodiments, the methods further include administering a therapeutic agent to a subject following a diagnosis. Typically, the identification of a particular pathogen in a biological sample obtained from the subject (e.g., a complex sample containing host cells and/or cell debris, e.g., blood (e.g., whole blood, a crude whole blood lysate, serum, or plasma), bloody fluids (e.g., wound exudate, phlegm, bile, and the like), tissue samples (e.g., tissue biopsies (e.g., skin biopsies, muscle biopsies, or lymph node biopsies), including homogenized tissue samples), or sputum) will guide the selection of the appropriate therapeutic agent.

For example, for a bacterial infection (e.g., bacteremia), a therapy may include an antibiotic. In some instances, an antibiotic may be administered orally. In other instances, the antibiotic may be administered intravenously. Exemplary non-limiting antibiotics that may be used in the methods of the invention include but are not limited to, acrosoxacin, amifloxacin, amikacin, amoxycillin, ampicillin, aspoxicillin, azidocillin, azithromycin, aztreonam, balofloxacin, benzylpenicillin, biapenem, brodimoprim, cefaclor, cefadroxil, cefatrizine, cefcapene, cefdinir, cefetamet, ceftmetazole, cefoxitin, cefprozil, cefroxadine, ceftarolin, ceftazidime, ceftibuten, ceftobiprole, cefuroxime, cephalexin, cephalonium, cephaloridine, cephamandole, cephazolin, cephradine, chlorquinaldol, chlortetracycline, ciclacillin, cinoxacin, ciprofloxacin, clarithromycin, clavulanic acid, clindamycin, clofazimine, cloxacillin, colistin, danofloxacin, dapsone, daptomycin, demeclocycline, dicloxacillin, difloxacin, doripenem, doxycycline, enoxacin, enrofloxacin, erythromycin, fleroxacin, flomoxef, flucloxacillin, flumequine, fosfomycin, gentamycin, isoniazid, imipenem, kanamycin, levofloxacin, linezolid, mandelic acid, mecillinam, meropenem, metronidazole, minocycline, moxalactam, mupirocin, nadifloxacin, nafcillin, nalidixic acid, netilmycin, netromycin, nifuirtoinol, nitrofurantoin, nitroxoline, norfloxacin, ofloxacin, oxacillin, oxytetracycline, panipenem, pefloxacin, phenoxymethylpenicillin, pipemidic acid, piromidic acid, pivampicillin, pivmecillinam, polymixin-b, prulifloxacin, rufloxacin, sparfloxacin, sulbactam, sulfabenzamide, sulfacytine, sulfametopyrazine, sulphacetamide, sulphadiazine, sulphadimidine, sulphamethizole, sulphamethoxazole, sulphanilamide, sulphasomidine, sulphathiazole, teicoplanin, temafioxacin, tetracycline, tetroxoprim, tigecycline, tinidazole, tobramycin, tosufloxacin, trimethoprim, vancomycin, and pharmaceutically acceptable salts or esters thereof.

In another example, for a fungal infection, a treatment may include an antifungal agent. Exemplary antifungal agents include, but are not limited to, polyenes (e.g., amphotericin B, candicidin, filipin, hamycin, natamycin, nystatin, and rimocidin), azoles (e.g., imidazoles such as bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, and tioconazole; triazoles such as albaconazole, efinaconazole, epoxiconazole, fluconazole, isavuconazole, itraconazole, posaconazole, propiconazole, ravuconazole, terconazole, and voriconazole; and thiazoles such as abafungin), allylamines (e.g., amorolfin, butenafine, naftifine, and terbinafine), echinocandins (e.g., anidulafungin, caspofungin, and micafungin), and other antifungal agents including but not limited to benzoic acid, ciclopirox olamine, 5-flucytosin, griseofulvin, haloprogin, tolnaftate, aminocandin, chlordantoin, chlorphenesin, nifuroxime, undecylenic acid, crystal violet, and pharmaceutically acceptable salts or esters thereof.

In some embodiments, a method of treatment may include administering a treatment to an asymptomatic patient, for example, based on the detection and/or identification of a pathogen present in a biological sample derived from the patient by the methods of the invention. In other embodiments, a method of treatment may include administering a treatment to a symptomatic patient based on the detection of identification of a pathogen present in a biological sample derived from the patient by the methods of the invention. In several embodiments, the biological sample may contain cells and/or cell debris derived from both the host subject and a pathogen, including but not limited to blood (e.g., whole blood, a crude whole blood lysate, serum, or plasma), bloody fluids (e.g., wound exudate, phlegm, bile, and the like), tissue samples (e.g., tissue biopsies (e.g., skin biopsies, muscle biopsies, or lymph node biopsies), including homogenized tissue samples), or sputum (e.g., purulent sputum or bloody sputum). In some embodiments, the biological sample is blood (e.g., whole blood, a crude whole blood lysate, serum, or plasma) or a bloody fluid (e.g., wound exudate, phlegm, bile, and the like). In particular embodiments, the biological sample is whole blood. In other particular embodiments, the biological sample is a crude whole blood lysate.

In some embodiments, the treatment selected for a patient is based on the detection and/or identification of a pathogen by the methods of the invention. Appropriate treatments for different pathogen species are known in the art. In one example, if a Gram positive bacterium is detected in a biological derived from a patient, a method of treatment may involve administration of vancomycin. In another example, if a Gram negative bacterium is detected in a biological derived from a patient, a method of treatment may involve administration of pipercillin-tazobactam. In another example, in some embodiments, if an *Acinetobacter* spp. (e.g., *Acinetobacter baumannii*) is detected in a biological sample derived from a patient, a method of treatment may involve administration of colistin, meropenem, and/or gentamicin. In another example, in some embodiments, if a *Klebsiella* spp. (e.g., *Klebsiella pneumoniae*) is detected in a biological sample derived from a patient, a method of treatment may involve administration of meropenem. In yet another example, in some embodiments, if a *Pseudomonas* spp. (e.g., *Pseudomonas aeruginosa*) is detected in a biological sample derived from a patient, a method of treatment may involve administration of pipercillin-tazobactam. In a further example, in some embodiments, if an *Escherichia* spp. (e.g., *Escherichia coli*) is detected in a biological sample derived from a patient, a method of treatment may involve administration of meropenem. In another example, in some embodiments, if an *Enterococcus* spp. (e.g., *Enterococcus faecium*) is detected in a biological sample derived from a patient, a method of treatment may involve administration of daptomycin.

Assay Reagents

The methods described herein may include any suitable reagents, for example, surfactants, buffer components, additives, chelating agents, and the like. The surfactant may be selected from a wide variety of soluble non-ionic surface active agents including surfactants that are generally commercially available under the IGEPAL® trade name from GAF Company. The IGEPAL® liquid non-ionic surfactants are polyethylene glycol p-isooctylphenyl ether compounds and are available in various molecular weight designations, for example, IGEPAL® CA720, IGEPAL® CA630, and IGEPAL® CA890. Other suitable non-ionic surfactants include those available under the trade name TETRONIC® 909 from BASF Corporation. This material is a tetrafunctional block copolymer surfactant terminating in primary hydroxyl groups. Suitable non-ionic surfactants are also available under the ALPHONIC® trade name from Vista Chemical Company and such materials are ethoxylates that are non-ionic biodegradables derived from linear primary alcohol blends of various molecular weights. The surfactant may also be selected from poloxamers, such as polyoxyethylene-polyoxypropylene block copolymers, such as those available under the trade names SYNPERONIC® PE series (ICI), PLURONIC® series (BASF), Supronic, MONOLAN®, PLURACARE®, and PLURODAC®, polysorbate surfactants, such as TWEEN® 20 (PEG-20 sorbitan monolaurate), and glycols such as ethylene glycol and propylene glycol.

Such non-ionic surfactants may be selected to provide an appropriate amount of detergency for an assay without having a deleterious effect on assay reactions. In particular, surfactants may be included in a reaction mixture for the purpose of suppressing non-specific interactions among various ingredients of the aggregation assays of the invention. The non-ionic surfactants are typically added to the liquid sample prior in an amount from 0.01% (w/w) to 5% (w/w).

The non-ionic surfactants may be used in combination with one or more proteins (e.g., albumin, fish skin gelatin, lysozyme, or transferrin) also added to the liquid sample prior in an amount from 0.01% (w/w) to 5% (w/w).

Furthermore, the assays, methods, and cartridge units of the invention can include additional suitable buffer components (e.g., Tris base, selected to provide a pH of about 7.8 to 8.2 in the reaction milieu); and chelating agents to scavenge cations (e.g., ethylene diamine tetraacetic acid (EDTA), EDTA disodium, citric acid, tartaric acid, glucuronic acid, saccharic acid or suitable salts thereof).

Amplification and Detection of Nucleic Acids from Complex Samples

In several embodiments, the methods and systems of the invention involve amplification of one or more nucleic acids. Amplification may be exponential or linear. A target or template nucleic acid may be either DNA or RNA (e.g., mRNA). The sequences amplified in this manner form an "amplified region" or "amplicon." Primer probes can be readily designed by those skilled in the art to target a specific template nucleic acid sequence. In certain preferred embodiments, resulting amplicons are short to allow for rapid cycling and generation of copies. The size of the amplicon can vary as needed, for example, to provide the ability to discriminate target nucleic acids from non-target nucleic acids. For example, amplicons can be less than about 1,000 nucleotides in length. Desirably the amplicons are from 100 to 500 nucleotides in length (e.g., 100 to 200, 150 to 250, 300 to 400, 350 to 450, or 400 to 500 nucleotides in length). In some embodiments, more than one (e.g., 1, 2, 3, 4, 5, 6, 7, 8, 9, 10, or more than 10) target nucleic acids may be amplified in one reaction. In other embodiments, a single target nucleic acid may be amplified in one reaction. In some embodiments, the invention provides amplification-based nucleic acid detection assays conducted in complex samples containing cells and/or cell debris, including but not limited to blood (e.g., whole blood, a crude whole blood lysate, serum, or plasma), bloody fluids (e.g., wound exudate, phlegm, bile, and the like), tissue samples (e.g., tissue biopsies (e.g., skin biopsies, muscle biopsies, or lymph node biopsies), including homogenized tissue samples), or sputum (e.g., purulent sputum or bloody sputum). In several embodiments, the method provides methods for amplifying target nucleic acids in a biological sample that includes cells and/or cell debris derived from both a host mammalian subject and from a microbial organism, particularly a microbial pathogen.

Sample preparation typically involves removing or providing resistance for common PCR inhibitors found in complex samples containing cells and/or cell debris. Common inhibitors are listed in Table 1 (see also Wilson, Appl. Environ. Microbiol., 63:3741 (1997)). The "facilitators" in Table 1 indicate methodologies or compositions that may be used to reduce or overcome inhibition. Inhibitors typically act by either prevention of cell lysis, degradation or sequestering a target nucleic acid, and/or inhibition of a polymerase activity. The most commonly employed polymerase, Taq, is typically inhibited by the presence of 0.1% blood in a reaction. Mutant Taq polymerases have been engineered that are resistant to common inhibitors (e.g., hemoglobin and/or humic acid) found in blood (Kermekchiev et al., Nucl. Acid. Res., 37(5): e40, (2009)). Manufacturer recommendations indicate these mutations enable direct amplification from up to 20% blood. Despite resistance afforded by the mutations, accurate real time PCR detection is complicated due to fluorescence quenching observed in the presence of blood sample (Kermekchiev et al., Nucl. Acid. Res., 37:e40 (2009)).

TABLE 1

PCR inhibitors and facilitators for overcoming inhibition.

| Sample or Specimen Type | Target | Inhibitor | Facilitator |
|---|---|---|---|
| feces | Escherichia coli | >10$^3$ bacterial cells | ion-exchange column |
| CSF | Treponema pallidum | Cell debris causing nonspecific amplification | nested primers |
| whole blood | mammalian tissue | >4 µl of blood/100-ml reaction mix (hemoglobin) | 1-2% blood per reaction |
| feces | Rotavirus | unknown dilution | cellulose fiber |
| clinical specimens | Cytomegalovirus | unidentified components | glass bead extraction |
| human blood and tissue | human genes | DNA binding proteins | thermophilic protease from Thermus strain rt44A |
| mammalian tissue | Mammalian tissue genetics | thermal cycler variations | formamide |
| mammalian tissue | Mammalian tissue genetics | thermal cycler variations | DMSO, glycerol, PEG, organic solvents |
| clinical specimens | Treponema pallidum | unknown factors | Various substrate-specific physicochemical methods |
| forensic semen samples | Sperm | Genotyping errors; selective/total PCR inhibition by vaginal microorganisms | |
| feces | Salmonella enterica | various body fluids | immunomagnetic separation |
| feces | Various enteric viruses | unknown | size exclusion chromatography, physicochemical extraction |
| clinical specimens | Herpes simplex virus | endogenous inhibitors, random effects | repurification, coamplified positive control |
| feces | Escherichia coli | nonspecific inhibitors, urea, hemoglobin, heparin, phenol, SDS | additional primers and reaction cyclers, booster PCR |

TABLE 1-continued

PCR inhibitors and facilitators for overcoming inhibition.

| Sample or Specimen Type | Target | Inhibitor | Facilitator |
|---|---|---|---|
| tissue culture | Cytomegalovirus HIV | glove powder | |
| suspensions, skin biopsies | *Mycobacterium leprae* | mercury-based fixatives, neutral buffered formaline | reduced fixation times, ethanol fixation |
| clinical specimens | *Mycobacterium tuberculosis* | unknown inhibitors in pus, tissue biopsies, sputum, pleural fluid | physicochemical extraction |
| mammalian tissue | mammalian tissue genetics | unknown contaminant of reverse transcriptase | additional DNA |
| formalin-fixed paraffin tissue | Hepatitis C virus | ribonucleotide vanadyl complexes | phenol/chloroform extraction |
| nasopharyngeal aspirates and swabs | *Bordetella pertussis* | unknown inhibitors | phenol/chloroform extraction |
| human mononuclear blood cells | HIV type I | detergents | mineral oil |
| bloodstain | human mitochondrial DNA | unidentified heme compound, hemin | BSA |
| blood | various | heparin | alternative polymerases and buffers, chelex, spermine, [Mg2+], glycerol, BSA, heparinase |
| sputa | *Mycoplasma pneumoniae* | N-acetyl-L-cysteine, dithiothreitol, mucolytic agents | |
| human tissue | HLA-DRB1 genotyping | pollen, glove powder, impure DNA, heparin, hemoglobin | |
| clinical specimens | *Mycobacterium tuberculosis* | unknown | competitive internal control |
| dental plaque | many | unknown | diatomaceous earth, guanidium isothiocyante, ethanol, acetone |
| ancient mammalian tissues | Cytochrome b gene | unknown | ammonium acetate, ethidium bromide |

Polymerase chain reaction amplification of DNA or cDNA is a tried and trusted methodology; however, as discussed above, polymerases are inhibited by agents contained in complex biological samples containing cells and/or cell debris, including but not limited to commonly used anticoagulants and hemoglobin. Recently mutant Taq polymerases have been engineered to harbor resistance to common inhibitors found in blood and soil. Currently available polymerases, e.g., HemoKlenTaq® (New England BioLabs, Inc., Ipswich, MA) as well as OmniTaq® and OmniKlenTaq® (DNA Polymerase Technology, Inc., St. Louis, MO) are mutant (e.g., N-terminal truncation and/or point mutations) Taq polymerase that render them capable of amplifying DNA in the presence of up to 10%, 20% or 25% whole blood, depending on the product and reaction conditions (See, e.g., Kermekchiev et al. Nucl. Acids Res. 31:6139 (2003); and Kermekchiev et al., Nucl. Acid. Res., 37:e40 (2009); and see U.S. Pat. No. 7,462,475). Additionally, PHUSION® Blood Direct PCR Kits (Finnzymes Oy, Espoo, Finland), include a unique fusion DNA polymerase enzyme engineered to incorporate a double-stranded DNA binding domain, which allows amplification under conditions which are typically inhibitory to conventional polymerases such as Taq or Pfu, and allow for amplification of DNA in the presence of up to about 40% whole blood under certain reaction conditions. See Wang et al., Nucl. Acids Res. 32:1197 (2004); and see U.S. Pat. Nos. 5,352,778 and 5,500,363. Furthermore, Kapa Blood PCR Mixes (Kapa Biosystems, Woburn, MA), provide a genetically engineered DNA polymerase enzyme which allows for direct amplification of whole blood at up to about 20% of the reaction volume under certain reaction conditions. Despite these breakthroughs, direct optical detection of generated amplicons is typically not possible with existing methods since fluorescence, absorbance, and other light based methods yield signals that are quenched by the presence of blood. See Kermekchiev et al., Nucl. Acid. Res., 37:e40 (2009). Table 2 shows a list of mutant thermostable DNA polymerases that are compatible with many types of interfering substances and that may be used in the methods of the invention for amplification of target nucleic acids in biological samples containing cells and/or cell debris.

TABLE 2

Exemplary mutant thermostable DNA polymerases

| Polymerase | Reference |
|---|---|
| Klentaq ®1 | Barnes, *Proc Natl Acad Sci* USA. 91 (6): 2216-2220, 1994. |
| Klentaq ® LA | Barnes, *Proc Natl Acad Sci* USA. 91 (6): 2216-2220, 1994. |
| Cesium Klentaq ® AC | Kermekchiev et al., *Nuc. Acids Res.* 31(21): 6139-6147, 2003. |
| Cesium Klentaq ® AC LA | Kermekchiev et al., *Nuc. Acids Res.* 31(21): 6139-6147, 2003. |
| Cesium Klentaq ® C | Kermekchiev et al., *Nuc. Acids Res.* 31(21): 6139-6147, 2003. |
| Cesium Klentaq ® C LA | Kermekchiev et al., *Nuc. Acids Res.* 31(21): 6139-6147, 2003. |
| Omni Klentaq ® | Kermekchiev et al. *Nuc. Acids Res.* 37(5): e40, 2009. |

TABLE 2-continued

Exemplary mutant thermostable DNA polymerases

| Polymerase | Reference |
|---|---|
| Omni Klentaq ® 2 | Kermekchiev et al. *Nuc. Acids Res.* 37(5): e40, 2009. |
| Omni Klentaq ® LA | Kermekchiev et al. *Nuc. Acids Res.* 37(5): e40, 2009. |
| Omni Taq | Kermekchiev et al. *Nuc. Acids Res.* 37(5): e40, 2009. |
| Omni Taq LA | Kermekchiev et al. *Nuc. Acids Res.* 37(5): e40, 2009. |
| Omni Taq 2 | Kermekchiev et al. *Nuc. Acids Res.* 37(5): e40, 2009. |
| Omni Taq 3 | Kermekchiev et al. *Nuc. Acids Res.* 37(5): e40, 2009. |
| Hemo KlenTaq ® | Kermekchiev et al. *Nuc. Acids Res.* 37(5): e40, 2009. |
| KAPA Blood DNA Polymerase | KAPA Biosystems |
| KAPA3G Plant DNA Polymerase | KAPA Biosystems |
| KAPA2G Robust DNA Polymerase | KAPA Biosystems |
| MyTaq ™ Blood-PCR Kit | Bioline |
| Phusion ® Blood DNA Kit with Hot Start Phusion II | Thermo Scientific Manage et al., *Microfluid. Nanofluid.* 10, 697-702, 2011. |

A variety of impurities and components of whole blood can be inhibitory to the polymerase and primer annealing. These inhibitors can sometimes lead to generation of false positives and low sensitivities. To reduce the generation of false positives and low sensitivities when amplifying and detecting nucleic acids in complex samples, it is desirable to utilize a thermal stable polymerase not inhibited by whole blood samples, for example as described above, and include one or more internal PCR assay controls (see Rosenstraus et al. J. Clin Microbiol. 36:191 (1998) and Hoofar et al., J. Clin. Microbiol. 42:1863 (2004)).

For example, the assay can include an internal control nucleic acid that contains primer binding regions identical to those of the target sequence to assure that clinical specimens are successfully amplified and detected. In some embodiments, the target nucleic acid and internal control can be selected such that each has a unique probe binding region that differentiates the internal control from the target nucleic acid. The internal control is, optionally, employed in combination with a processing positive control, a processing negative control, and a reagent control for the safe and accurate determination and identification of an infecting organism in, e.g., a whole blood clinical sample. The internal control can be an inhibition control that is designed to co-amplify with the nucleic acid target being detected. Failure of the internal inhibition control to be amplified is evidence of a reagent failure or process error. Universal primers can be designed such that the target sequence and the internal control sequence are amplified in the same reaction tube. Thus, using this format, if the target DNA is amplified but the internal control is not it is then assumed that the target DNA is present in a proportionally greater amount than the internal control and the positive result is valid as the internal control amplification is unnecessary. If, on the other hand, neither the internal control nor the target is amplified it is then assumed that inhibition of the PCR reaction has occurred and the test for that particular sample is not valid.

The assays of the invention can include one or more positive processing controls in which one or more target nucleic acids is included in the assay (e.g., each included with one or more cartridges) at 3× to 5× the limit of detection. The measured $T_2$ for each of the positive processing controls must be above the pre-determined threshold indicating the presence of the target nucleic acid. The positive processing controls can detect all reagent failures in each step of the process (e.g., lysis, PCR, and $T_2$ detection), and can be used for quality control of the system. The assays of the invention can include one or more negative processing controls consisting of a solution free of target nucleic acid (e.g., buffer alone). The $T_2$ measurements for the negative processing control should be below the threshold indicating a negative result while the $T_2$ measured for the internal control is above the decision threshold indicating an internal control positive result. The purpose of the negative control is to detect carry-over contamination and/or reagent contamination. The assays of the invention can include one or more reagent controls. The reagent control will detect reagent failures in the PCR stage of the reaction (i.e. incomplete transfer of master mix to the PCR tubes). The reagent controls can also detect gross failures in reagent transfer prior to $T_2$ detection.

In some embodiments, complex biological samples, which may be a liquid sample (including, for example, a biological sample containing cells and/or cell debris including but not limited to blood (e.g., whole blood, a crude whole blood lysate, serum, or plasma), bloody fluids (e.g., wound exudate, phlegm, bile, and the like), tissue samples (e.g., tissue biopsies, including homogenized tissue samples), or sputum) can be directly amplified using about 5%, about 10%, about 20%, about 25%, about 30%, about 25%, about 40%, about 45%, about 50%, about 55%, about 60%, about 65%, about 70%, or more complex liquid sample in amplification reactions, and that the resulting amplicons can be directly detected from amplification reaction using, for example, magnetic resonance (MR) relaxation measurements upon the addition of conjugated magnetic particles bound to oligonucleotides complementary to the target nucleic acid sequence. Alternatively, the magnetic particles can be added to the sample prior to amplification. Thus, provided are methods for the use of nucleic acid amplification in a complex dirty sample, hybridization of the resulting amplicon to paramagnetic particles, followed by direct detection of hybridized magnetic particle conjugate and target amplicons using magnetic particle based detection systems. In particular embodiments, direct detection of hybridized magnetic particle conjugates and amplicons is via MR relaxation measurements (e.g., $T_2$, $T_1$, $T_1/T_2$ hybrid, $T_2^*$, etc). Further provided are methods which are kinetic, in order to quantify the original nucleic acid copy number within the sample (e.g., sampling and nucleic acid detection at pre-defined cycle numbers, comparison of endogenous internal control nucleic acid, use of exogenous spiked homologous competitive control nucleic acid). In some embodiments, the resulting amplicons are detected using a non-MR-based approach, for example, optical, fluorescent, mass, density, chromatographic, and/or electrochemical measurement.

While the exemplary methods described hereinafter relate to amplification using polymerase chain reaction ("PCR"), numerous other methods are known in the art for amplification of nucleic acids (e.g., isothermal methods, rolling circle methods, etc.). Those skilled in the art will understand that these other methods may be used either in place of, or together with, PCR methods. See, e.g., Saiki, "Amplification of Genomic DNA" in PCR Protocols, Innis et al., Eds., Academic Press, San Diego, Calif., pp 13-20 (1990); Wharam et al., Nucleic Acids Res. 29:E54 (2001); Hafner et al., Biotechniques, 30:852 (2001). Further amplification methods suitable for use with the present methods include, for example, reverse transcription PCR (RT-PCR), ligase chain reaction (LCR), transcription based amplification system (TAS), transcription mediated amplification (TMA), nucleic acid sequence based amplification (NASBA) method, the strand displacement amplification (SDA) method, the loop mediated isothermal amplification (LAMP) method, the isothermal and chimeric primer-initiated amplification of nucleic acid (ICAN) method, and the smart amplification system (SMAP) method. These methods, as well as others are well known in the art and can be adapted for use in conjunction with provided methods of detection of amplified nucleic acid.

The PCR method is a technique for making many copies of a specific template DNA sequence. The PCR process is disclosed in U.S. Pat. Nos. 4,683,195; 4,683,202; and 4,965,188, each of which is incorporated herein by reference. One set of primers complementary to a template DNA are designed, and a region flanked by the primers is amplified by DNA polymerase in a reaction including multiple amplification cycles. Each amplification cycle includes an initial denaturation, and up to 50 cycles of annealing, strand elongation (or extension) and strand separation (denaturation). In each cycle of the reaction, the DNA sequence between the primers is copied. Primers can bind to the copied DNA as well as the original template sequence, so the total number of copies increases exponentially with time. PCR can be performed as according to Whelan, et al, Journal of Clinical Microbiology, 33:556(1995). Various modified PCR methods are available and well known in the art. Various modifications such as the "RT-PCR" method, in which DNA is synthesized from RNA using a reverse transcriptase before performing PCR; and the "TaqMan® PCR" method, in which only a specific allele is amplified and detected using a fluorescently labeled TaqMan® probe, and Taq DNA polymerase, are known to those skilled in the art. RT-PCR and variations thereof have been described, for example, in U.S. Pat. Nos. 5,804,383; 5,407,800; 5,322,770; and 5,310,652, and references described therein, which are hereby incorporated by reference; and TaqMan® PCR and related reagents for use in the method have been described, for example, in U.S. Pat. Nos. 5,210,015; 5,876,930; 5,538,848; 6,030,787; and 6,258,569, which are hereby incorporated by reference.

In some embodiments, asymmetric PCR is performed to preferentially amplify one strand of a double-stranded DNA template. Asymmetric PCR typically involves addition of an excess of the primer for the strand targeted for amplification. An exemplary asymmetric PCR condition is 300 nM of the excess primer and 75 nM of the limiting primer to favor single strand amplification. In other embodiments, 400 nM of the excess primer and 100 nM of the limiting primer may be used to favor single strand amplification.

In some embodiments, including embodiments that employ multiplexed PCR reactions, hot start PCR conditions may be used to reduce mis-priming, primer-dimer formation, improve yield, and/or and ensure high PCR specificity and sensitivity. A variety of approaches may be employed to achieve hot start PCR conditions, including hot start DNA polymerases (e.g., hot start DNA polymerases with aptamer-based inhibitors or with mutations that limit activity at lower temperatures) as well as hot start dNTPs (e.g., CLEAN-AMP™ dNTPs, TriLink Biotechnologies).

In some embodiments, a PCR reaction may include from about 20 cycles to about 55 cycles or more (e.g., about 20, 25, 30, 35, 40, 45, 50, or 55 cycles).

LCR is a method of DNA amplification similar to PCR, except that it uses four primers instead of two and uses the enzyme ligase to ligate or join two segments of DNA. Amplification can be performed in a thermal cycler (e.g., LCx of Abbott Labs, North Chicago, IL). LCR can be performed for example, as according to Moore et al., *Journal of Clinical Microbiology* 36:1028 (1998). LCR methods and variations have been described, for example, in European Patent Application Publication No. EP0320308, and U.S. Pat. No. 5,427,930, each of which is incorporated herein by reference.

The TAS method is a method for specifically amplifying a target RNA in which a transcript is obtained from a template RNA by a cDNA synthesis step and an RNA transcription step. In the cDNA synthesis step, a sequence recognized by a DNA-dependent RNA polymerase (i.e., a polymerase-binding sequence or PBS) is inserted into the cDNA copy downstream of the target or marker sequence to be amplified using a two-domain oligonucleotide primer. In the second step, an RNA polymerase is used to synthesize multiple copies of RNA from the cDNA template. Amplification using TAS requires only a few cycles because DNA-dependent RNA transcription can result in 10-1000 copies for each copy of cDNA template. TAS can be performed according to Kwoh et al., *PNAS* 86:1173 (1989). The TAS method has been described, for example, in International Patent Application Publication No. WO1988/010315, which is incorporated herein by reference.

Transcription mediated amplification (TMA) is a transcription-based isothermal amplification reaction that uses RNA transcription by RNA polymerase and DNA transcription by reverse transcriptase to produce an RNA amplicon from target nucleic acid. TMA methods are advantageous in that they can produce 100 to 1000 copies of amplicon per amplification cycle, as opposed to PCR or LCR methods that produce only 2 copies per cycle. TMA has been described, for example, in U.S. Pat. No. 5,399,491, which is incorporated herein by reference. NASBA is a transcription-based method which for specifically amplifying a target RNA from either an RNA or DNA template. NASBA is a method used for the continuous amplification of nucleic acids in a single mixture at one temperature. A transcript is obtained from a template RNA by a DNA-dependent RNA polymerase using a forward primer having a sequence identical to a target RNA and a reverse primer having a sequence complementary to the target RNA a on the 3' side and a promoter sequence that recognizes T7 RNA polymerase on the 5' side. A transcript is further synthesized using the obtained transcript as template. This method can be performed as according to Heim, et al., *Nucleic Acids Res.*, 26:2250 (1998). The NASBA method has been described in U.S. Pat. No. 5,130,238, which is incorporated herein by reference.

The SDA method is an isothermal nucleic acid amplification method in which target DNA is amplified using a DNA strand substituted with a strand synthesized by a strand substitution type DNA polymerase lacking 5'→3' exonuclease activity by a single stranded nick generated by a restriction enzyme as a template of the next replication. A primer containing a restriction site is annealed to template, and then amplification primers are annealed to 5' adjacent sequences (forming a nick). Amplification is initiated at a fixed temperature. Newly synthesized DNA strands are nicked by a restriction enzyme and the polymerase amplification begins again, displacing the newly synthesized strands. SDA can be performed according to Walker, et al.,

*PNAS*, 89:392 (1992). SDA methods have been described in U.S. Pat. Nos. 5,455,166 and 5,457,027, each of which are incorporated by reference.

The LAMP method is an isothermal amplification method in which a loop is always formed at the 3' end of a synthesized DNA, primers are annealed within the loop, and specific amplification of the target DNA is performed isothermally. LAMP can be performed according to Nagamine et al., *Clinical Chemistry.* 47:1742 (2001). LAMP methods have been described in U.S. Pat. Nos. 6,410,278; 6,974,670; and 7,175,985, each of which are incorporated by reference.

The ICAN method is anisothermal amplification method in which specific amplification of a target DNA is performed isothermally by a strand substitution reaction, a template exchange reaction, and a nick introduction reaction, using a chimeric primer including RNA-DNA and DNA polymerase having a strand substitution activity and RNase H. ICAN can be performed according to Mukai et al., *J. Biochem.* 142: 273(2007). The ICAN method has been described in U.S. Pat. No. 6,951,722, which is incorporated herein by reference.

The SMAP (MITANI) method is a method in which a target nucleic acid is continuously synthesized under isothermal conditions using a primer set including two kinds of primers and DNA or RNA as a template. The first primer included in the primer set includes, in the 3' end region thereof, a sequence (Ac') hybridizable with a sequence (A) in the 3' end region of a target nucleic acid sequence as well as, on the 5' side of the above-mentioned sequence (Ac'), a sequence (B') hybridizable with a sequence (Bc) complementary to a sequence (B) existing on the 5' side of the above-mentioned sequence (A) in the above-mentioned target nucleic acid sequence. The second primer includes, in the 3' end region thereof, a sequence (Cc') hybridizable with a sequence (C) in the 3' end region of a sequence complementary to the above-mentioned target nucleic acid sequence as well as a loopback sequence (D-Dc') including two nucleic acid sequences hybridizable with each other on an identical strand on the 5' side of the above-mentioned sequence (Cc'). SMAP can be performed according to Mitani et al., *Nat. Methods,* 4(3): 257 (2007). SMAP methods have been described in U.S. Patent Application Publication Nos. 2006/0160084, 2007/0190531 and 2009/0042197, each of which is incorporated herein by reference.

The amplification reaction can be designed to produce a specific type of amplified product, such as nucleic acids that are double stranded; single stranded; double stranded with 3' or 5' overhangs; or double stranded with chemical ligands on the 5' and 3' ends. The amplified PCR product can be detected by: (i) hybridization of the amplified product to magnetic particle bound complementary oligonucleotides, where two different oligonucleotides are used that hybridize to the amplified product such that the nucleic acid serves as an interparticle tether promoting particle agglomeration; (ii) hybridization mediated detection where the DNA of the amplified product must first be denatured; (iii) hybridization mediated detection where the particles hybridize to 5' and 3' overhangs of the amplified product; (iv) binding of the particles to the chemical or biochemical ligands on the termini of the amplified product, such as streptavidin functionalized particles binding to biotin functionalized amplified product.

The systems and methods of the invention can be used to perform real time PCR and provide quantitative information about the amount of target nucleic acid present in a sample (see, e.g., FIG. 52 and Example 18 of WO 2012/054639). Methods for conducting quantitative real time PCR are provided in the literature (see for example: RT-PCR Protocols. *Methods in Molecular Biology*, Vol. 193. Joe O'Connell, ed. Totowa, NJ: Humana Press, 2002, 378 pp. ISBN 0-89603-875-0). Example 18 of WO 2012/054639 describes use of the methods of the invention for real time PCR analysis of a whole blood sample.

The systems and methods of the invention can be used to perform real time PCR directly in opaque samples, such as biological samples containing cells or cell debris including but not limited to blood (e.g., whole blood, a crude whole blood lysate, serum, or plasma), bloody fluids (e.g., wound exudate, phlegm, bile, and the like), tissue samples (e.g., tissue biopsies, including homogenized tissue samples), or sputum, using magnetic nanoparticles modified with capture probes and magnetic separation. Using real-time PCR allows for the quantification of a target nucleic acid without opening the reaction tube after the PCR reaction has commenced.

In one approach, biotin or avidin labeled primers can be used to perform real-time PCR. These labels would have corresponding binding moieties on the magnetic particles that could have very fast binding times. This allows for a double stranded product to be generated and allows for much faster particle binding times, decreasing the overall turnaround time. The binding chemistry would be reversible, preventing the primers from remaining particle-bound. In order to reverse the binding, the sample can be heated or the pH adjusted.

In another approach, the real-time PCR can be accomplished through the generation of duplex DNA with overhangs that can hybridize to the superparamagnetic particles. Additionally, LNA and/or fluorinated capture probes may speed up the hybridization times.

In still another approach, the particles are designed to have a hairpin that buries the capture probe binding site to the amplicon. Heating the particles to a higher melt temperature would expose the binding site of the hairpin of the capture probes on the particles to allow binding to the target.

In another approach, a probe that hybridizes to an amplicon is tethering two (or more) particles. The reaction would be conducted in the presence of a polymerase with 5' exonuclease activity, resulting in the cleavage of the interparticle tether and a subsequent change in $T_2$. The polymerase is selected to have exonuclease activity and compatibility with the matrix of choice (e.g. blood). In this approach, smaller particles (e.g., 30 nm CLIO) can be used to reduce steric hindrance of the hybridization to target or subsequent enzymatic digestion during polymerization (see, e.g., Heid et al Genome Research 1996 6: 986-994).

In another approach, two particle populations can be synthesized to bear complementary capture probes. In the absence of amplicon, the capture probes hybridize promoting particle clustering. Upon generation of amplicon, the amplicon can compete, hybridize, and displace the capture probes leading to particle declustering. The method can be conducted in the presence or absence of nanoparticles. The particles free in solution will cluster and decluster due to the thermocycling (because, e.g., the Tm can be below 95° C.). The Tm of the amplicon binding to one of the particle-immobilized capture probes can be designed such that that binding interaction is more favorable than the particle-to-particle binding interaction (by, e.g., engineering point mutations within the capture probes to thermodynamically destabilize the duplexes). In this embodiment, the particle concentration can be kept at, e.g., low or high levels.

Previous work showed that in some cases the presence of particles in the PCR reaction could inhibit PCR. For these inhibitory particles, it is envisioned that the particles could be pulled to the side of the tube (or other location within the container) to keep them out of solution during the PCR reaction. Methods can be used to release the particles back into suspension to allow them to hybridize to the PCR product and then pull them back out of solution. Other previous work has shown that specific formulations of particles are not inhibitory to the PCR reaction and can remain in solution during amplification.

In certain embodiments, the invention features the use of enzymes compatible with whole blood, e.g., mutant thermostable DNA polymerases including but not limited to NEB HemoKlenTaq™, DNAP OmniKlenTaq™, Kapa Biosystems whole blood enzyme, Thermo-Fisher Finnzymes PHUSION® enzyme, or any of the mutant thermostable DNA polymerases shown in Table 2.

The invention also features quantitative asymmetric PCR. In any of the real-time PCR methods of the invention, the method can involve the following steps:
1. aliquoting whole blood into a prepared PCR mastermix containing superparamagnetic particles;
2. prior to the first PCR cycle, closing the tube until PCR cycling is completed;
3. loading the tube onto thermal cycler;
4. running "n" cycles of standard PCR thermal cycling;
5. conducting a $T_2$ detection (the exact time duration and steps for this vary depending on the biochemical and particle design approach described below); and
6. repeating steps 4 and 5 until enough $T_2$ readings have been taken for an accurate quantification of initial target concentration.

The above methods can be used with any of the following categories of detection of aggregation or disaggregation described herein, including those described in Table 3.

TABLE 3

Categories of Detection of Aggregation or Disaggregation

| Name | Description |
| --- | --- |
| Clustering-based detection and magnetic separation | Particles >100 nm or magnetic-separation compatible. Particles removed from solution during PCR $T_2$ goes up with amplicon generation Agitation during step 5 |
| Clustering-based detection with particles >100 nm | Particles >100 nm Particles do not inhibit PCR $T_2$ goes up with amplicon generation Agitation during step 5 |
| De-clustering-based detection and magnetic separation | Particles >100 nm Particles on the side of the tube during PCR $T_2$ goes down with amplicon generation Agitation during step 5 |
| De-clustering-based detection with particles >100 nm | Particles >100 nm Particles do not inhibit PCR $T_2$ goes down with amplicon generation Agitation during step 5 |
| Clustering-based detection with particles <100 nm | Particles <100 nm (e.g., 30 nm particles) $T_2$ goes down with amplicon appearance (at least for initial cycles, $T_2$ may subsequently increase as cluster size increases) Has potential for much more rapid hybridization times No agitation required to keep particles suspended Particle concentration in nM range |
| De-clustering-based detection with particles <100 nm | Particles <100 nm (e.g., 30 nm particles) $T_2$ goes up with amplicon appearance $T_2$ could decrease as the cluster size increase above 100 nm No agitation required to keep particles suspended |

TABLE 3-continued

Categories of Detection of Aggregation or Disaggregation

| Name | Description |
| --- | --- |
| | Has potential for most rapid detection times Particle concentration in nM range |

Sample Preparation and Cell Lysis

The methods and systems of the invention may involve sample preparation and/or cell lysis. For example, a pathogen present in a biological sample containing cells or cell debris including but not limited to blood (e.g., whole blood, a crude whole blood lysate, serum, or plasma), bloody fluids (e.g., wound exudate, phlegm, bile, and the like), tissue samples (e.g., tissue biopsies, including homogenized tissue samples), or sputum may be lysed prior to amplification of a target nucleic acid. Suitable lysis methods for lysing pathogen cells in a biological sample include, for example, mechanical lysis (e.g., beadbeating and sonication), heat lysis, and alkaline lysis. In some embodiments, beadbeating may be performed by adding glass beads (e.g., 0.5 mm glass beads, 0.6 mm glass beads, 0.7 mm glass beads, 0.8 mm glass beads, or 0.9 mm glass beads) to a biological sample to form a mixture and agitating the mixture. As an example, the sample preparation and cell lysis (e.g., beadbeating) may be performed using any of the approaches and methods described in WO 2012/054639. Following lysis, the sample may include cell debris derived from mammalian host cells and/or from the pathogen cell(s) present in the sample.

In some embodiments, the methods of the invention may include preparing a tissue homogenate. Any suitable method or approach known in the art and/or described herein may be used, including but not limited to grinding (e.g., mortar and pestle grinding, cryogenic mortar and pestle grinding, or glass homogenizer), shearing (e.g., blender, rotor-stator, dounce homogenizer, or French press), beating (e.g., bead beating), or sonication. In some embodiments, several approaches may be combined to prepare a tissue homogenate.

In some embodiments, the methods of the invention involve detection of one or more pathogen-associated analytes in a whole blood sample. In some embodiments, the methods may involve disruption of red blood cells (erythrocytes). In some embodiments, the disruption of the red blood cells can be carried out using an erythrocyte lysis agent (i.e., a lysis buffer, an isotonic lysis agent, or a nonionic detergent). Erythrocyte lysis buffers which can be used in the methods of the invention include, without limitation, isotonic solutions of ammonium chloride (optionally including carbonate buffer and/or EDTA), and hypotonic solutions. The basic mechanism of hemolysis using isotonic ammonium chloride is by diffusion of ammonia across red blood cell membranes. This influx of ammonium increases the intracellular concentration of hydroxyl ions, which in turn reacts with $CO_2$ to form hydrogen carbonate. Erythrocytes exchange excess hydrogen carbonate with chloride which is present in blood plasma via anion channels and subsequently increase in intracellular ammonium chloride concentrations. The resulting swelling of the cells eventually causes loss of membrane integrity.

Alternatively, the erythrocyte lysis agent can be an aqueous solution of nonionic detergents (e.g., nonyl phenoxypolyethoxylethanol (NP-40), 4-octylphenol polyethoxylate (TRITON™ X-100), BRIJ® 58, or related nonionic surfactants, and mixtures thereof). The erythrocyte lysis agent disrupts at least some of the red blood cells, allowing a large fraction of certain components of whole blood (e.g., certain whole blood proteins) to be separated (e.g., as supernatant following centrifugation) from the white blood cells or other cells (e.g., pathogen cells (e.g., bacterial cells and/or fungal cells)) present in the whole blood sample. Following erythrocyte lysis and centrifugation, the resulting pellet may be lysed, for example, as described above.

In some embodiments, the methods of the invention may include (a) providing a whole blood sample from a subject; (b) mixing the whole blood sample with an erythrocyte lysis agent solution to produce disrupted red blood cells; (c) following step (b), centrifuging the sample to form a supernatant and a pellet, discarding some or all of the supernatant, and resuspending the pellet to form an extract, (d) lysing cells of the extract (which may include white blood cells and/or pathogen cells) to form a lysate. In some embodiments, the method further comprises amplifying one or more target nucleic acids in the lysate. In some embodiments, the sample of whole blood is from about 0.5 to about 10 mL of whole blood, for example, 0.5 mL, 1 mL, 2 mL, 3 mL, 4 mL, 5 mL, 6 mL, 7 mL, 8 mL, 9 mL, or 10 mL of whole blood. In some embodiments, the method may include washing the pellet (e.g., with a buffer such as TE buffer) prior to resuspending the pellet and optionally repeating step (c). In some embodiments, the method may include 1, 2, 3, 4, 5, or more wash steps. In other embodiments, the method is performed without performing any wash step. In some embodiments, the amplifying is in the presence of whole blood proteins, non-target nucleic acids, or both. In some embodiments, the amplifying may be in the presence of from 0.5 μg to 60 μg (e.g., 0.5 μg, 1 μg, 5 μg, 10 μg, 15 μg, 20 μg, 25 μg, 30 μg, 35 μg, 40 μg, 45 μg, 50 μg, 55 μg, or 60 μg) of subject (i.e., host) DNA. In some embodiments, the subject (i.e., host) DNA is from white blood cells of the subject.

Amplification of Target Nucleic Acids in Complex Samples Containing Cells and/or Cell Debris The invention provides methods for amplification of target nucleic acids in biological samples containing cells and/or cell debris including but not limited to blood (e.g., whole blood, a crude whole blood lysate, serum, or plasma), bloody fluids (e.g., wound exudate, phlegm, bile, and the like), tissue samples (e.g., tissue biopsies, including homogenized tissue samples), or sputum. In several embodiments, the sample contains cells and/or cell debris derived from a mammalian host subject and one or more pathogen cells.

In one embodiment, the invention provides a method for amplifying a target nucleic acid in a biological sample obtained from a subject, wherein the biological sample includes subject-derived cells or cell debris, the method comprising: (a) lysing the cells in the biological sample to form a lysate; (b) adding to the lysate a buffer solution comprising a buffering agent to form a reaction mixture, wherein the buffer solution has a moderately alkaline pH at ambient temperature; (c) following step (b), heating the reaction mixture to form a denatured reaction mixture; (d) adding a thermostable nucleic acid polymerase to the denatured reaction mixture; and (e) amplifying the target nucleic acid to form an amplified solution comprising an amplicon. In some embodiments, the final concentration of the thermostable nucleic acid polymerase in step (d) is at least about 0.01 units (e.g., about 0.01 units, about 0.02 units, about 0.03 units, about 0.04 units, about 0.05 units, about 0.06 units, about 0.07 units, about 0.08 units, about 0.09 units, about 0.10 units, about 0.15 units about 0.2 units, about 0.25 units, about 0.3 units, about 0.35 units, about 0.4 units, about 0.45 units, about 0.5 units, about 0.6 units, about 0.65 units, about 0.7 units, about 0.8 units, about 0.9 units, about 1 unit, or more) per microliter of the denatured reaction mixture. In some embodiments, step (d) includes adding to the denatured reaction mixture at least about $1\times10^{-5}$ micrograms (e.g., about $1\times10^{-5}$ micrograms, about $1.5\times10^{-5}$ micrograms, about $2\times10^{-5}$ micrograms, about $2.4\times10^{-5}$ micrograms, about $2.5\times10^{-5}$ micrograms, about $3\times10^{-5}$ micrograms, about $4\times10^{-5}$ micrograms, about $5\times10^{-5}$ micrograms, about $6\times10^{-5}$ micrograms, about $7\times10^{-5}$ micrograms, about $8\times10^{-5}$ micrograms, about $9\times10^{-5}$ micrograms, about $1\times10^{-4}$ micrograms, about $2\times10^{-4}$ micrograms, about $3\times10^{-4}$ micrograms, about $4\times10^{-4}$ micrograms, about $5\times10^{-4}$ micrograms, about $6\times10^{-4}$ micrograms, about $7\times10^{-4}$ micrograms, about $8\times10^{-4}$ micrograms, about $9\times10^{-4}$ micrograms, about $1\times10^{-3}$ micrograms, about $2\times10^{-3}$ micrograms, $3\times10^{-3}$ micrograms, about $4\times10^{-3}$ micrograms, about $5\times10^{-3}$ micrograms, about $6\times10^{-3}$ micrograms, about $7\times10^{-3}$ micrograms, about $8\times10^{-3}$ micrograms, about $9\times10^{-3}$ micrograms, about 0.01 micrograms, about 0.02 micrograms, about 0.03 micrograms, about 0.04 micrograms, about 0.05 micrograms, or more) of a thermostable nucleic acid polymerase per microliter of denatured reaction mixture. In some embodiments, the biological sample is about 0.2 mL to about 5 mL (e.g., about 0.2 mL, about 0.3 mL, about 0.4 mL, about 0.5 mL, about 0.6 mL, about 0.7 mL, about 0.8 mL, about 0.9 mL, about 1 mL, about 1.5 mL, about 2 mL, about 2.5 mL, about 3 mL, about 3.5 mL, about 4 mL, about 4.5 mL, about 5 mL, about 5.5 mL, about 6 mL, about 6.5 mL, about 7 mL, about 7.5 mL, about 8 mL, about 8.5 mL, about 9 mL, about 9.5 mL, or about 10 mL). In some embodiments, the biological sample is about 0.9 mL. In some embodiments, the biological sample is selected from the group consisting of blood, bloody fluids, tissue samples, and sputum. In some embodiments, the blood is whole blood, a crude blood lysate, serum, or plasma. In some embodiments, the bloody fluid is wound exudate, phlegm, or bile. In some embodiments, the tissue sample is a tissue biopsy. In some embodiments, the tissue biopsy is a skin biopsy, muscle biopsy, or lymph node biopsy. In some embodiments, the tissue sample is a homogenized tissue sample.

In some embodiments, the invention provides a method for amplifying a target nucleic acid in a whole blood sample, the method including: (a) providing a crude blood lysate produced by lysing the red blood cells in a whole blood sample from a subject, centrifuging the sample to form a supernatant and a pellet including cells, discarding some or all of the supernatant, optionally washing the pellet, and lysing the cells in the pellet; (b) adding to the crude blood lysate a buffer solution including a buffering agent to form a reaction mixture; (c) following step (b), heating the reaction mixture to form a denatured reaction mixture; (d) adding a thermostable nucleic acid polymerase to the denatured reaction mixture; and (e) amplifying the target nucleic acid to form an amplified solution including an amplicon.

In other embodiments, the invention provides a method for amplifying a target nucleic acid in a whole blood sample, the method including: (a) providing a crude blood lysate produced by lysing the red blood cells in a whole blood sample from a subject, centrifuging the sample to form a supernatant and a pellet including cells, discarding some or all of the supernatant, optionally washing the pellet, and lysing the cells in the pellet; (b) adding a buffer solution including a buffering agent to the crude blood lysate to form a reaction mixture, wherein the PCR buffer has a moderately alkaline pH at ambient temperature; (c) following step (b), heating the reaction mixture to form a denatured reaction mixture; (d) adding a thermostable nucleic acid polymerase to the denatured reaction mixture; and (e) amplifying the target nucleic acid to form an amplified solution including an amplicon.

In some embodiments of any of the preceding methods, the concentration of thermostable nucleic acid polymerase in the reaction mixture is elevated relative to the amount typically recommended by the manufacturer of the thermostable nucleic acid polymerase, e.g., by about 1-, 2-, 3-, 4-, 5-, 6-, 7-, 8-, 9-, or 10-fold, or more.

In yet other embodiments, the invention provides a method for amplifying a target nucleic acid in a whole blood sample, the method including: (a) providing a crude blood lysate produced by lysing the red blood cells in a whole blood sample from a subject, centrifuging the sample to form a supernatant and a pellet including cells, discarding some or all of the supernatant, optionally washing the pellet, and lysing the cells in the pellet; (b) adding a buffer solution including a buffering agent to the crude blood lysate to form a reaction mixture; (c) following step (b), heating the reaction mixture to form a denatured reaction mixture; (d) adding a thermostable nucleic acid polymerase to the denatured reaction mixture, wherein the final concentration of the thermostable nucleic acid polymerase is at least about 0.01 units (e.g., about 0.01 units, about 0.02 units, about 0.03 units, about 0.04 units, about 0.05 units, about 0.06 units, about 0.07 units, about 0.08 units, about 0.09 units, about 0.10 units, about 0.15 units about 0.2 units, about 0.25 units, about 0.3 units, about 0.35 units, about 0.4 units, about 0.45 units, about 0.5 units, about 0.6 units, about 0.65 units, about 0.7 units, about 0.8 units, about 0.9 units, about 1 unit, or more) per microliter of the denatured reaction mixture; and (e) amplifying the target nucleic acid to form an amplified solution including an amplicon.

In still other embodiments, the invention provides a method for amplifying a target nucleic acid in a whole blood sample, the method including: (a) providing a crude blood lysate produced by lysing the red blood cells in a whole blood sample from a subject, centrifuging the sample to form a supernatant and a pellet including cells, discarding some or all of the supernatant, optionally washing the pellet, and lysing the cells in the pellet; (b) adding a buffer solution including a buffering agent to the crude blood lysate to form a reaction mixture; (c) following step (b), heating the reaction mixture to form a denatured reaction mixture; (d)) adding to the denatured reaction mixture at least about $1\times10^{-5}$ micrograms (e.g., about $1\times10^{-5}$ micrograms, about $1.5\times10^{-5}$ micrograms, about $2\times10^{-5}$ micrograms, about $2.4\times10^{-5}$ micrograms, about $2.5\times10^{-5}$ micrograms, about $3\times10^{-5}$ micrograms, about $4\times10^{-5}$ micrograms, about $5\times10^{-5}$ micrograms, about $6\times10^{-5}$ micrograms, about $7\times10^{-5}$ micrograms, about $8\times10^{-5}$ micrograms, about $9\times10^{-5}$ micrograms, about $1\times10^{-4}$ micrograms, about $2\times10^{-4}$ micrograms, about $3\times10^{-4}$ micrograms, about $4\times10^{-4}$ micrograms, about $5\times10^{-4}$ micrograms, about $6\times10^{-4}$ micrograms, about $7\times10^{-4}$ micrograms, about $8\times10^{-4}$ micrograms, about $9\times10^{-4}$ micrograms, about $1\times10^{-3}$ micrograms, about $2\times10^{-3}$ micrograms, $3\times10^{-3}$ micrograms, about $4\times10^{-3}$ micrograms, about $5\times10^{-3}$ micrograms, about $6\times10^{-3}$ micrograms, about $7\times10^{-3}$ micrograms, about $8\times10^{-3}$ micrograms, about $9\times10^{-3}$ micrograms, about 0.01 micrograms, about 0.02 micrograms, about 0.03 micrograms, about 0.04 micrograms, about 0.05 micrograms, or more) of a thermostable nucleic acid polymerase per microliter of denatured reaction mixture; and; and (e) amplifying the target nucleic acid to form an amplified solution including an amplicon.

In some embodiments, the invention provides a method for amplifying a target nucleic acid in a whole blood sample, the method including one or more of the following steps: (a) providing a crude blood lysate produced by lysing the red blood cells in a whole blood sample from a subject, centrifuging the sample to form a supernatant and a pellet including cells, discarding some or all of the supernatant, optionally washing the pellet, and lysing the cells in the pellet; (b) adding to the crude blood lysate a buffer solution including a buffering agent to form a reaction mixture, wherein the buffer solution has a moderately alkaline pH at ambient temperature; (c) following step (b), heating the reaction mixture to form a denatured reaction mixture; (d) adding a thermostable nucleic acid polymerase to the denatured reaction mixture, wherein the final concentration of the thermostable nucleic acid polymerase is at least about 0.01 units (e.g., about 0.01 units, about 0.02 units, about 0.03 units, about 0.04 units, about 0.05 units, about 0.06 units, about 0.07 units, about 0.08 units, about 0.09 units, about 0.10 units, about 0.15 units about 0.2 units, about 0.25 units, about 0.3 units, about 0.35 units, about 0.4 units, about 0.45 units, about 0.5 units, about 0.6 units, about 0.65 units, about 0.7 units, about 0.8 units, about 0.9 units, about 1 unit, or more) per microliter of the denatured reaction mixture; and (e) amplifying the target nucleic acid to form an amplified solution including an amplicon.

In another example, in some embodiments, the invention provides a method for amplifying a target nucleic acid in a whole blood sample, the method including one or more of the following steps: (a) providing a crude blood lysate produced by lysing the red blood cells in a whole blood sample from a subject, centrifuging the sample to form a supernatant and a pellet including cells, discarding some or all of the supernatant, optionally washing the pellet, and lysing the cells in the pellet; (b) adding to the crude blood lysate a buffer solution including a buffering agent to form a reaction mixture, wherein the buffer solution has a moderately alkaline pH at ambient temperature; (c) following step (b), heating the reaction mixture to form a denatured reaction mixture; (d) adding to the denatured reaction mixture at least about $1\times10^{-5}$ micrograms (e.g., about $1\times10^{-5}$ micrograms, about $1.5\times10^{-5}$ micrograms, about $2\times10^{-5}$ micrograms, about $2.4\times10^{-5}$ micrograms, about $2.5\times10^{-5}$ micrograms, about $3\times10^{-5}$ micrograms, about $4\times10^{-5}$ micrograms, about $5\times10^{-5}$ micrograms, about $6\times10^{-5}$ micrograms, about $7\times10^{-5}$ micrograms, about $8\times10^{-5}$ micrograms, about $9\times10^{-5}$ micrograms, about $1\times10^{-4}$ micrograms, about $2\times10^{-4}$ micrograms, about $3\times10^{-4}$ micrograms, about $4\times10^{-4}$ micrograms, about $5\times10^{-4}$ micrograms, about $6\times10^{-4}$ micrograms, about $7\times10^{-4}$ micrograms, about $8\times10^{-4}$ micrograms, about $9\times10^{-4}$ micrograms, about $1\times10^{-3}$ micrograms, about $2\times10^{-3}$ micrograms, $3\times10^{-3}$ micrograms, about $4\times10^{-3}$ micrograms, about $5\times10^{-3}$ micrograms, about $6\times10^{-3}$ micrograms, about $7\times10^{-3}$ micrograms, about $8\times10^{-3}$ micrograms, about $9\times10^{-3}$ micrograms, about 0.01 micrograms, about 0.02 micrograms, about 0.03 micrograms, about 0.04 micrograms, about 0.05 micrograms, or more) of a thermostable nucleic acid polymerase per microliter of denatured reaction mixture; and (e) amplifying the target nucleic acid to form an amplified solution including an amplicon.

In some embodiments of any of the preceding methods, the final concentration of the thermostable nucleic acid polymerase may range from about 0.01 units to about 1 unit (e.g., about 0.01 units to about 1 unit, about 0.01 units to about 0.9 units, about 0.01 units to about 0.8 units, about 0.01 units to about 0.7 units, about 0.01 units to about 0.6 units, about 0.01 units to about 0.5 units, about 0.01 units to about 0.4 units, about 0.01 units to about 0.3 units, about 0.01 units to about 0.25 units, about 0.01 units to about 0.2 units, about 0.01 units to about 0.1 unit, about 0.02 units to about 1 unit, about 0.02 units to about 0.9 units, about 0.02 units to about 0.8 units, about 0.02 units to about 0.7 units, about 0.02 units to about 0.6 units, about 0.02 units to about 0.5 units, about 0.02 units to about 0.4 units, about 0.02 units to about 0.3 units, about 0.02 units to about 0.25 units, about 0.02 units to about 0.2 units, about 0.02 units to about 0.1 units, about 0.04 units to about 1 unit, about 0.04 units to about 0.9 units, about 0.04 units to about 0.8 units, about 0.04 units to about 0.7 units, about 0.04 units to about 0.6 units, about 0.04 units to about 0.5 units, about 0.04 units to about 0.4 units, about 0.04 units to about 0.3 units, about 0.04 units to about 0.25 units, about 0.04 units to about 0.2 units, about 0.04 units to about 0.1 units, about 0.06 units to about 1 unit, about 0.06 units to about 0.9 units, about 0.06 units to about 0.8 units, about 0.06 units to about 0.7 units, about 0.06 units to about 0.6 units, about 0.06 units to about 0.5 units, about 0.06 units to about 0.4 units, about 0.06 units to about 0.3 units, about 0.06 units to about 0.25 units, about 0.06 units to about 0.2 units, about 0.06 units to about 0.1 units, about 0.08 units to about 1 unit, about 0.08 units to about 0.9 units, about 0.08 units to about 0.8 units, about 0.08 units to about 0.7 units, about 0.08 units to about 0.6 units, about 0.08 units to about 0.5 units, about 0.08 units to about 0.4 units, about 0.08 units to about 0.3 units, about 0.08 units to about 0.25 units, about 0.08 units to about 0.2 units, about 0.08 units to about 0.1 units, about 0.1 units to about 1 unit, about 0.1 units to about 0.9 units, about 0.1 units to about 0.8 units, about 0.1 units to about 0.7 units, about 0.1 units to about 0.6 units, about 0.1 units to about 0.5 units, about 0.1 units to about 0.4 units, about 0.1 units to about 0.3 units, about 0.1 units to about 0.25 units, about 0.1 units to about 0.2 units, about 0.2 units to about 1 unit, about 0.2 units to about 0.9 units, about 0.2 units to about 0.8 units, about 0.2 units to about 0.7 units, about 0.2 units to about 0.6 units, about 0.2 units to about 0.5 units, about 0.2 units to about 0.4 units, about 0.2 units to about 0.3 units, about 0.2 units to about 0.25 units, about 0.3 units to about 1 unit, about 0.3 units to about 0.9 units, about 0.3 units to about 0.8 units, about 0.3 units to about 0.7 units, about 0.3 units to about 0.6 units, about 0.3 units to about 0.5 units, about 0.3 units to about 0.4 units, about 0.4 units to about 1 unit, about 0.4 units to about 0.9 units, about 0.4 units to about 0.8 units, about 0.4 units to about 0.7 units, about 0.4 units to about 0.6 units, about 0.4 units to about 0.5 units, about 0.5 units to about 1 unit, about 0.5 units to about 0.9 units, about 0.5 units to about 0.8 units, about 0.5 units to about 0.7 units, about 0.5 units to about 0.6 units, about 0.6 units to about 1 unit, about 0.6 units to about 0.9 units, about 0.6 units to about 0.8 units, about 0.6 units to about 0.7 units, about 0.6 units to about 0.6 units, about 0.7 units to about 1 unit, about 0.7 units to about 0.9 units, about 0.7 units to about 0.8 units, about 0.8 units to about 1 unit, or about 0.8 units to about 0.9 units) per microliter of the denatured reaction mixture.

In some embodiments of any of the preceding methods, step (d) may include adding to the denatured reaction mixture from about $1 \times 10^{-5}$ micrograms to about 0.05 micrograms (e.g., about $1 \times 10^{-5}$ micrograms to about 0.05 micrograms, about $1 \times 10^{-5}$ micrograms to about 0.025 micrograms, about $1 \times 10^{-5}$ micrograms to about 0.01 micrograms, about $1 \times 10^{-5}$ micrograms to about 0.0075 micrograms, about $1 \times 10^{-5}$ micrograms to about 0.005 micrograms, about $1 \times 10^{-5}$ micrograms to about 0.0025 micrograms, about $1 \times 10^{-5}$ micrograms to about 0.001 micrograms, about $1 \times 10^{-5}$ micrograms to about $1 \times 10^{-4}$ micrograms, about $2 \times 10^{-5}$ micrograms to about 0.05 micrograms, about $2 \times 10^{-5}$ micrograms to about 0.025 micrograms, about $2 \times 10^{-5}$ micrograms to about 0.01 micrograms, about $2 \times 10^{-5}$ micrograms to about 0.0075 micrograms, about $2 \times 10^{-5}$ micrograms to about 0.005 micrograms, about $2 \times 10^{-5}$ micrograms to about 0.0025 micrograms, about $2 \times 10^{-5}$ micrograms to about 0.001 micrograms, about $2 \times 10^{-5}$ micrograms to about $1 \times 10^{-4}$ micrograms, about $2.4 \times 10^{-5}$ micrograms to about 0.05 micrograms, about $2.4 \times 10^{-5}$ micrograms to about 0.025 micrograms, about $2.4 \times 10^{-5}$ micrograms to about 0.01 micrograms, about $2.4 \times 10^{-5}$ micrograms to about 0.0075 micrograms, about $2.4 \times 10^{-5}$ micrograms to about 0.005 micrograms, about $2.4 \times 10^{-5}$ micrograms to about 0.0025 micrograms, about $2.4 \times 10^{-5}$ micrograms to about 0.001 micrograms, about $2.4 \times 10^{-5}$ micrograms to about $1 \times 10^{-4}$ micrograms, about $5 \times 10^{-5}$ micrograms to about 0.05 micrograms, about $5 \times 10^{-5}$ micrograms to about 0.025 micrograms, about $5 \times 10^{-5}$ micrograms to about 0.01 micrograms, about $5 \times 10^{-5}$ micrograms to about 0.0075 micrograms, about $5 \times 10^{-5}$ micrograms to about 0.005 micrograms, about $5 \times 10^{-5}$ micrograms to about 0.0025 micrograms, about $5 \times 10^{-5}$ micrograms to about 0.001 micrograms, about $5 \times 10^{-5}$ micrograms to about $1 \times 10^{-4}$ micrograms, about $8 \times 10^{-5}$ micrograms to about 0.05 micrograms, about $8 \times 10^{-5}$ micrograms to about 0.025 micrograms, about $8 \times 10^{-5}$ micrograms to about 0.01 micrograms, about $8 \times 10^{-5}$ micrograms to about 0.0075 micrograms, about $8 \times 10^{-5}$ micrograms to about 0.005 micrograms, about $8 \times 10^{-5}$ micrograms to about 0.0025 micrograms, about $8 \times 10^{-5}$ micrograms to about 0.001 micrograms, about $8 \times 10^{-5}$ micrograms to about $1 \times 10^{-4}$ micrograms, about $1 \times 10^{-4}$ micrograms to about 0.05 micrograms, about $1 \times 10^{-4}$ micrograms to about 0.025 micrograms, about $1 \times 10^{-4}$ micrograms to about 0.01 micrograms, about $1 \times 10^{-4}$ micrograms to about 0.0075 micrograms, about $1 \times 10^{-4}$ micrograms to about 0.005 micrograms, about $1 \times 10^{-4}$ micrograms to about 0.0025 micrograms, about $1 \times 10^{-4}$ micrograms to about 0.001 micrograms, about $5 \times 10^{-4}$ micrograms to about 0.05 micrograms, about $5 \times 10^{-4}$ micrograms to about 0.025 micrograms, about $5 \times 10^{-4}$ micrograms to about 0.01 micrograms, about $5 \times 10^{-4}$ micrograms to about 0.0075 micrograms, about $5 \times 10^{-4}$ micrograms to about 0.005 micrograms, about $5 \times 10^{-4}$ micrograms to about 0.0025 micrograms, about $5 \times 10^{-4}$ micrograms to about 0.001 micrograms, about $1 \times 10^{-3}$ micrograms to about 0.05 micrograms, about $1 \times 10^{-3}$ micrograms to about 0.025 micrograms, about $1 \times 10^{-3}$ micrograms to about 0.01 micrograms, about $1 \times 10^{-3}$ micrograms to about 0.0075 micrograms, about $1 \times 10^{-3}$ micrograms to about 0.005 micrograms, or about $1 \times 10^{-3}$ micrograms to about 0.0025 micrograms) of a thermostable nucleic acid polymerase per microliter of denatured reaction mixture. In some embodiments of any of the preceding methods, step (c) may further include centrifuging the denatured reaction mixture prior to step (d). In some embodiments of any of the preceding methods, step (c) may include heating the reaction mixture to greater than about 55° C., e.g., 55° C., 60° C., 65° C., 70° C., 75° C., 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

In some embodiments of any of the preceding methods, the method further includes adding (i) deoxynucleotide triphosphates (dNTPs), (ii) magnesium, (iii) one or more forward primers (e.g., 1, 2, 3, 4, 5, 6, 7, 8, 9, 10, 11, or 12 forward primers), and/or (iv) one or more reverse primers (e.g., 1, 2, 3, 4, 5, 6, 7, 8, 9, 10, 11, or 12 reverse primers) during step (b) or during step (d).

In some embodiments of any of the preceding methods, the whole blood sample is about 0.2 mL to about 2 mL (e.g., about 0.2 mL, about 0.3 mL, about 0.4 mL, about 0.5 mL, about 0.6 mL, about 0.7 mL, about 0.8 mL, about 0.9 mL, about 1 mL, about 1.1 mL, about 1.2 mL, about 1.3 mL, about 1.4 mL, about 1.5 mL, about 1.6 mL, about 1.7 mL, about 1.8 mL, about 1.9 mL, or about 2 mL).

The invention allows use of a concentrated crude blood lysate prepared from a larger volume of whole blood. In some embodiments, a crude blood lysate produced from a whole blood sample of about 0.2 mL to about 10 mL has a volume of about 10 μL to about 1000 μL (e.g., about 10 μL, about 20 μL about 30 μL, about 40 μL, about 50 μL, about 60 μL, about 70 μL, about 80 μL, about 90 μL, about 100 μL, about 125 μL, about 150 μL, about 175 μL, about 200 μL, about 225 μL, about 250 μL, about 275 μL, about 300 μL, about 325 μL, about 350 μL, about 375 μL, about 400 μL, about 425 μL, about 450 μL, about 475 μL, about 500 μL, about 525 μL, about 550 μL, about 600 μL, about 625 μL, about 650 μL, about 675 μL, about 700 μL, about 725 μL, about 750 μL, about 775 μL, about 800 μL, about 825 μL, about 850 μL, about 875 μL, about 900 μL, about 925 μL, about 950 μL, about 975 μL, or about 1000 μL). In some embodiments, the crude blood lysate produced from the whole blood sample has a volume of about 25 μL to about 200 μL. In some embodiments, the crude blood lysate produced from the whole blood sample has a volume of about 50 μL.

In some embodiments, the crude blood lysate is concentrated at least 2-fold, 3-fold, 4-fold, 5-fold, 6-fold, 7-fold, 8-fold, 9-fold, 10-fold, or more compared to the whole blood sample.

In some embodiments, the reaction mixture of step (b) contains about 20% to about 60% crude blood lysate (e.g., about 20%, about 25%, about 30%, about 35%, about 40%, about 45%, about 50%, about 55%, or about 60% crude blood lysate).

In some embodiments of any of the preceding methods, the denatured reaction mixture has a volume ranging from about 0.1 μL to about 250 μL or more, e.g., about 1 μL, about 10 μL, about 20 μL, about 30 μL, about 40 μL, about 50 μL, about 50 μL, about 60 μL, about 70 μL, about 80 μL, about 90 μL, about 100 μL, about 110 μL, about 120 μL, about 130 μL, about 140 μL, about 150 μL, about 160 μL, about 170 μL, about 180 μL, about 190 μL, about 200 μL, or more. In some embodiments, the volume of the denatured reaction mixture is about 100 μL.

In another example, in some embodiments, the invention provides a method for amplifying a target nucleic acid in a sample including unprocessed whole blood, the method including: (a) providing a mixture including a buffer solution including a buffering agent, dNTPs, magnesium, a forward primer, a reverse primer, and a thermostable nucleic acid polymerase, wherein the buffer solution has a moderately alkaline pH at ambient temperature, and wherein the final concentration of the thermostable nucleic acid polymerase is at least about 0.01 units (e.g., about 0.01 units, about 0.02 units, about 0.03 units, about 0.04 units, about 0.05 units, about 0.06 units, about 0.07 units, about 0.08 units, about 0.09 units, about 0.10 units, about 0.15 units, about 0.2 units, about 0.25 units, about 0.3 units, about 0.35 units, about 0.4 units, about 0.45 units, about 0.5 units, about 0.6 units, about 0.65 units, about 0.7 units, about 0.8 units, about 0.9 units, about 1 unit, or more) per microliter of the mixture; (b) adding to the mixture a portion of a whole blood sample obtained from a subject to form a reaction mixture; and (c) amplifying the target nucleic acid to form an amplified solution including an amplicon. In some embodiments, the reaction mixture contains from about 1% to about 70% (v/v) whole blood, e.g., about 1%, about 2%, about 3%, about 4%, about 5%, about 10%, about 15%, about 20%, about 25%, about 30%, about 35%, about 40%, about 45%, about 50%, about 55%, about 60%, about 65%, or about 70% (v/v) whole blood).

In a still further example, in some embodiments, the invention provides a method for amplifying a target nucleic acid in a sample including whole blood, the method including: (a) providing a mixture, wherein the mixture includes a buffer solution including a buffering agent, dNTPs, magnesium, a forward primer, a reverse primer, and a thermostable nucleic acid polymerase, wherein the buffer solution has a moderately alkaline pH at ambient temperature, and wherein the mixture contains about at least about $1 \times 10^{-5}$ micrograms (e.g., about $1 \times 10^{-5}$ micrograms, about $1.5 \times 10^{-5}$ micrograms, about $2 \times 10^{-5}$ micrograms, about $2.4 \times 10^{-5}$ micrograms, about $2.5 \times 10^{-5}$ micrograms, about $3 \times 10^{-5}$ micrograms, about $4 \times 10^{-5}$ micrograms, about $5 \times 10^{-5}$ micrograms, about $6 \times 10^{-5}$ micrograms, about $7 \times 10^{-5}$ micrograms, about $8 \times 10^{-5}$ micrograms, about $9 \times 10^{-5}$ micrograms, about $1 \times 10^{-4}$ micrograms, about $2 \times 10^{-4}$ micrograms, about $3 \times 10^{-4}$ micrograms, about $4 \times 10^{-4}$ micrograms, about $5 \times 10^{-4}$ micrograms, about $6 \times 10^{-4}$ micrograms, about $7 \times 10^{-4}$ micrograms, about $8 \times 10^{-4}$ micrograms, about $9 \times 10^{-4}$ micrograms, about $1 \times 10^{-3}$ micrograms, about $2 \times 10^{-3}$ micrograms, $3 \times 10^{-3}$ micrograms, about $4 \times 10^{-3}$ micrograms, about $5 \times 10^{-3}$ micrograms, about $6 \times 10^{-3}$ micrograms, about $7 \times 10^{-3}$ micrograms, about $8 \times 10^{-3}$ micrograms, about $9 \times 10^{-3}$ micrograms, about 0.01 micrograms, about 0.02 micrograms, about 0.03 micrograms, about 0.04 micrograms, about 0.05 micrograms, or more) of the thermostable nucleic acid polymerase per microliter of the mixture of the thermostable nucleic acid polymerase; (b) adding to the mixture a portion of a whole blood sample obtained from a subject to form a reaction mixture; and (c) amplifying the target nucleic acid to form an amplified solution including an amplicon. In some embodiments, the reaction mixture contains from about 1% to about 70% (v/v) whole blood, e.g., about 1%, about 2%, about 3%, about 4%, about 5%, about 10%, about 15%, about 20%, about 25%, about 30%, about 35%, about 40%, about 45%, about 50%, about 55%, about 60%, about 65%, or about 70% (v/v) whole blood).

In some embodiments of any of the preceding methods, the final concentration of the thermostable nucleic acid polymerase may range from about 0.01 units to about 1 unit (e.g., about 0.01 units to about 1 unit, about 0.01 units to about 0.9 units, about 0.01 units to about 0.8 units, about 0.01 units to about 0.7 units, about 0.01 units to about 0.6 units, about 0.01 units to about 0.5 units, about 0.01 units to about 0.4 units, about 0.01 units to about 0.3 units, about 0.01 units to about 0.25 units, about 0.01 units to about 0.2 units, about 0.01 units to about 0.1 unit, about 0.02 units to about 1 unit, about 0.02 units to about 0.9 units, about 0.02 units to about 0.8 units, about 0.02 units to about 0.7 units, about 0.02 units to about 0.6 units, about 0.02 units to about 0.5 units, about 0.02 units to about 0.4 units, about 0.02 units to about 0.3 units, about 0.02 units to about 0.25 units, about 0.02 units to about 0.2 units, about 0.02 units to about 0.1 units, about 0.04 units to about 1 unit, about 0.04 unit to about 0.9 units, about 0.04 units to about 0.8 units, about 0.04 units to about 0.7 units, about 0.04 units to about 0.6 units, about 0.04 units to about 0.5 units, about 0.04 units to about 0.4 units, about 0.04 units to about 0.3 units, about 0.04 units to about 0.25 units, about 0.04 units to about 0.2 units, about 0.04 units to about 0.1 units, about 0.06 units to about 1 unit, about 0.06 units to about 0.9 units, about 0.06 units to about 0.8 units, about 0.06 units to about 0.7 units, about 0.06 units to about 0.6 units, about 0.06 units to about 0.5 units, about 0.06 units to about 0.4 units, about 0.06 units to about 0.3 units, about 0.06 units to about 0.25 units, about 0.06 units to about 0.2 units, about 0.06 units to about 0.1 units, about 0.08 units to about 1 unit, about 0.08 units to about 0.9 units, about 0.08 units to about 0.8 units, about 0.08 units to about 0.7 units, about 0.08 units to about 0.6 units, about 0.08 units to about 0.5 units, about 0.08 units to about 0.4 units, about 0.08 units to about 0.3 units, about 0.08 units to about 0.25 units, about 0.08 units to about 0.2 units, about 0.08 units to about 0.1 units, about 0.1 units to about 1 unit, about 0.1 units to about 0.9 units, about 0.1 units to about 0.8 units, about 0.1 units to about 0.7 units, about 0.1 units to about 0.6 units, about 0.1 units to about 0.5 units, about 0.1 units to about 0.4 units, about 0.1 units to about 0.3 units, about 0.1 units to about 0.25 units, about 0.1 units to about 0.2 units, about 0.2 units to about 1 unit, about 0.2 units to about 0.9 units, about 0.2 units to about 0.8 units, about 0.2 units to about 0.7 units, about 0.2 units to about 0.6 units, about 0.2 units to about 0.5 units, about 0.2 units to about 0.4 units, about 0.2 units to about 0.3 units, about 0.2 units to about 0.25 units, about 0.3 units to about 1 unit, about 0.3 units to about 0.9 units, about 0.3 units to about 0.8 units, about 0.3 units to about 0.7 units, about 0.3 units to about 0.6 units, about 0.3 units to about 0.5 units, about 0.3 units to about 0.4 units, about 0.4 units to about 1 unit, about 0.4 units to about 0.9 units, about 0.4 units to about 0.8 units, about 0.4 units to about 0.7 units, about 0.4 units to about 0.6 units, about 0.4 units to about 0.5 units, about 0.5 units to about 1 unit, about 0.5 units to about 0.9 units, about 0.5 units to about 0.8 units, about 0.5 units to about 0.7 units, about 0.5 units to about 0.6 units, about 0.6 units to about 1 unit, about 0.6 units to about 0.9 units, about 0.6 units to about 0.8 units, about 0.6 units to about 0.7 units, about 0.6 units to about 0.6 units, about 0.7 units to about 1 unit, about 0.7 units to about 0.9 units, about 0.7 units to about 0.8 units, about 0.8 units to about 1 unit, or about 0.8 units to about 0.9 units) per microliter of the mixture.

In some embodiments of any of the preceding methods, the mixture includes from about $1\times10^{-5}$ micrograms to about 0.05 micrograms (e.g., about $1\times10^{-5}$ micrograms to about 0.05 micrograms, about $1\times10^{-5}$ micrograms to about 0.025 micrograms, about $1\times10^{-5}$ micrograms to about 0.01 micrograms, about $1\times10^{-5}$ micrograms to about 0.0075 micrograms, about $1\times10^{-5}$ micrograms to about 0.005 micrograms, about $1\times10^{-5}$ micrograms to about 0.0025 micrograms, about $1\times10^{-5}$ micrograms to about 0.001 micrograms, about $1\times10^{-5}$ micrograms to about $1\times10^{-4}$ micrograms, about $2\times10^{-5}$ micrograms to about 0.05 micrograms, about $2\times10^{-5}$ micrograms to about 0.025 micrograms, about $2\times10^{-5}$ micrograms to about 0.01 micrograms, about $2\times10^{-5}$ micrograms to about 0.0075 micrograms, about $2\times10^{-5}$ micrograms to about 0.005 micrograms, about $2\times10^{-5}$ micrograms to about 0.0025 micrograms, about $2\times10^{-5}$ micrograms to about 0.001 micrograms, about $2\times10^{-5}$ micrograms to about $1\times10^{-4}$ micrograms, about $2.4\times10^{-5}$ micrograms to about 0.05 micrograms, about $2.4\times10^{-5}$ micrograms to about 0.025 micrograms, about $2.4\times10^{-5}$ micrograms to about 0.01 micrograms, about $2.4\times10^{-5}$ micrograms to about 0.0075 micrograms, about $2.4\times10^{-5}$ micrograms to about 0.005 micrograms, about $2.4\times10^{-5}$ micrograms to about 0.0025 micrograms, about $2.4\times10^{-5}$ micrograms to about 0.001 micrograms, about $2.4\times10^{-5}$ micrograms to about $1\times10^{-4}$ micrograms, about $5\times10^{-5}$ micrograms to about 0.05 micrograms, about $5\times10^{-5}$ micrograms to about 0.025 micrograms, about $5\times10^{-5}$ micrograms to about 0.01 micrograms, about $5\times10^{-5}$ micrograms to about 0.0075 micrograms, about $5\times10^{-5}$ micrograms to about 0.005 micrograms, about $5\times10^{-5}$ micrograms to about 0.0025 micrograms, about $5\times10^{-5}$ micrograms to about 0.001 micrograms, about $5\times10^{-5}$ micrograms to about $1\times10^{-4}$ micrograms, about $8\times10^{-5}$ micrograms to about 0.05 micrograms, about $8\times10^{-5}$ micrograms to about 0.025 micrograms, about $8\times10^{-5}$ micrograms to about 0.01 micrograms, about $8\times10^{-5}$ micrograms to about 0.0075 micrograms, about $8\times10^{-5}$ micrograms to about 0.005 micrograms, about $8\times10^{-5}$ micrograms to about 0.0025 micrograms, about $8\times10^{-5}$ micrograms to about 0.001 micrograms, about $8\times10^{-5}$ micrograms to about $1\times10^{-4}$ micrograms, about $1\times10^{-4}$ micrograms to about 0.05 micrograms, about $1\times10^{-4}$ micrograms to about 0.025 micrograms, about $1\times10^{-4}$ micrograms to about 0.01 micrograms, about $1\times10^{-4}$ micrograms to about 0.0075 micrograms, about $1\times10^{-4}$ micrograms to about 0.005 micrograms, about $1\times10^{-4}$ micrograms to about 0.0025 micrograms, about $1\times10^{-4}$ micrograms to about 0.001 micrograms, about $5\times10^{-4}$ micrograms to about 0.05 micrograms, about $5\times10^{-4}$ micrograms to about 0.025 micrograms, about $5\times10^{-4}$ micrograms to about 0.01 micrograms, about $5\times10^{-4}$ micrograms to about 0.0075 micrograms, about $5\times10^{-4}$ micrograms to about 0.005 micrograms, about $5\times10^{-4}$ micrograms to about 0.0025 micrograms, about $5\times10^{-4}$ micrograms to about 0.001 micrograms, about $1\times10^{-3}$ micrograms to about 0.05 micrograms, about $1\times10^{-3}$ micrograms to about 0.025 micrograms, about $1\times10^{-3}$ micrograms to about 0.01 micrograms, about $1\times10^{-3}$ micrograms to about 0.0075 micrograms, about $1\times10^{-3}$ micrograms to about 0.005 micrograms, or about $1\times10^{-3}$ micrograms to about 0.0025 micrograms) of the thermostable nucleic acid polymerase per microliter of the mixture.

In some embodiments of any of the preceding methods, the mixture has a volume ranging from about 0.1 μL to about 250 μL or more, e.g., about 1 μL, about 10 μL, about 20 μL, about 30 μL, about 40 μL, about 50 μL, about 50 μL, about 60 μL, about 70 μL, about 80 μL, about 90 μL, about 100 μL, about 110 μL, about 120 μL, about 130 μL, about 140 μL, about 150 μL, about 160 μL, about 170 μL, about 180 μL, about 190 μL, about 200 μL, or more. In some embodiments, the volume of the mixture is about 100 μL.

In some embodiments of any of the preceding methods, the moderately alkaline pH at ambient temperature is from about pH 7.1 to about pH 11.5 or higher (e.g., about pH 7.1, about pH 7.2, about pH 7.3, about pH 7.4, about pH 7.5, about pH 7.6, about pH 7.7, about pH 7.8, about pH 7.9, about pH 8.0, about pH 8.1, about pH 8.2, about pH 8.3, about pH 8.4, about pH 8.5, about pH 8.6, about pH 8.7, about pH 8.8, about pH 8.9, about pH 9.0, about pH 9.1, about pH 9.2, about pH 9.3, about pH 9.4, about pH 9.5, about pH 9.6, about pH 9.7, about pH 9.8, about pH 9.9, about pH 10.0, about pH 10.1, about pH 10.2, about pH 10.3, about pH 10.4, about pH 10.5, about pH 10.6, about pH 10.7, about pH 10.8, about pH 10.9, about pH 11, about pH 11.1, about pH 11.2, about pH 11.3, about pH 11.3, about pH 11.4, about pH 11.5, or higher. In some embodiments, the moderately alkaline pH at ambient temperature is from about pH 7.1 to about pH 11.5, about pH 7.1 to about pH 11.0, about pH 7.1 to about pH 10.5, about pH 7.1 to about pH 10.0, about pH 7.1 to about pH 9.5, about pH 7.1 to about pH 9.0, about pH 7.1 to about pH 8.5, about pH 7.1 to about pH 8, about pH 7.1 to about pH 7.5, about pH 7.5 to about pH 11.5, about pH 7.5 to about pH 11.0, about pH 7.5 to about pH 10.5, about pH 7.5 to about pH 10.0, about pH 7.5 to about pH 9.5, about pH 7.5 to about pH 9.0, about pH 7.5 to about pH 8.5, about pH 7.5 to about pH 8.0, about pH 8.0 to about pH 11.5, about pH 8.0 to about pH 11.0, about pH 8.0 to about pH 10.5, about pH 8.0 to about pH 10.0, about pH 8.0 to about pH 9.5, about pH 8.0 to about pH 9.0, about pH 8.0 to about pH 9.0, about pH 8.0 to about pH 8.5, about pH 8.5 to about pH 11.5, about pH 8.5 to about pH 11.0, about pH 8.5 to about pH 10.0, about pH 8.5 to about pH 9.5, about pH 8.5 to about pH 9.0, about pH 9.0 to about pH 11.5, about pH 9.0 to about pH 11.0, about pH 9.0 to about pH 10.5, about pH 9.0 to about pH 10.0, about pH 9.0 to about pH 9.5, about pH 9.5 to about pH 11.5, about pH 9.5 to about pH 11.0, about pH 9.5 to about pH 10.5, or about pH 9.5 to about pH 10.0. In some embodiments, the moderately alkaline pH at ambient temperature is about pH 8.7. In some embodiments, ambient temperature is about 25° C. (e.g., about 20° C., about 21° C., about 22° C., about 23° C., about 24° C., about 25° C., about 26° C., about 27° C., about 28° C., about 29° C., about 30° C.).

In some embodiments of any of the preceding methods, the pH of the buffer solution remains approximately at or above a neutral pH at 95° C. In some embodiments, the pH of the buffer solution is about pH 6.5 to about pH 10 (e.g., about pH 6.5, about pH 6.6, about pH 6.7, about pH 6.8, about pH 6.9, about pH 7.0, about pH 7.1, about pH 7.2, about pH 7.3, about pH 7.4, about pH 7.5, about pH 7.6, about pH 7.7, about pH 7.8, about pH 7.9, about pH 8.0, about pH 8.1, about pH 8.2, about pH 8.3, about pH 8.4, about pH 8.5, about pH 8.6, about pH 8.7, about pH 8.8, about pH 8.9, about pH 9.0, about pH 9.1, about pH 9.2, about pH 9.3, about pH 9.4, about pH 9.5, about pH 9.6, about pH 9.7, about pH 9.8, about pH 9.9, or about pH 10.0) at 95° C. For example, in some embodiments, the pH of the buffer solution at 95° C. is from about pH 6.5 to about pH 10.0, about pH 6.5 to about pH 9.5, about pH 6.5 to about pH 9.0, about pH 6.5 to about pH 8.5, about pH 6.5 to about pH 8.0, about pH 6.5 to about pH 7.5, about pH 7.0 to about pH 10.0, about pH 7.0 to about pH 9.5, about pH 7.0 to about pH 9.0, about pH 7.0 to about pH 8.5, about pH 7.0 to about pH 8.0, about pH 7.0 to about pH 7.5, about pH 7.5 to about pH 10.0, about pH 7.5 to about pH 9.5, about pH 7.5 to about pH 9.0, about pH 7.5 to about pH 8.5, about pH 7.5 to about pH 8.0, about pH 8.0 to about pH 10.0, about pH 8.0 to about pH 9.5, about pH 8.0 to about pH 9.0, about pH 8.0 to about pH 8.5, about pH 8.5 to about pH 10.0, about pH 8.5 to about pH 9.5, about pH 8.5 to about pH 9.0, about pH 9.0 to about pH 10.0, or about pH 9.5 to about pH 10.0.

Any suitable buffering agent may be used in the methods of the invention. For example, in some embodiments, any buffer with a pKa ranging from about 7.0 to about 9.2 (e.g., about 7.0 to about 7.6; from about 7.6 to about 8.2; or about 8.2 to about 9.2) may be used. Exemplary buffering agents with a pKa ranging from about 7.0 to about 7.6 include but are not limited to: MOPS, BES, phosphoric acid, TES, HEPES, and DIPSO. Exemplary buffering agents with a pKa ranging from about 7.6 to about 8.2 include but are not limited to: TAPSO, TEA, n-ethylmorpholine, POPSO, EPPS, HEPPSO, Tris, and Tricine. Exemplary buffering agents with a pKa ranging from about 8.2 to about 9.2 include but are not limited to: glycylglycine, Bicine, TAPS, morpholine, n-methyldiethanolamine, AMPD (2-amino-2-methyl-1,3-propanediol), diethanolamine, and AMPSO. In some embodiments, a buffering agent with a pKa greater than 9.2 may be used. Exemplary buffering agents with a pKa greater than 9.2 include but are not limited to boric acid, CHES, glycine, CAPSO, ethanolamine, AMP (2-amino-2-methyl-1-propanol), piperazine, CAPS, 1,3-diaminopropane, CABS, and piperadine.

In some embodiments of any of the preceding methods, the thermostable nucleic acid polymerase is a thermostable DNA polymerase. Any suitable thermostable DNA polymerase may be used in the methods of the invention, for example, commercially available thermostable DNA polymerases, or any thermostable DNA polymerase described herein and/or known in the art. In some embodiments, the thermostable DNA polymerase is a wild-type thermostable DNA polymerase, e.g., *Thermus aquaticus* (Taq) DNA polymerase (see, e.g., U.S. Pat. No. 4,889,818), *Thermus thermophilus* (Tth) DNA polymerase (see, e.g., U.S. Pat. Nos. 5,192,674; 5,242,818; and 5,413,926), *Thermus filiformis* (Tfi) DNA polymerase, *Thermus flavus* (Tfl) DNA polymerase, *Thermococcus litoralis* (Tli) DNA polymerase (see, e.g., U.S. Pat. No. 5,332,785), *Thermatoga maritima* (Tma) DNA polymerase, *Thermus* spp. Z05 DNA polymerase, Tsp sps17 DNA polymerase derived from *Thermus* species sps1 7, now called *Thermus oshimai* (see, e.g., U.S. Pat. No. 5,405,774), *Bacillus stearothermophilus* (Bst) DNA polymerase (see, e.g., U.S. Pat. No. 5,747,298), an archael polymerase (e.g., thermostable DNA polymerases from hyperthermophylic archaeons *Pyrococcus furiosus* (e.g., Pfu; see, e.g., U.S. Pat. No. 5,948,663), KOD DNA polymerase derived from *Pyrococcus* sp. KOD1 (e.g., U.S. Pat. No. 6,033,859), *Thermococcus litoralis* (e.g., VENT$_R$® (NEB)), and 9° N™ (NEB)), or a mutant, derivative, or fragment thereof having DNA polymerase activity (e.g., mutant DNA polymerases that include point mutations compared to a reference thermostable DNA polymerase sequence, e.g., Taq A271 F667Y, Tth A273 F668Y, and Taq A271 F667Y E681W; truncation mutants, e.g., KlenTAQ®, an N-terminal deletion variant of Taq lacking the first 280 amino acids; and mutants that include truncations and point mutations, e.g., Hemo KlenTaq®, an N-terminal deletion variant of Taq lacking the first 280 amino acids containing three internal point mutations that make it resistant to inhibitors in whole blood). For example, suitable DNA polymerases include, but are not limited to, Taq, Hemo KlenTaq®, Hawk Z05, APTATAQ™, Pfu, and VENT$_R$®.

In some embodiments, the thermostable DNA polymerase is a mutant thermostable DNA polymerase. In some embodiments, the mutant thermostable DNA polymerase is listed in Table 2. In some embodiments, the mutant thermostable DNA polymerase is selected from the group consisting of Klentaq® 1, Klentaq® LA, Cesium Klentaq® AC, Cesium Klentaq® AC LA, Cesium Klentaq® C, Cesium Klentaq® C LA, Omni Klentaq®, Omni Klentaq® 2, Omni Klentaq® LA, Omni Taq, OmniTaq LA, Omni Taq 2, Omni Taq 3, Hemo KlenTaq®, KAPA Blood DNA polymerase, KAPA3G Plant DNA polymerase, KAPA 3G Robust DNA polymerase, MyTaq™ Blood, and PHUSION® Blood II DNA polymerase. In some embodiments, the thermostable DNA polymerase is a hot start thermostable DNA polymerase (e.g., APTATAQ™, Hawk Z05, or PHUSION® Blood II DNA polymerase).

In some embodiments, the thermostable nucleic acid polymerase (e.g., thermostable DNA polymerase) is inhibited by the presence of subject-derived cells or cell debris under normal reaction conditions. In some embodiments, the thermostable nucleic acid polymerase (e.g., thermostable DNA polymerase) is inhibited by whole blood under normal reaction conditions. In some embodiments, the thermostable nucleic acid polymerase (e.g., thermostable DNA polymerase) is inhibited by 1% (v/v) whole blood under normal reaction conditions. In some embodiments, the thermostable nucleic acid polymerase (e.g., thermostable DNA polymerase) is inhibited by 8% (v/v) whole blood under normal reaction conditions. In some embodiments, the normal reaction conditions are the reaction conditions recommended by the manufacturer of the thermostable DNA polymerase or reaction conditions that are commonly used in the art.

In some embodiments of any of the preceding methods, the method further includes amplifying one or more additional target nucleic acids in a multiplexed PCR reaction to generate one or more additional amplicons. In some embodiments, the multiplexed PCR reaction amplifies 2, 3, 4, 5, 6, 7, 8, 9, 10, 11, 12, or more target nucleic acids.

In some embodiments of any of the preceding methods, an amplicon is produced in the presence of at least 1 µg of subject DNA, e.g., at least 1 µg of subject DNA, at least 5 µg of subject DNA, at least 10 µg of subject DNA, at least 15 µg of subject DNA, at least 20 µg of subject DNA, at least 25 µg of subject DNA, at least 30 µg of subject DNA, at least 35 µg of subject DNA, at least 40 µg of subject DNA, at least 45 µg of subject DNA, at least 50 µg of subject DNA, at least 55 µg of subject DNA, or at least 60 µg of subject DNA.

In some embodiments of any of the preceding methods, the method results in the production of at least $10^5$ copies of the amplicon, e.g., at least $10^5$ copies, at least $10^6$ copies, at least $10^7$ copies, at least $10^8$ copies, at least $10^9$ copies, at least $10^{10}$ copies, at least $10^{11}$ copies, at least $10^{12}$ copies, at least $10^{13}$ copies, or at least $10^{14}$ copies of the amplicon. For example, in some embodiments, the method results in the production of at least $10^8$ copies of the amplicon. In some embodiments, the method results in the production of at least $10^9$ copies of the amplicon.

Contamination Control

One potential problem in the use of amplification methods such as PCR as an analytical tool is the risk of having new reactions contaminated with old, amplified products. Potential sources of contamination include a) large numbers of target organisms in clinical specimens that may result in cross-contamination, b) plasmid clones derived from organisms that have been previously analyzed and that may be present in larger numbers in the laboratory environment, and c) repeated amplification of the same target sequence leading to accumulation of amplification products in the laboratory environment. A common source of the accumulation of the PCR amplicon is aerosolization of the product. Typically, if uncontrolled aerosolization occurs, the amplicon will contaminate laboratory reagents, equipment, and ventilation systems. When this happens, all reactions will be positive, and it is not possible to distinguish between amplified products from the contamination or a true, positive sample. In addition to taking precautions to avoid or control this carry-over of old products, preferred embodiments include a blank reference reaction in every PCR experiment to check for carry-over. For example, carry-over contamination will be visible on the agarose gel as faint bands or fluorescent signal when TaqMan® probes, MolBeacons, or intercalating dyes, among others, are employed as detection mechanisms. Furthermore, it is preferred to include a positive sample. As an example, in some embodiments, contamination control is performed using any of the approaches and methods described in WO 2012/054639. In some embodiments, a bleach solution is used to neutralize potential amplicons, for example, in a reaction tube of a T2Dx® device being used to perform a method of the invention. In some embodiments, contamination control includes the use of ethylene oxide (EtO) treatment, for example, of cartridge components.

Typically, the instrumentation and processing areas for samples that undergo amplification are split into pre- and post-amplification zones. This minimizes the chances of contamination of samples with amplicon prior to amplification. For example, the T2Dx® instrument design is such that the pre- and post-amplification instrumentation and processing areas are integrated into a single instrument. This is made possible as described in the sections below.

Systems

The invention provides systems for carrying out the methods of the invention, which may include one or more NMR units, MAA units, cartridge units, and agitation units, as described in WO 2012/054639. Such systems may further include other components for carrying out an automated assay of the invention, such as a thermocycling unit for the amplification of oligonucleotides; a centrifuge, a robotic arm for delivery an liquid sample from unit to unit within the system; one or more incubation units; a fluid transfer unit (i.e., pipetting device) for combining assay reagents and a biological sample (e.g., a biological sample containing cells and/or cell debris including but not limited to blood (e.g., whole blood, a crude whole blood lysate, serum, or plasma), bloody fluids (e.g., wound exudate, phlegm, bile, and the like), tissue samples (e.g., tissue biopsies, including homogenized tissue samples), or sputum) to form the liquid sample; a computer with a programmable processor for storing data, processing data, and for controlling the activation and deactivation of the various units according to a one or more preset protocols; and a cartridge insertion system for delivering pre-filled cartridges to the system, optionally with instructions to the computer identifying the reagents and protocol to be used in conjunction with the cartridge. FIG. 42 of WO 2012/054639 depicts an exemplary system of the invention.

The systems of the invention can provide an effective means for high throughput and real-time detection of analytes present in a bodily fluid from a subject. The detection methods may be used in a wide variety of circumstances including, without limitation, identification and/or quantification of analytes that are associated with specific biological processes, physiological conditions, disorders or stages of disorders. As such, the systems have a broad spectrum of utility in, for example, disease diagnosis, parental and forensic identification, disease onset and recurrence, individual response to treatment versus population bases, and monitoring of therapy. The devices and systems can provide a flexible system for personalized medicine. The system of the invention can be changed or interchanged along with a protocol or instructions to a programmable processor of the system to perform a wide variety of assays as described herein. The systems of the invention offer many advantages of a laboratory setting contained in a desk-top or smaller size automated instrument.

The systems of the invention can be used to simultaneously assay analytes that are present in the same liquid sample over a wide concentration range, and can be used to monitor the rate of change of an analyte concentration and/or or concentration of PD or PK markers over a period of time in a single subject, or used for performing trend analysis on the concentration, or markers of PD, or PK, whether they are concentrations of drugs or their metabolites. Thus, the data generated with the use of the subject fluidic devices and systems can be utilized for performing a trend analysis on the concentration of an analyte in a subject.

For example, a subject (e.g., a patient having or suspected of having a disease caused by or associated with a microbial pathogen) may be provided with a plurality of cartridge units to be used for detecting a variety of analytes, such as analytes sampled from different tissues, and at predetermined times. A subject may, for example, use different cartridge units on different days of the week. In some embodiments the software on the system is designed to recognize an identifier on the cartridge instructing the system computer to run a particular protocol for running the assay and/or processing the data. The protocols on the system can be updated through an external interface, such as an USB drive or an Ethernet connection, or in some embodiments the entire protocol can be recorded in the barcode attached to the cartridge. The protocol can be optimized as needed by prompting the user for various inputs (i.e., for changing the dilution of the sample, the amount of reagent provided to the liquid sample, altering an incubation time or MAA time, or altering the NMR relaxation collection parameters).

A multiplexed assay can be performed using a variety of system designs. For example, a multiplexed assay can performed using any of the following configurations:

(i) a spatially-based detection array can be used to direct magnetic particles to a particular region of a tube (i.e., without aggregation) and immobilize the particles in different locations according to the particular analyte being detected. The immobilized particles are detected by monitoring their local effect on the relaxation effect at the site of immobilization. The particles can be spatially separated by gravimetric separation in flow (i.e., larger particles settling faster along with a slow flow perpendicular to gravity to provide spatial separation based on particle size with different magnetic particle size populations being labeled with different targets). Alternatively, of capture probes can be used to locate magnetic particles in a particular region of a tube (i.e., without aggregation) and immobilize the particles in different locations (i.e., on a functionalized surface, foam, or gel). Optionally, the array is flow through system with multiple coils and magnets, each coil being a separate detector that has the appropriate particles immobilized within it, and the presence of the analyte detected with signal changes arising from clustering in the presence of the analyte. Optionally, once the particles are spatially separated, each individual analyte in the multiplexed assay can be detected by sliding a coil across the sample to read out the now spatially separated particles.

(ii) A microfluidic tube where the sample is physically split amongst many branches and a separate signal is detected in each branch, each branch configured for detection of a separate analyte in the multiplexed assay.

(iii) An array of 96 wells (or less or more) where each well has its own coil and magnet, and each well is configured for detection of a separate analyte in the multiplexed assay.

(iv) A sipper or flow through device with multiple independently addressable coils inside one magnet or inside multiple mini magnets that can be used for sequential readings, each reading being a separate reaction for detection of a separate analyte in the multiplexed assay.

(v) A sipper or flow through device with multiple independently addressable wells on a plate inside one magnet or inside multiple mini magnets that can be used for sequential readings using a single sided coil that can be traversed along the plate, each reading being a separate reaction for detection of a separate analyte in the multiplexed assay.

(vi) A tube containing two compartments read simultaneously, resulting in one relaxation curve which is then fit using bi-exponential fitting to produce the separate readings for the multiplexed array.

(vii) A microfluidics system where each droplet of liquid is moved around individually, to produce readings for the multiplexed array.

(viii) Sequential measurements using magnetic separation and resuspension requires novel binding probes or the ability to turn them on and off. This method would be used for nucleic acid analytes in which turn on/off mechanism is based mostly on melting temperature (at higher temperatures hairpin loops relax, denaturation of double strand binding), and hybridization will occur at different temperatures.

(ix) Individual capillaries, each equipped with dried particles within them, allow for small volume rapid multiplexing of one small aliquot. The dried particles are spatially separated, and this spatial separation permits the MR Reader to read each capillary tube independently.

(x) Binding moieties conjugated to nanoparticles are placed in a gel or other viscous material forming a region and analyte specific viscous solution. The gel or viscous solution enhances spatial separation of more than one analyte in the starting sample because after the sample is allowed to interact with the gel, the target analyte can readily diffuse through the gel and specifically bind to a conjugated moiety on the gel or viscous solution held nanoparticle. The clustering or aggregation of the specific analyte, optionally enhanced via one of the described magnetic assisted agglomeration methods, and detection of analyte specific clusters can be performed by using a specific location NMR reader. In this way a spatial array of nanoparticles, and can be designed, for example, as a 2d array.

(xi) Magnetic particles can be spotted and dried into multiple locations in a tube and then each location measured separately. For example, one type of particle can be bound to a surface and a second particle suspended in solution, both of which hybridize to the analyte to be detected. Clusters can be formed at the surface where hybridization reactions occur, each surface being separately detectable.

(xii) A spotted array of nucleic acids can be created within a sample tube, each configured to hybridize to a first portion of an array of target nucleic acids. Magnetic particles can be designed with probes to hybridize to a second portion of the target nucleic acid. Each location can be measured separately. Alternatively, any generic beacon or detection method could be used to produce output from the nucleic acid array.

(xiii) An array of magnetic particles for detecting an array of targets can be included in a single sample, each configured (e.g., by size, or relaxation properties) to provide a distinct NMR relaxation signature with aggregate formation. For example, each of the particles can be selected to produce distinct $T_2$ relaxation times (e.g., one set of particles covers 10-200 ms, a second set from 250-500 ms, a third set from 550-1100 ms, and so on). Each can be measured as a separate band of relaxation rates.

(xiv) For detection of analytes of various size or magnetic particles, or aggregates of various size, a single sample with multiple analytes and magnetic particles can undergo separation in the presence of a magnetic or electric field (i.e., electrophoretic separation of magnetic particles coated with analytes), the separate magnetic particles and/or aggregates reaching the site of a detector at different times, accordingly.

(xv) The detection tube could be separated into two (or more) chambers that each contain a different nanoparticle for detection. The tube could be read using the reader and through fitting a multiple exponential curve such as A*exp ($T_2\_1$)+B*exp($T_2\_2$), the response of each analyte could be determined by looking at the relative size of the constants A and B and $T_2\_1$ and $T_2\_2$.

(xvi) Gradient magnetic fields can be shimmed to form narrow fields. Shim pulses or other RF based shimming within a specific field can be performed to pulse and receive signals within a specific region. In this way one could envision a stratification of the RF pulse within a shim and specific resonance signals could be received from the specific shim. While this method relies on shimming the gradient magnetic field, multiplexing would include then, to rely on one of the other methods described to get different nanoparticles and the clusters to reside in these different shims. Thus there would be two dimensions, one provided by magnetic field shims and a second dimension provided by varying nanoparticle binding to more than one analyte. Nanoparticles having two distinct NMR relaxation signals upon clustering with an analyte may be employed in a multiplexed assay. In this method, the observation that small particles (30-200 nm) cause a decrease in $T_2$ with clustering whereas large particles (>800 nm) cause an increase with clustering. The reaction assay is designed as a competitive reaction, so that with the addition of the target it changes the equilibrium relaxation signal. For example, if the $T_2$ relaxation time is shorter, clusters forming of analyte with small particles are forming. If on the other hand, the $T_2$ relaxation becomes longer, clusters of analyte with larger particles are forming. It's probably useful to change the density/viscosity of the solution with additives such as trehalose or glucose or glycerol to make sure the big particles stay in solution. One nanoparticle having binding moieties to a specific analyte for whose $T_2$ signal is decreased on clustering may be combined with a second nanoparticle having a second binding moiety to a second analyte for whose $T_2$ signal is increased on clustering. In the case for which the sample is suspected to have both analytes and the clustering reaction may cancel each other out (the increased clustering cancels the decreased clustering), one could envision an ordering of the analysis, i.e. addition of competitive binding agents to detect a competitive binding and thus $T_2$ signal that would be related to the presence/absence of the analyte of interest in the sample. Alternatively, if the increased clustering cancels the decreased clustering in this multiplexing format, one could envision use of different relaxation pulse sequences or relaxation determinants to identify the presence/absence or concentration of analyte in the sample.

(xvii) Precipitation measurement of particles. In this method, multiple types of particles designed to capture different target sequences of nucleic acid are designed so that the particle size is small enough that the particles bound with analyte remain suspended in solution. Sequential addition of an "initiator" sequence that is complementary to a nucleic acid sequence conjugated to a second set of particles (a larger particle, not necessarily having magnetic properties) and contains a complementary sequence to the captured target DNA sequence. After hybridization, clusters will form if the target DNA sequence is present, e.g. the magnetic nanoparticle conjugated with probe anneals to one specific sequence on the target analyte and the other particle binds to another sequence on the target nucleic acid sequence. These clusters will be big enough to precipitate (this step may require a centrifugation step). In the same reaction, and simultaneously, one could design an additional magnetic particle, second particle set to anneal with a second nucleic acid sequence for which formation of the magnetic nanoparticle-analyte-second particle clusters do not precipitate. In this way sequential addition of particles can result in differential signaling.

(xvii) One possible different detection technique includes phase separated signals, which would stem from differing RF coil pulse sequences that are optimized for the conjugated nanoparticle-analyte interaction. Optimally, this could be achieved with multiple coils in an array that would optimize the ability of the different RF pulses and relaxation signal detection to be mapped and differentiated to ascertain the presence/absence of more than one analyte. Multiplexing may also employ the unique characteristic of the nanoparticle-analyte clustering reaction and subsequent detection of water solvent in the sample, the ability of the clusters to form various "pockets" and these coordinated clusters to have varying porosity. For example, linkers having varying length or conformational structures can be employed to conjugate the binding moiety to the magnetic nanoparticle. In this way, more than one type of cluster formed in the presence of an analyte could be designed having the ability of differing solvent water flow, and thus relaxation signal differences, through the aggregated nanoparticle-analyte-nanoparticle formation. In this way, two or more linker/binding moiety designs would then allow for detection of more than one analyte in the same sample.

(xviii) The methods of the invention can include a fluorinated oil/aqueous mixture for capturing particles in an emulsion. In this design one hydrophobic capture particle set and an aqueous capture set are used, the hydrophobic capture particle set is designed to bind and aggregate more readily in an hydrophobic environment, whereas the aqueous capture particle set is designed to bind and aggregate in an aqueous environment. Introduction of an analyte containing sample having specific analytes that will bind to either the hydrophobic or aqueous particle, and subsequent mixing in the detection tube having both hydrophobic and aqueous solvents, binding and clustering would then result in a physical separation of analytes to either the aqueous or hydrophobic phase. The relaxation signal could be detected in either solution phase. In the event that the analytes and nanoparticles designed in this manner are physically found in an emulsion created by the mixing of the hydrophobic/aqueous phases, relaxation curves would be distinguishable in the emulsion phase. The detection tube may have a capsular design to enhance the ability to move the capsules through an MR detector to read out the signal. Further, additional use of a fluorescent tag to read out probe identity may be employed, i.e. in the case of two different analytes in the same aqueous or hydrophobic phase, the addition of a fluorescent tag can assist determination of the identity of the analyte. This method is amenable in samples for which limited isolation or purification of the target analyte away from the other material in the sample because the described resonance signals are independent of sample quality. Further, the addition of the fluorescent tag can be added in much higher concentrations that usually added in typical fluorescent studies because these tags will never interfere with the relaxation measurements. In this method, oligonucleotide capture probes that are conjugated to the magnetic nanoparticles are designed so that specific restriction endonuclease sites are located within the annealed section. After hybridization with the sample forming nanoparticle-analyte clusters, a relaxation measurement then provides a base signal. Introduction of a specific restriction endonuclease to the detection tube and incubation will result in a specific reduction of the nanoparticle/analyte cluster after restriction digestion has occurred. After a subsequent relaxation measurement, the pattern of signal and restriction enzyme digestion, one can deduce the target.

(xix) In a combined method, a magnetic nanoparticle is conjugated with two separate and distinct binding moieties, i.e. an oligonucleotide and an antibody. This nanoparticle when incubated with a sample having both types of analytes in the sample will form nanoparticle-analyte complexes, and a baseline $T_2$ relaxation signal will be detectable. Subsequent addition of a known concentration of one of the analytes can be added to reduce the clustering formed by that specific analyte from the sample. After known analyte addition a subsequent $T_2$ relaxation signal is detected and the presence/absence of the sample analyte can be surmised. Further, a second analyte can be added to compete with the analyte in the sample to form clusters. Again, after a subsequent $T_2$ relaxation signal detection the presence/absence of the second sample analyte can be surmised. This can be repeated.

Broadly, a multiplexed assay employing the methods of this invention can be designed so that the use of one non-superparamagnetic nanoparticle to generate clusters with analyte from a sample, will reduce the overall $Fe^{2+}$ in assay detection vessel and will extend the dynamic range so that multiple reactions can be measured in the same detection vessel.

Multiplexing nucleic acid detection can make use of differing hybridization qualities of the conjugated magnetic nanoparticle and the target nucleic acid analyte. For example, capture probes conjugated to magnetic nanoparticles can be designed so that annealing the magnetic nanoparticle to the target nucleic acid sequence is different for more than one nucleic acid target sequence. Factors for the design of these different probe-target sequences include G-C content (time to form hybrids), varying salt concentration, hybridization temperatures, and/or combinations of these factors. This method then would entail allowing various nucleic acid conjugated magnetic nanoparticles to interact with a sample suspected of having more than one target nucleic acid analyte. Relaxation times detected after various treatments, i.e. heating, addition of salt, hybridization timing, would allow for the ability to surmise which suspected nucleic acid sequence is present or absent in the sample.

Use complimentary amplicons to block one reaction and allow serial hybridizations. In this method, universal amplification primers are used to amplify more than one specific nucleic acid sequence in the starting sample, forming an amplicon pool. Specific oligonucleotides conjugated to magnetic nanoparticles are added to the sample and a relaxation measurement is taken. The sample is then exposed to a temperature to melt the oligonucleotide-analyte interaction and addition of an oligonucleotide that is not attached to a magnetic nanoparticle is added to compete away any analyte binding to the magnetic nanoparticle. A second magnetic nanoparticle having a second oligonucleotide conjugated to it is then added to form clusters with a second specific target nucleic acid analyte. Alternatively, the method could have a step prior to the addition of the second magnetic nanoparticle that would effectively sequester the first magnetic nanoparticle from the reaction vessel, i.e. exposing the reaction vessel to a magnetic field to move the particles to an area that would not be available to the second, or subsequent reaction.

Each of the multiplexing methods above can employ a step of freezing the sample to slow diffusion and clustering time and thus alter the measurement of the relaxation time. Slowing the diffusion and clustering of the method may enhance the ability to separate and detect more than one relaxation time. Each of the multiplexing methods above can make use of sequential addition of conjugated nanoparticles followed by relaxation detection after each addition. After each sequential addition, the subsequent relaxation baseline becomes the new baseline from the last addition and can be used to assist in correlating the relaxation time with presence/absence of the analyte or analyte concentration in the sample.

In some embodiments, the method of multiplexing may involve hidden capture probes. In this method of multiplexing, oligonucleotides conjugated to the magnetic nanoparticles are designed so that secondary structure or a complementary probe on the surface of the particle hides or covers the sequence for hybridization initially in the reaction vessel. These hidden hybridization sequences are then exposed or revealed in the sample vessel spatially or temporally during the assay. For example, as mentioned above, hybridization can be affected by salt, temperature and time to hybridize. Thus, in one form of this method, secondary or complementary structures on the oligonucleotide probe conjugated to the magnetic nanoparticle can be reduced or relaxed to then expose or reveal the sequence to hybridize to the target nucleic acid sample. Further, secondary structures could be reduced or relaxed using a chemical compound, e.g., DMSO. Another method to selectively reveal or expose a sequence for hybridization of the oligonucleotide conjugated nanoparticle with the target analyte is to design stem-loop structures having a site for a restriction endonuclease; subsequent digestion with a restriction endonuclease would relax the stem-loop structure and allow for hybridization to occur. Alternatively, a chemical cut of the stem-loop structure, releasing one end could make the sequence free to then hybridize to the target nucleic acid sequence.

Where the multiplexed array is configured to detect a target nucleic acid, the assay can include a multiplexed PCR to generate different amplicons and then serially detect the different reactions.

The multiplexed assay optionally includes a logical array in which the targets are set up by binary search to reduce the number of assays required (e.g., gram positive or negative leads to different species based tests that only would be conducted for one group or the other).

The systems of the invention can run a variety of assays, regardless of the analyte being detected from a bodily fluid sample. A protocol dependent on the identity of the cartridge unit being used can be stored on the system computer. In some embodiments, the cartridge unit has an identifier (ID) that is detected or read by the system computer, or a bar code (1D or 2D) on a card that then supplies assay specific or patient or subject specific information needed to be tracked or accessed with the analysis information (e.g., calibration curves, protocols, previous analyte concentrations or levels). Where desired, the cartridge unit identifier is used to select a protocol stored on the system computer, or to identify the location of various assay reagents in the cartridge unit. The protocol to be run on the system may include instructions to the controller of the system to perform the protocol, including but not limited to a particular assay to be run and a detection method to be performed. Once the assay is performed by the system, data indicative of an analyte in the biological sample (e.g., whole blood, crude whole blood lysate, serum, or plasma) is generated and communicated to a communications assembly, where it can either be transmitted to the external device for processing, including without limitation, calculation of the analyte concentration in the sample, or processed by the system computer and the result presented on a display readout.

For example, the identifier may be a bar code identifier with a series of black and white lines, which can be read by a bar code reader (or another type of detector) upon insertion of the cartridge unit. Other identifiers could be used, such as a series of alphanumerical values, colors, raised bumps, RFID, or any other identifier which can be located on a cartridge unit and be detected or read by the system computer. The detector may also be an LED that emits light which can interact with an identifier which reflects light and is measured by the system computer to determine the identity of a particular cartridge unit. In some embodiments, the system includes a storage or memory device with the cartridge unit or the detector for transmitting information to the system computer.

Thus, the systems of the invention can include an operating program to carry out different assays, and cartridges encoded to: (i) report to the operating program which pre-programmed assay was being employed; (ii) report to the operating program the configuration of the cartridges; (iii) inform the operating system the order of steps for carrying out the assay; (iv) inform the system which pre-programmed routine to employ; (v) prompt input from the user with respect to certain assay variables; (vi) record a patient identification number (the patient identification number can also be included on the VACUTAINER® holding the blood sample); (vii) record certain cartridge information (e.g., lot number, calibration data, assays on the cartridge, analytic data range, expiration date, storage requirements, acceptable sample specifics); or (viii) report to the operating program assay upgrades or revisions (i.e., so that newer versions of the assay would occur on cartridge upgrades only and not to the larger, more costly system).

The systems of the invention can include one or more fluid transfer units configured to adhere to a robotic arm (see, e.g., FIGS. 43A-43C of WO 2012/054639). The fluid transfer unit can be a pipette, such as an air-displacement, liquid backed, or syringe pipette. For example, a fluid transfer unit can further include a motor in communication with a programmable processor of the system computer and the motor can move the plurality of heads based on a protocol from the programmable processor. Thus, the programmable processor of a system can include instructions or commands and can operate a fluid transfer unit according to the instructions to transfer liquid samples by either withdrawing (for drawing liquid in) or extending (for expelling liquid) a piston into a closed air space. Both the volume of air moved and the speed of movement can be precisely controlled, for example, by the programmable processor. Mixing of samples (or reagents) with diluents (or other reagents) can be achieved by aspirating components to be mixed into a common tube and then repeatedly aspirating a significant fraction of the combined liquid volume up and down into a tip. Dissolution of reagents dried into a tube can be done is similar fashion.

A system can include one or more incubation units for heating the liquid sample and/or for control of the assay temperature. Heat can be used in the incubation step of an assay reaction to promote the reaction and shorten the duration necessary for the incubation step. A system can include a heating block configured to receive a liquid sample for a predetermined time at a predetermined temperature. The heating block can be configured to receive a plurality of samples.

The system temperature can be carefully regulated. For example, the system includes a casing kept at a predetermined temperature (e.g., 37° C.) using stirred temperature controlled air. Waste heat from each of the units will exceed what can be passively dissipated by simple enclosure by conduction and convection to air. To eliminate waste heat, the system can include two compartments separated by an insulated floor. The upper compartment includes those portions of the components needed for the manipulation and measurement of the liquid samples, while the lower compartment includes the heat generating elements of the individual units (e.g., the motor for the centrifuge, the motors for the agitation units, the electronics for each of the separate units, and the heating blocks for the incubation units). The lower floor is then vented and forced air cooling is used to carry heat away from the system. See, e.g., FIGS. 44A and 44B of WO 2012/054639.

The MR unit may require more closely controlled temperature (e.g., ±0.1° C.), and so may optionally include a separate casing into which air heated at a predetermined temperature is blown. The casing can include an opening through which the liquid sample is inserted and removed, and out of which the heated air is allowed to escape. See, e.g., FIGS. 45A and 45B of WO 2012/054639. Other temperature control approaches may also be utilized.

Cartridge Units

The invention provides methods and systems that may involve one or more cartridge units to provide a convenient method for placing all of the assay reagents and consumables onto the system. For example, the system may be customized to perform a specific function, or adapted to perform more than one function, e.g., via changeable cartridge units containing arrays of micro wells with customized magnetic particles contained therein. The system can include a replaceable and/or interchangeable cartridge containing an array of wells pre-loaded with magnetic particles, and designed for detection and/or concentration measurement of a particular analyte. Alternatively, the system may be usable with different cartridges, each designed for detection and/or concentration measurements of different analytes, or configured with separate cartridge modules for reagent and detection for a given assay. The cartridge may be sized to facilitate insertion into and ejection from a housing for the preparation of a liquid sample which is transferred to other units in the system (e.g., a magnetic assisted agglomeration unit, or an NMR unit). The cartridge unit itself could potentially interface directly with manipulation stations as well as with the MR reader(s). The cartridge unit can be a modular cartridge having an inlet module that can be sterilized independent of the reagent module.

For handling biological samples, such as biological samples containing cells and/or cell debris including but not limited to blood (e.g., whole blood, a crude whole blood lysate, serum, or plasma), bloody fluids (e.g., wound exudate, phlegm, bile, and the like), tissue samples (e.g., tissue biopsies, including homogenized tissue samples), or sputum, there are numerous competing requirements for the cartridge design, including the need for sterility for the inlet module to prevent cross contamination and false positive test results, and the need to include reagents in the package which cannot be easily sterilized using standard terminal sterilization techniques like irradiation. An inlet module for sample aliquoting can be designed to interface with uncapped VACUTAINER® tubes, and to aliquot two a sample volume that can be used to perform, for example, an assay to detect a pathogen (see FIGS. 7D-7F of WO 2012/054639). The VACUTAINER® permits a partial or full fill. The inlet module has two hard plastic parts, that get ultrasonically welded together and foil sealed to form a network of channels to allow a flow path to form into the first well overflow to the second sample well. A soft VACUTAINER® seal part is used to for a seal with the VACUTAINER®, and includes a port for sample flow, and a venting port. To overcome the flow resistance once the VACUTAINER® is loaded and inverted, some hydrostatic pressure is needed. Every time sample is removed from a sample well, the well will get replenished by flow from the VACUTAINER®.

A modular cartridge can provide a simple means for cross contamination control during certain assays, including but not limited to distribution of amplification (e.g., PCR) products into multiple detection aliquots. In addition, a modular cartridge can be compatible with automated fluid dispensing, and provides a way to hold reagents at very small volumes for long periods of time (in excess of a year). Finally, pre-dispensing these reagents allows concentration and volumetric accuracy to be set by the manufacturing process and provides for a point of care use instrument that is more convenient as it can require much less precise pipetting.

Figure 6:
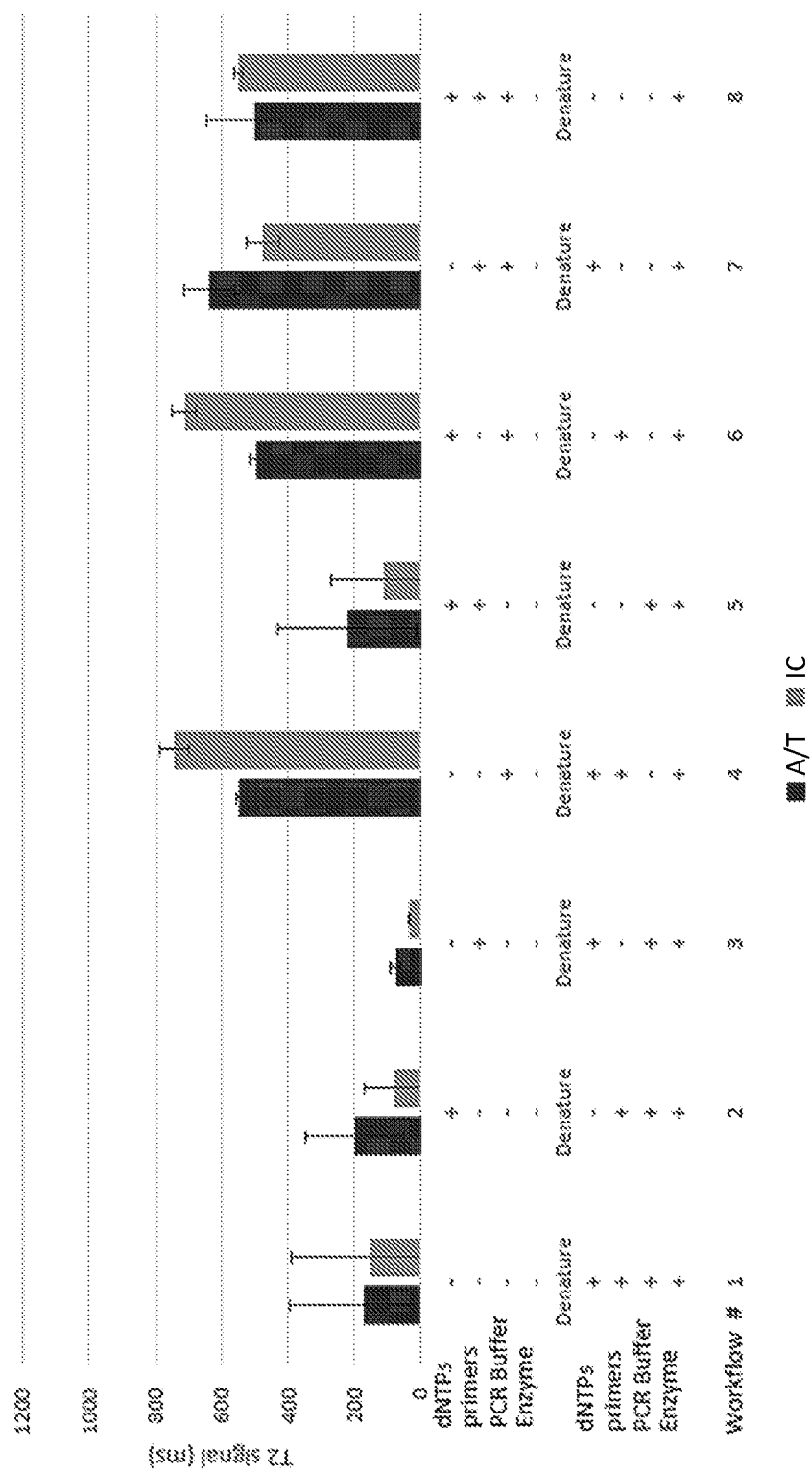
FIG. 6 is a graph showing an analysis of eight workflows with varying reagent and denaturation sequences. (n=4, "A/T" indicates *C. albicans* T2MR signal, "IC" indicates Internal Control T2MR signal).

The modular cartridge of the invention is a cartridge that is separated into modules that can be packaged and if necessary sterilized separately. They can also be handled and stored separately, if for example the reagent module requires refrigeration but the detection module does not. FIG. 6 of WO 2012/054639 shows a representative cartridge with an inlet module, a reagent module and a detection module that are snapped together. In this embodiment, the inlet module would be packaged separately in a sterile package and the reagent and detection modules would be pre-assembled and packaged together.

During storage, the reagent module could be stored in a refrigerator while the inlet module could be stored in dry storage. This provides the additional advantage that only a very small amount of refrigerator or freezer space is required to store many assays. At time of use, the operator would retrieve a detection module and open the package, potentially using sterile technique to prevent contamination with skin flora if required by the assay. The VACUTAINER® tube is then decapped and the inverted inlet module is placed onto the tube as shown in FIG. 7A of WO 2012/054639. This module has been designed to be easily moldable using single draw tooling as shown in FIGS. 7B and 7C of WO 2012/054639 and the top and bottom of the cartridge are sealed with foil to prevent contamination and also to close the channels. Once the tube has been re-sealed using the inlet module, the assembly is turned right side up and snapped onto the remainder of the cartridge. The inlet section includes a well with an overflow that allows sample tubes with between 2 and 6 ml of biological sample (e.g., blood) to be used and still provide a constant depth interface to the system automation. It accomplishes this by means of the overflow shown in FIG. 8 of WO 2012/054639, where the sample (e.g., blood) that overflows the sampling well simply falls into the cartridge body, preventing contamination.

FIGS. 9A-9C of WO 2012/054639 show the means of storing precisely pipetted small volume reagents. The reagents are kept in pipette tips that are shown in FIG. 9C of WO 2012/054639. These are filled by manufacturing automation and then are placed into the cartridge to seal their tips in tight fitting wells which are shown in a cutaway view FIG. 9B of WO 2012/054639. Finally, foil seals are placed on the back of the tips to provide a complete water vapor proof seal. It is also possible to seal the whole module with a seal that will be removed by the operator, either in place of or in addition to the aforementioned foils. This module also provides storage for empty reaction vessels and pipette tips for use by the instrument while the detection module provides storage for capped 200 µl PCR vials used by the instrument to make final measurements from.

FIGS. 10-13C of WO 2012/054639 show an alternative embodiment of the detection module of the cartridge which is design to provide for contamination control during, for example, pipetting of post-amplification (e.g., PCR) products. This is required because the billion-fold amplification produced by DNA amplification (e.g., PCR) presents a great risk of cross contamination and false positives. However, it is desirable to be able to aliquot this mixture safely, because low frequency analytes will have been amplified up and can be distributed for separate detection or identification. There are three ways in which this portion of the cartridge aids in contamination control during this aliquoting operation.

First, the cartridge contains a recessed well to perform the transfer operations in as shown in FIGS. 10A and 10B of WO 2012/054639. Second, the machine provides airflow through this well and down into the cartridge through holes in the bottom of the well, as shown in FIG. 11 of WO 2012/054639. The depth of the well is such that a pipette tip will remain in the airflow and prevent any aerosol from escaping. FIG. 12 of WO 2012/054639 depicts a bottom view of the detection module, showing the bottom of the detection tubes and the two holes used to ensure airflow. An optional filter can be inserted here to capture any liquid aerosol and prevent it from entering the machine. This filter could also be a sheet of a hydrophobic material like GORE-TEX® that will allow air but not liquids to escape. Finally, there is a special seal cap on each 200 µl tube to provide a make then break seal for each pipette tip as it enters the vessel, as shown in FIGS. 13A-13C of WO 2012/054639. It is contemplated that the pipette tip used for aliquoting be stored in this well at all, thus making it possible for the tip never to leave the controlled air flow region.

Alternatively, the modular cartridge is designed for a multiplexed assay. The challenge in multiplexing assays is combining multiple assays which have incompatible assay requirements (i.e., different incubation times and/or temperatures) on one cartridge. The cartridge format depicted in FIGS. 14A-14C of WO 2012/054639 allows for the combination of different assays with dramatically different assay requirements. The cartridge features two main components: (i) a reagent module (i.e., the reagent strip portion) that contains all of the individual reagents required for the full assay panel (for example, a panel as described below), and (ii) the detection module. In some embodiments, a cartridge may be configured to detect from 2 to 24 or more pathogens (e.g., 2, 3, 4, 5, 6, 7, 8, 9, 10, 11, 12, 13, 14, 15, 16, 17, 18, 19, 20, 21, 22, 23, 24, or more pathogens). The detection modules contain only the parts of the cartridge that carry through the incubation, and can carry single assays or several assays, as needed. The detection module depicted in FIG. 14B of WO 2012/054639 includes two detection chambers for a single assay, the first detection chamber as the control and the second detection chamber for the sample. This cartridge format is expandable in that additional assays can be added by including reagents and an additional detection module.

The operation of the module begins when the user inserts the entire or a portion of the cartridge into the instrument. The instruments performs the assay actuation, aliquoting the assays into the separate detection chambers. These individual detection chambers are then disconnected from the reagent strip and from each other, and progress through the system separately. Because the reagent module is separated and discarded, the smallest possible sample unit travels through the instrument, conserving internal instrument space. By splitting up each assay into its own unit, different incubation times and temperatures are possible as each multiplexed assay is physically removed from the others and each sample is individually manipulated.

The cartridge units of the invention can include one or more populations of magnetic particles, either as a liquid suspension or dried magnetic particles which are reconstituted prior to use. For example, the cartridge units of the invention can include a compartment including from $1\times10^6$ to $1\times10^{13}$ magnetic particles (e.g., from $1\times10^6$ to $1\times10^8$, $1\times10^7$ to $1\times10^9$, $1\times10^8$ to $1\times10^{10}$, $1\times10^9$ to $1\times10^{11}$, $1\times10^{10}$ to $1\times10^{12}$, $1\times10^{11}$ to $1\times10^{13}$, or from $1\times10^7$ to $5\times10^8$ magnetic particles) for assaying a single liquid sample.

Panels

The methods, systems, and cartridges of the invention can be configured to detect a predetermined panel of pathogens. In some embodiments, the panel may be configured to individually detect between 1 and 18 (e.g., 1, 2, 3, 4, 5, 6, 7, 8, 9, 10, 11, 12, 13, 14, 15, 16, 17, or 18) pathogens selected from the following: *Acinetobacter* spp. (e.g., *Acinetobacter baumannii, Acinetobacter pittii,* and *Acinetobacter nosocomialis*), *Enterobacteriaceae* spp., *Enterococcus* spp. (e.g., *Enterococcus faecium* (including *E. faecium* with resistance marker vanA/B) and *Enterococcus faecalis*), *Klebsiella* spp. (e.g., *Klebsiella pneumoniae* (including, e.g., *K. pneumoniae* with resistance marker KPC) and *Klebsiella oxytoca*), *Pseudomonas* spp. (e.g., *Pseudomonas aeruginosa*), *Staphylococcus* spp. (including, e.g., *Staphylococcus aureus* (e.g., *S. aureus* with resistance marker mecA), *Staphylococcus haemolyticus, Staphylococcus lugdunensis, Staphylococcus maltophilia, Staphylococcus saprophyticus,* coagulase-positive *Staphylococcus* species, and coagulase-negative (CoNS) *Staphylococcus* species), *Streptococcus* spp. (e.g., *Streptococcus mitis, Streptococcus pneumoniae, Streptococcus agalactiae, Streptococcus anginosa, Streptococcus bovis, Streptococcus dysgalactiae, Streptococcus mutans, Streptococcus sanguinis,* and *Streptococcus pyogenes*), *Escherichia* spp. (e.g., *Escherichia coli*), *Stenotrophomonas* spp. (e.g., *Stenotrophomonas maltophilia*), *Proteus* spp. (e.g., *Proteus mirabilis* and *Proteus vulgaris*), *Serratia* spp. (e.g., *Serratia marcescens*), *Citrobacter* spp. (e.g., *Citrobacter freundii* and *Citrobacter koseri*), *Haemophilus* spp. (e.g., *Haemophilus influenzae*), *Listeria* spp. (e.g., *Listeria monocytogenes*), *Neisseria* spp. (e.g., *Neisseria meningitidis*), *Bacteroides* spp. (e.g., *Bacteroides fragilis*), *Burkholderia* spp. (e.g., *Burkholderia cepacia*), *Campylobacter* (e.g., *Campylobacter jejuni* and *Campylobacter coli*), *Clostridium* spp. (e.g., *Clostridium perfringens*), *Kingella* spp. (e.g., *Kingella kingae*), *Morganella* spp. (e.g., *Morganella morgana*), *Prevotella* spp. (e.g., *Prevotella buccae, Prevotella intermedia,* and *Prevotella melaninogenica*), *Propionibacterium* spp. (e.g., *Propionibacterium acnes*), *Salmonella* spp. (e.g., *Salmonella enterica*), *Shigella* spp. (e.g., *Shigella dysenteriae* and *Shigella flexneri*), and *Enterobacter* spp. (e.g., *Enterobacter aerogenes* and *Enterobacter cloacae*), *Borrelia* spp., (e.g., *Borrelia burgdorferi* sensu lato (*Borrelia burgdorferi, Borrelia afzelii,* and *Borrelia garinii*) species), *Rickettsia* spp. (including *Rickettsia rickettsii* and *Rickettsia parkeri*), *Ehrlichia* spp. (including *Ehrlichia chaffeensis, Ehrlichia ewingii,* and *Ehrlichia muris*-like), *Coxiella* spp. (including *Coxiella burnetii*), *Anaplasma* spp. (including *Anaplasma phagocytophilum*), *Francisella* spp., (including *Francisella tularensis* (including *Francisella tularensis* subspp. *holarctica, mediasiatica,* and *novicida*)), *Streptococcus* spp. (including *Streptococcus pneumonia*), and *Neisseria* spp. (including *Neisseria meningitidis*). In some embodiments, the bacterial pathogen panel is further configured to detect a fungal pathogen, for example, *Candida* spp. (e.g., *Candida albicans, Candida guilliermondii, Candida glabrata, Candida krusei, Candida lusitaniae, Candida parapsilosis, Candida dublinensis,* and *Candida tropicalis*) and *Aspergillus* spp. (e.g., *Aspergillus fumigatus*). In some embodiments, the pathogen panel is further configured to detect a *Candida* spp. (including *Candida albicans, Candida guilliermondii, Candida glabrata, Candida krusei, Candida lusitaniae, Candida parapsilosis, Candida dublinensis,* and *Candida tropicalis*). In cases where multiple species of a genus are detected, the species may be detected using individual target nucleic acids or using target nucleic acids that are universal to all of the species, for example, target nucleic acids amplified using universal primers.

In some embodiments, the panel may be configured to individually detect one or more (e.g., 1, 2, 3, 4, 5, 6, or 7) of *Acinetobacter baumannii, Enterococcus faecium, Enterococcus faecalis, Klebsiella pneumoniae, Pseudomonas aeruginosa, Escherichia coli,* and *Staphylococcus aureus.*

In some embodiments, the panel may be configured to individually detect one or more (e.g., 1, 2, 3, 4, 5, 6, or 8) *Candida* spp. (e.g., *Candida albicans, Candida guilliermondii, Candida glabrata, Candida krusei, Candida lusitaniae, Candida parapsilosis, Candida dublinensis,* and *Candida tropicalis*).

In some embodiments, the panel can be a Lyme disease pathogen panel configured to individually detect one, two, or three *Borrelia burgdorferi* sensu lato (*Borrelia burgdorferi, Borrelia afzelii,* and *Borrelia garinii*) species. These species may be detected using individual target nucleic acids or using target nucleic acids that are universal to all three species, for example, target nucleic acids amplified using universal primers. In some embodiments, the panel is configured to detect *Borrelia burgdorferi*. In some embodiments, the panel is configured to detect *Borrelia afzelii*. In some embodiments, the panel is configured to detect *Borrelia garinii*. In some embodiments, the panel is configured to detect *Borrelia burgdorferi* and *Borrelia afzelii*. In some embodiments, the panel is configured to detect *Borrelia burgdorferi* and *Borrelia garinii*. In some embodiments, the panel is configured to detect *Borrelia afzelii* and *Borrelia garinii*. In some embodiments, the panel is configured to detect *Borrelia burgdorferi, Borrelia afzelii* and *Borrelia garinii*. In some embodiments, the panel may be configured to individually detect one or more (e.g., 1, 2, 3, 4, 5, or 6) of *Rickettsia rickettsii, Coxiella burnettii, Ehrlichia chaffeensis, Babesia microti, Francisella tularensis,* and *Anaplasma phagocytophilum.*

In any of the above embodiments, the panel may be configured to detect a marker that is characteristic of a genus, for example, a pan-bacterial marker, a pan-*Candida* marker, or a pan-*Borrelia* marker. In any of the above panels, the analyte may be a nucleic acid (e.g., an amplified target nucleic acid, as described above), or a polypeptide (e.g., a polypeptide derived from the pathogen or a pathogen-specific antibody produced by a host subject, for example, an IgM or IgG antibody). In some embodiments, multiple analytes (e.g., multiple amplicons) are used to detect a pathogen. In any of the above panels, the biological sample may be a biological sample containing cells and/or cell debris including but not limited to blood (e.g., whole blood, a crude whole blood lysate, serum, or plasma), bloody fluids (e.g., wound exudate, phlegm, bile, and the like), tissue samples (e.g., tissue biopsies, including homogenized tissue samples), or sputum. In some embodiments, the biological sample is blood (e.g., whole blood, a crude whole blood lysate, serum, or plasma). Such panels may be used, for example, to diagnose bloodstream infections. In some embodiments, the biological sample may be a tissue sample, for example, a homogenized tissue sample. Such panels may be used, for example, to detect infections present in tissue, e.g., tissue biopsies of skin at the site of a tick bite to identify *Borrelia* spp. for diagnosis of Lyme disease.

Amplifying Multiple Amplicons Characteristic of a Species for Improved Sensitivity and/or Specificity In some embodiments, the methods of the invention may involve amplification and detection of more than one amplicon characteristic of a species in a biological sample containing cells and/or cell debris including but not limited to blood (e.g., whole blood, a crude whole blood lysate, serum, or plasma), bloody fluids (e.g., wound exudate, phlegm, bile, and the like), tissue samples (e.g., tissue biopsies, including homogenized tissue samples), or sputum. In some embodiments, amplification of more than one target nucleic acid characteristic of a species increases the total amount of amplicons characteristic of the species in an assay (in other words, the amount of analyte is increased in the assay). This increase may allow, for example, an increase in sensitivity and/or specificity of detection of the species compared to a method that involves amplification and detection of a single amplicon characteristic of a species. In some embodiments, the methods of the invention may involve amplifying 2, 3, 4, 5, 6, 7, 8, 9, or 10 amplicons characteristic of a species.

In some embodiments, multiple (e.g., 2, 3, 4, 5, 6, 7, 8, 9, or 10) single-copy loci from a species are amplified and detected. In some embodiments, 2 single-copy loci from a species are amplified and detected. In some embodiments, amplification and detection of multiple single-copy loci from a species may allow for a sensitivity of detection comparable with methods that involve detecting an amplicon that is derived from a multi-copy locus. In some embodiments, methods involving detection of multiple single-copy loci amplified from a microbial species can detect from about 1-10 cells/mL (e.g., 1, 2, 3, 4, 5, 6, 7, 8, 9 or 10 cells/mL) of the microbial species in a liquid sample. In some embodiments, methods involving detection of multiple single-copy loci amplified from a microbial species have at least 95% correct detection when the microbial species is present in the liquid sample at a frequency of less than or equal to 5 cells/mL (e.g., 1, 2, 3, 4, or 5 cells/mL) of liquid sample.

The invention also provides embodiments in which at least three amplicons are produced by amplification of two target nucleic acids, each of which is characteristic of a species. For example, in some embodiments, a first target nucleic acid and a second target nucleic acid to be amplified may be separated (for example, on a chromosome or on a plasmid) by a distance ranging from about 50 base pairs to about 1000 1500 base pairs (bp), e.g., about 50, 100, 150, 200, 250, 300, 400, 500, 600, 700, 800, 900, or 1000, 1100, 1200, 1300, 1400, or 1500 bp base pairs. In some embodiments, a first target nucleic acid and a second target nucleic acid to be amplified may be separated (for example, on a chromosome or on a plasmid) by a distance ranging from about 50 bp to about 1000 bp (e.g., about 50, 100, 150, 200, 250, 300, 400, 500, 600, 700, 800, 900, or 1000 bp). In some embodiments the first target nucleic acid and the second target nucleic acid to be amplified may be separated by a distance ranging from about 50 bp to about 1500 bp, from about 50 bp to about 1400 bp, from about 50 bp to about 1300 bp, from about 50 bp to about 1200 bp, from about 50 bp to about 1100 bp, from about 50 bp to about 1000 bp, from about 50 bp to about 950 bp, from about 50 bp to about 900 bp, from about 50 bp to about 850 bp, from about 50 bp to about 800 bp, from about 50 bp to about 800 bp, from about 50 bp to about 750 bp, from about 50 bp to about 700 bp, from about 50 bp to about 650 bp, from about 50 bp to about 600 bp, from about 50 bp to about 550 bp, from about 50 bp to about 500 bp, from about 50 bp to about 500 bp, from about 50 bp to about 450 bp, from about 50 bp to about 400 bp, from about 50 bp to about 350 bp, from about 50 bp to about 300 bp, from about 50 bp to about 250 bp, from about 50 bp to about 200 bp, from about 50 bp to about 150 bp, or from about 50 bp to about 100 bp. In some embodiments, amplification of the first and second target nucleic acids using individual primer pairs (each having a forward and a reverse primer) may lead to amplification of an amplicon that includes the first target nucleic acid, an amplicon that includes the second target nucleic acid, and an amplicon that contains both the first and the second target nucleic acid. This may result in an increase in sensitivity of detection of the species compared to samples in which the third amplicon is not present. In any of the preceding embodiments, amplification may be by asymmetric PCR.

The invention provides magnetic particles decorated with nucleic acid probes to detect two or more amplicons characteristic of a species. For example, in some embodiments, the magnetic particles include two populations, wherein each population is conjugated to probes such that the magnetic particle that can operably bind each of the two or more amplicons. For instance, in embodiments where two target nucleic acids have been amplified to form a first amplicon and a second amplicon, a pair of particles each of which have a mix of capture probes on their surface may be used. In some embodiments, the first population of magnetic particles may be conjugated to a nucleic acid probe that operably binds a first segment of the first amplicon and a nucleic acid probe that operably binds a first segment of the second amplicon, and the second population of magnetic particles may be conjugated to a nucleic acid probe that operably binds a second segment of the first amplicon and a nucleic acid probe that operably binds a second segment of the second amplicon. For instance, one particle population may be conjugated with a 5' capture probe specific to the first amplicon and a 5' capture probe specific to second amplicon, and the other particle population may be conjugated with a 3' capture probe specific to the first amplicon and a 3' capture probe specific to the second amplicon.

In such embodiments, the magnetic particles may aggregate in the presence of the first amplicon and aggregate in the presence of the second amplicon. Aggregation may occur to a greater extent when both amplicons are present.

In some embodiments, a magnetic particle may be conjugated to two, three, four, five, six, seven, eight, nine, or ten nucleic acid probes, each of which operably binds a segment of a distinct target nucleic acid. In some embodiments, a magnetic particle may be conjugated to a first nucleic acid probe and a second nucleic acid probe, wherein the first nucleic acid probe operably binds to a first target nucleic acid, and the second nucleic acid probe operably binds to a second target nucleic acid. In other embodiments, a magnetic particle may be conjugated to a first nucleic acid probe that operably binds a first target nucleic acid, a second nucleic acid probe that operably binds a second target nucleic acid, and a third nucleic acid that operably binds a third target nucleic acid. In yet other embodiments, a magnetic particle may be conjugated to a first nucleic acid probe that operably binds a first target nucleic acid, a second nucleic acid probe that operably binds a second target nucleic acid, a third nucleic acid that operably binds a third target nucleic acid, and a fourth nucleic acid probe that operably binds a fourth target nucleic acid. In still other embodiments, a magnetic particle may be conjugated to a first nucleic acid probe that operably binds a first target nucleic acid, a second nucleic acid probe that operably binds a second target nucleic acid, a third nucleic acid that operably binds a third target nucleic acid, a fourth nucleic acid probe that operably binds a fourth target nucleic acid, and a fifth nucleic acid probe that operably binds a fifth target nucleic acid. In some embodiments, one population of magnetic particles includes the 5' capture probe for each amplicon to be detected, and the other population of magnetic particles includes the 3' capture probe for each amplicon to be detected.

EXAMPLES

The following examples are put forth so as to provide those of ordinary skill in the art with a complete disclosure and description of how the devices, systems, and methods described herein are performed, made, and evaluated, and are intended to be purely exemplary of the invention and are not intended to limit the scope of what the inventors regard as their invention.

Example 1: Comparison of Taq and a Mutant Thermostable DNA Polymerase

Performance of Taq polymerase (NEB) was compared to that of a mutant thermostable DNA polymerase (see, e.g., Table 2), in a 100 µl PCR reaction that contained spiked genomic DNA in TE buffer, pH 8.0. Reactions contained a final concentration of 2 genome equivalents of purified *Candida albicans* genomic DNA and 200 copies of internal control (IC). The PCR reaction buffer used included 60 mM Tricine, pH 8.7, 3.5 mM $MgCl_2$, 6% glycerol, 5 mM ammonium sulfate (final concentrations). 75-500 nM primers and 200 nM dNTPs were used. All reaction components were mixed by pipetting up and down 3 to 5 times. Thermocycling was performed as follows: 10 min at 95° C.; followed by 40 cycles of 20 sec at 95° C., 30 sec at 62° C., 30 sec at 68° C., and a final extension of 10 min at 68° C. The completed PCR reaction was diluted with 50 µl of TE, pH 8.0 and two 15 µl aliquots of the dilution were used in a *Candida albicans* (NT) and Internal Control (IC)-specific detection reaction as described by Neely et al. *Science Translational Medicine* 5(182):182ra54, 2013, which is incorporated herein by reference in its entirety.

Three concentrations of Taq were tested. A final concentration of 0.025 to 0.05 U/µl reaction (corresponding to 2.5 units to 5 units/reaction for a 100 µl reaction) is recommended by the supplier and is commonly used in published assays. The concentration was increased up to 5-fold without any detectable loss of sensitivity and specificity based on the T2MR signal value averages (FIG. 1). All three concentrations of Taq performed similarly to that of the mutant thermostable DNA polymerase in a buffer sample.

Example 2: Preparation of Bulk Crude Whole Blood Lysate 17.5 mL of whole human blood from a healthy donor was added to each of eight 50 mL FALCON™ tubes, containing 1 gram of 0.8 mm zirconium oxide beads (OPS, New Jersey). 1 mL of red blood cell lysis solution (TRAx; TRITON™ X-100/Nonidet) was added, the solution was mixed and incubated at ambient temperature for 5 min. The tubes were spun for 8 min at 3200 g at ambient temperature. The dark red supernatant was carefully removed without disturbing the slimy pellet that contains cell debris, including membranes and concentrated insoluble membrane proteins from human red and white blood cells, partially intact nuclei and mitochondria (and genomic DNA contained therein) from white blood cells, and other cell components such as heme, hemoglobin, and protein-bound ions such as iron.

1.5 mL of TE buffer, pH 8.0, containing 4 copies/µL of an Internal PCR Control (IC) fragment was added and vortexed for 1 to 2 sec. The tubes were centrifuged for 5 min at 3200 g. The supernatant was removed as described above in Example 1, leaving a red slimy pellet containing components as described above. Finally, 1 mL of TE buffer containing 4 copies/µL IC was added to the pellet and cells were lysed by vortexing 4 min on a bench top vortexer. A homogenized foamy red lysate was collected after brief centrifugation from each tube and combined. The resulting bulk crude whole blood lysate was stored frozen at −20° C.

Following this method, a total of 7 to 8 mL of crude blood lysate was obtained from a total of 140 mL of human whole blood. By this approach, 17.5 mL of blood is effectively concentrated into 1 mL of lysate, and each 50 µL experimental sample is the equivalent of 0.875 mL of whole blood. A single batch of this lysate can be used to produce 70-80 different amplification reactions. This approach can be scaled up or down.

Such a concentrated lysate is considered to contain about 2.5 to 5 mg of human DNA, which can be extracted from 140 mL of whole blood (based on an estimate of 3 to 6 million white blood cells/mL). The crude whole blood lysate is considered to contain up to 310 to 620 µg of DNA/mL. A typical PCR reaction described herein contains about 50 µl of this lysate or an equivalent thereof, i.e., about 16 to 32 µg of human DNA.

Example 3: Comparison of Commercially Available Thermostable DNA Polymerases and a Mutant Thermostable DNA Polymerase in Crude Whole Blood Lysates Performance of Taq polymerase and a mutant thermostable DNA polymerase were compared in crude whole blood lysate prepared as described in Example 2 and according to Neely et al. 2013, supra. Crude whole blood lysate has a red coloration indicating the presence of heme and hemoglobin compounds remaining in the lysate after a brief washing step. The lysate also contains human DNA at around 30-50 µg that is released from white blood cells upon mechanical lysis (see, e.g., Example 2). Further, Example 4 below demonstrates that additional free DNA eventually results in complete inhibition of the PCR reaction. Crude whole blood lysate therefore contains a high concentration of known PCR inhibitors (including DNA, heme and hemoglobin, protein bound iron, and the like) that should impact the performance of Taq polymerase.

The reaction volume of 100 µl contained 50 µl of crude whole blood lysate prepared as described in Example 2 spiked with 2 genome copy equivalents of *C. albicans* DNA and 200 copies of IC. Reaction buffer was 60 mM Tricine, pH 8.7, 3.5 mM $MgCl_2$, 6% glycerol, 5 mM ammonium sulfate (final concentrations). The reaction was prepared following a workflow as follows: 30 µl of Reagent A (which contains reaction buffer, dNTPs, and primers) was added to 50 µl of spiked crude whole blood lysate and denatured at 95° C. for 5 minutes. The resulting brown cake was centrifuged for 5 min at 12,000 g at ambient temperature. A dark brown pellet was visible with a brown/reddish supernatant on top. 20 µl of mutant thermostable DNA polymerase or Taq dilution was added and PCR and subsequent detection was performed as described in Example 1.

Figure 2:
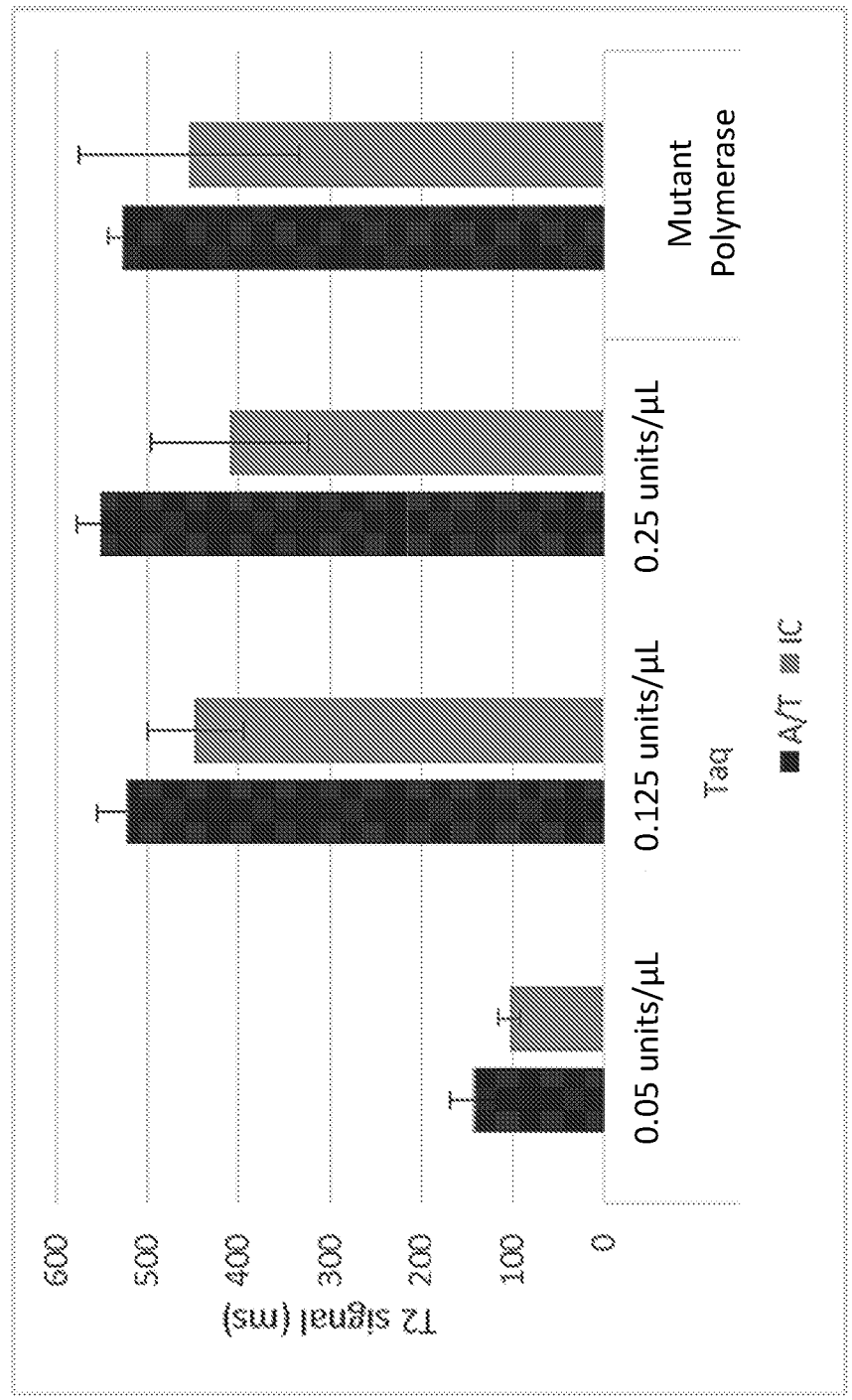
FIG. 2 is a graph showing T2MR signals (ms) obtained from A/T and IC specific amplification products synthesized by Taq or a mutant thermostable DNA polymerase in crude whole blood lysate (n=4, "A/T" indicates *C. albicans* detection, "IC" indicates Internal Control detection).

The results indicated that Taq polymerase was inhibited considerably at concentrations recommended by the manufacturer and as commonly used in published assays (FIG. 2; see, e.g., 0.05 U/µl). After raising the final concentration of Taq 5-fold (0.125 U/µl), sensitivity was comparable to that of the mutant thermostable DNA polymerase in crude blood lysate. A further increase in the concentration of Taq to 10-fold above the recommended working concentration did not result in a major change in the $T_2$ signal values (FIG. 2). This was considered unexpected because the detrimental impact of excessive polymerase on product yield due to increases in non-specific amplification products has been described in the literature (see, e.g., Innis et al. *PCR Protocols: A Guide to Methods and Applications*. Academic Pres, Waltham MA).

Figure 8:
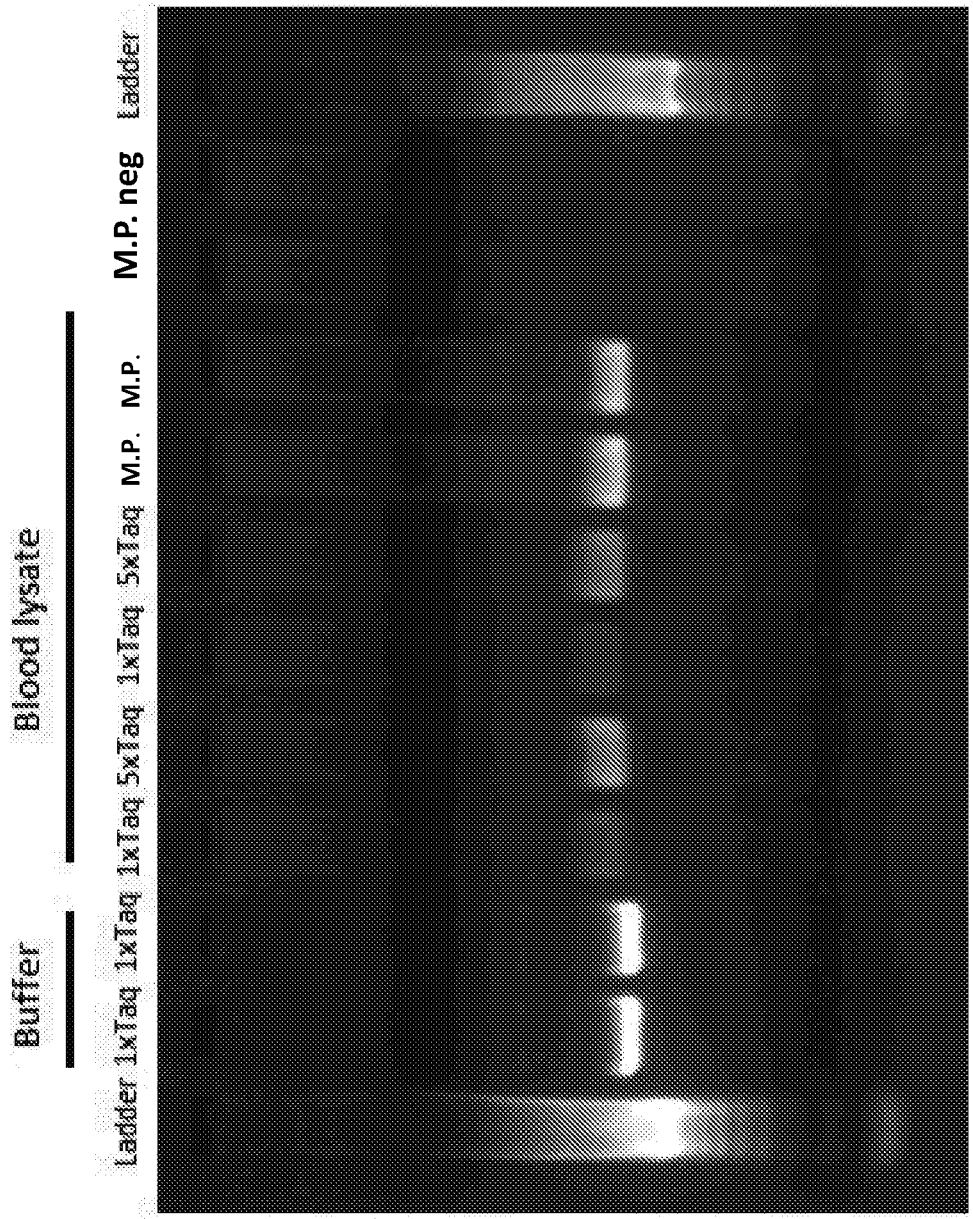
FIG. 8 is an image of an ethidium bromide-stained agarose gel showing the results of amplification using Taq or a mutant thermostable DNA polymerase ("M.P.") in a crude whole blood lysate or buffer as described in Example 3. "Neg" indicates a negative control. The ladder is used to show the relative size of amplicons.

In addition, amplicons produced by the above amplification workflow were also detected using gel electrophoresis and staining with ethidium bromide (FIG. 8). This finding demonstrates that detection approaches beyond T2MR can be used to detect amplicons produced by the workflow and reaction conditions described above.

The commercially available enzyme Hawk Z05 (Roche), a modified aptamer-based hot start DNA polymerase from *Thermus* spp. Z05, was also tested for performance in crude whole blood lysates. Each 50 µl reaction contained 25 µL of crude blood lysate (prepared as described in Example 2), spiked with 10 genome copy equivalents of *Klebsiella pneumonia* DNA. 15 µL of Reaction Buffer and primers were added followed by a denaturation step at 95° C. for 5 minutes. The resulting coagulated blood lysate was spun down at 12,000 g for 5 min. Finally, Hawk Z05 was diluted and mixed with dNTPs, and 10 µL of this mixture was added to each reaction so that the final concentration of Hawk Z05 was 0.4 U/µL (manufacturer's recommendation). Crude blood lysate reactions were compared to those containing template in TE Buffer, pH 8.0 ("Buffer" in FIG. 3). PCR and detection were performed as described in Example 1.

Figure 3:
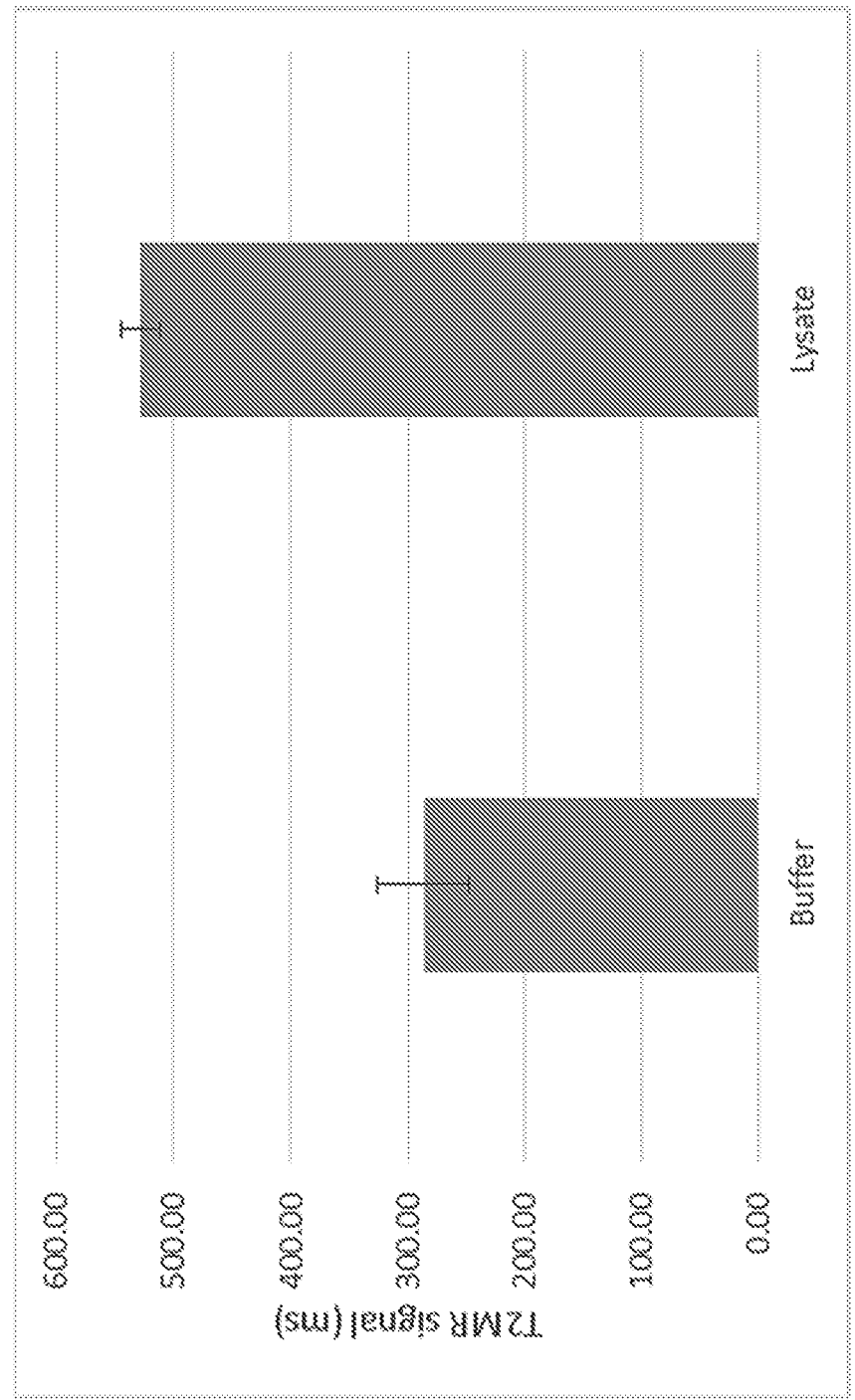
FIG. 3 is a graph showing T2MR signals (ms) obtained from *K. pneumoniae* amplification products synthesized by Hawk Z05 in spiked buffer and crude whole blood lysate (n=4).

Hawk Z05, like Taq and the mutant thermostable DNA polymerase, was capable of amplifying targets in crude blood lysates (FIG. 3). However, unlike Taq, increasing enzyme concentrations above that recommended by the manufacturer was not required. This observation may corroborate published findings that certain *Thermus* species polymerases, such as Tth, tolerate higher total blood concentrations in PCR reactions than Taq.

Example 4: Impact of Excess Non-Target DNA

Since non-target DNA, such as DNA extracted from host cells, has been determined to be an inhibitor of PCR, the effect of additional exogenous DNA was tested on the performance of Taq and a mutant thermostable DNA polymerase.

Reactions containing TE buffer or crude whole blood lysate spiked with *C. albicans* genomic DNA and IC DNA were prepared and detected as described in Examples 1 and 3, respectively. Exogenous sonicated salmon sperm DNA (Agilent) was added to reactions to evaluate the total DNA concentration that was still permissible for successful amplification (using $T_2$ signal as a readout) in buffer and crude whole blood lysate. Total endogenous DNA concentration contributed from human cells in the crude blood lysate was estimated to be approximately 16 to 32 µg per reaction (see, e.g., Example 2). Exogenous DNA additions were varied from 0 to 20 µg. Final Taq concentrations were varied 10-fold between 0.025 U/µl to 0.25 U/µl. The mutant thermostable DNA polymerase concentrations were varied from 1:1 (original final concentration as utilized in Neely et al. 2013, supra, corresponding to a 1:5 final concentration of mutant polymerase:reaction mixture) to 1:20 (corresponding to a 1:100 final concentration of mutant polymerase:reaction mixture).

Figure 4A:
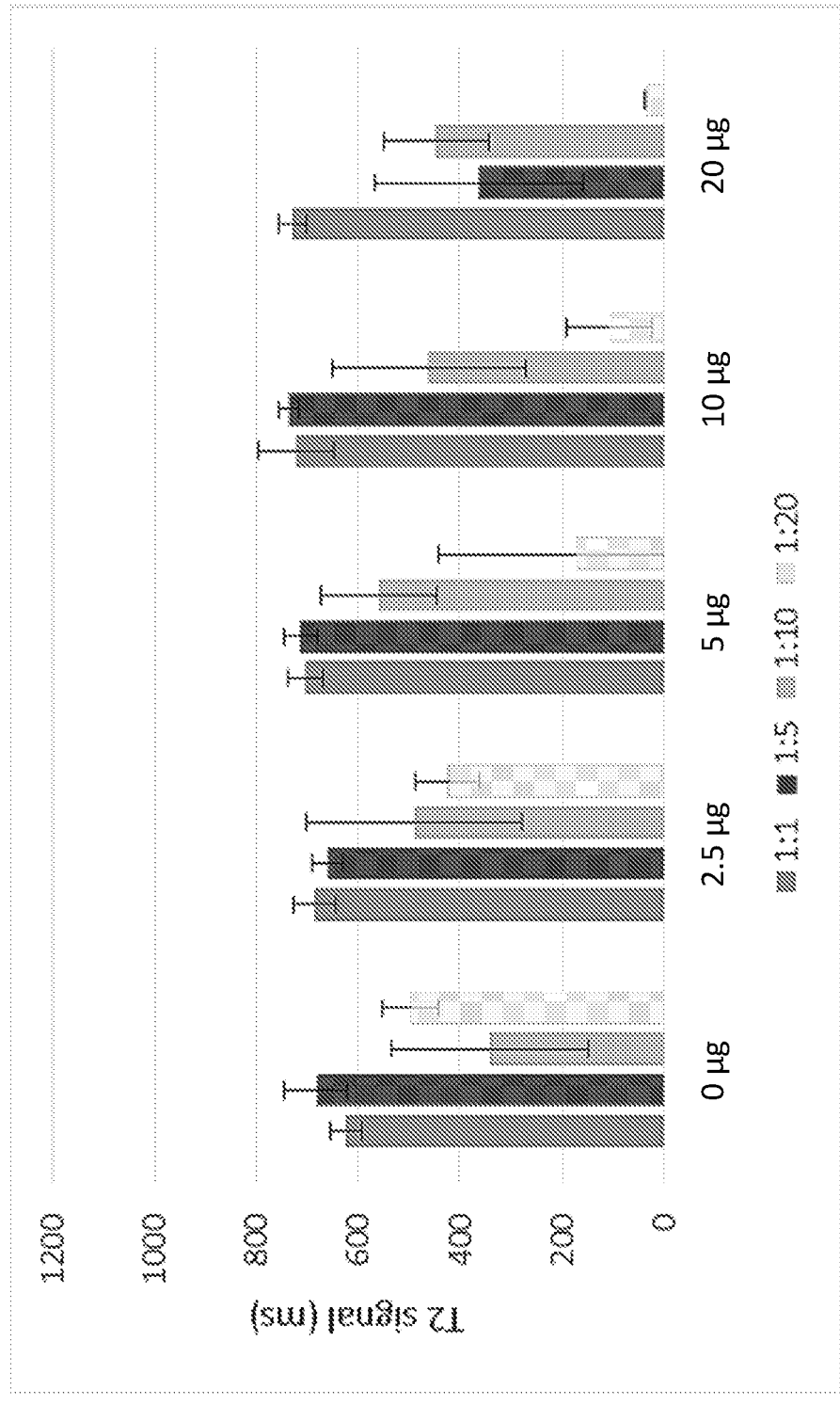
FIGS. 4A-4D are a series of graphs showing the effects of additional exogenous DNA on a mutant thermostable DNA polymerase (FIGS. 4A and 4C) and Taq (FIGS. 4B and 4D). The mutant polymerase was prepared at four dilutions (1:1, 1:5, 1:10, or 1:20) and amplification was tested in buffer (FIG. 4A) and crude whole blood lysate (FIG. 4C). For comparison, four concentrations of Taq polymerase (0.25 units/µL, 0.125 units/µL, 0.05 units/µL, or 0.025 units/µL) were used for amplification reactions in buffer (FIG. 4B) and crude whole blood lysate (FIG. 4D). Sonicated salmon sperm DNA (0 µg (control), 2.5 µg, 5 µg, 10 µg, or 20 µg) was added to reactions as indicated. The T2MR signals (ms) obtained from *C. albicans* amplicons synthesized are shown.
Figure 4B:
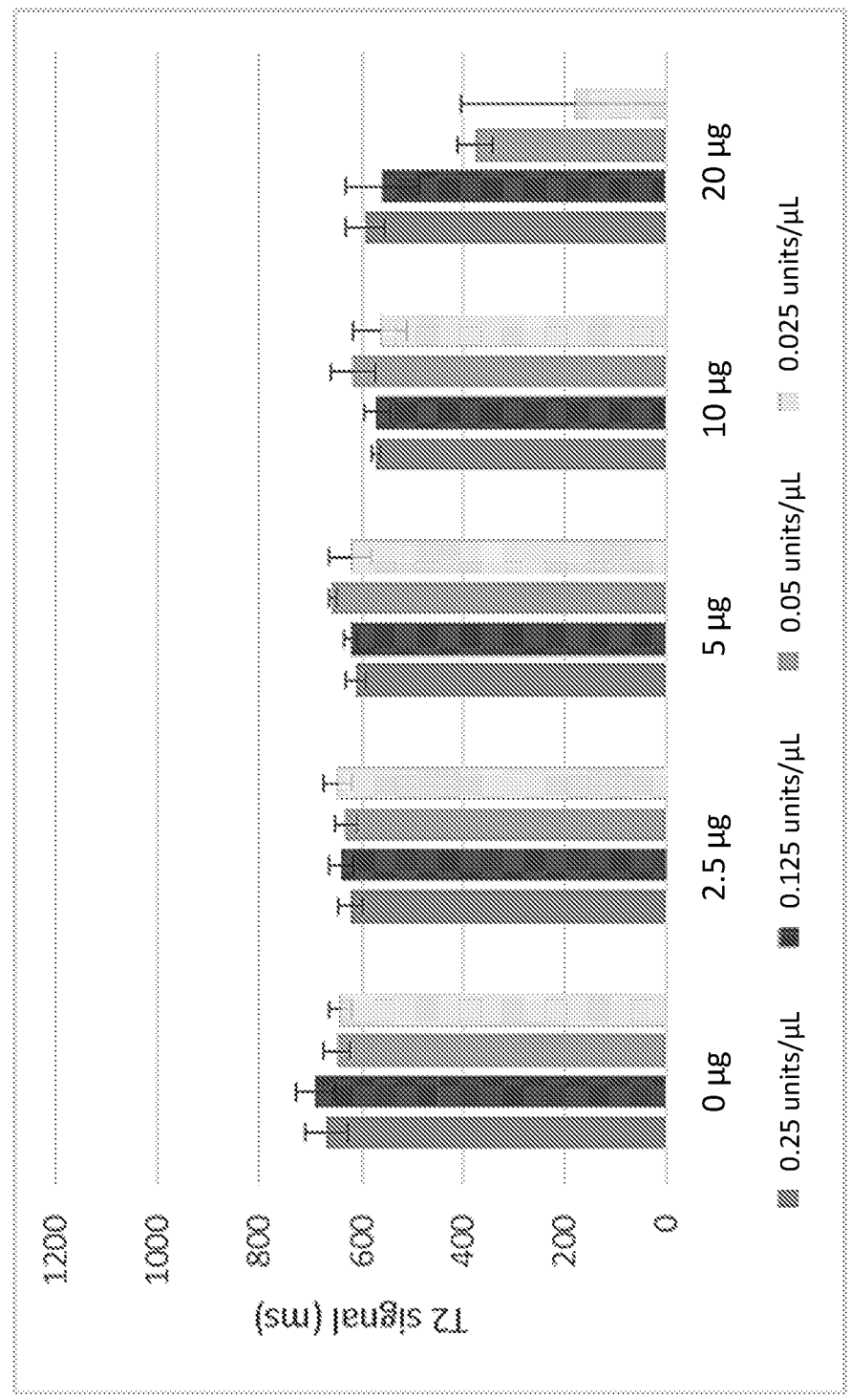
Figure 4C:
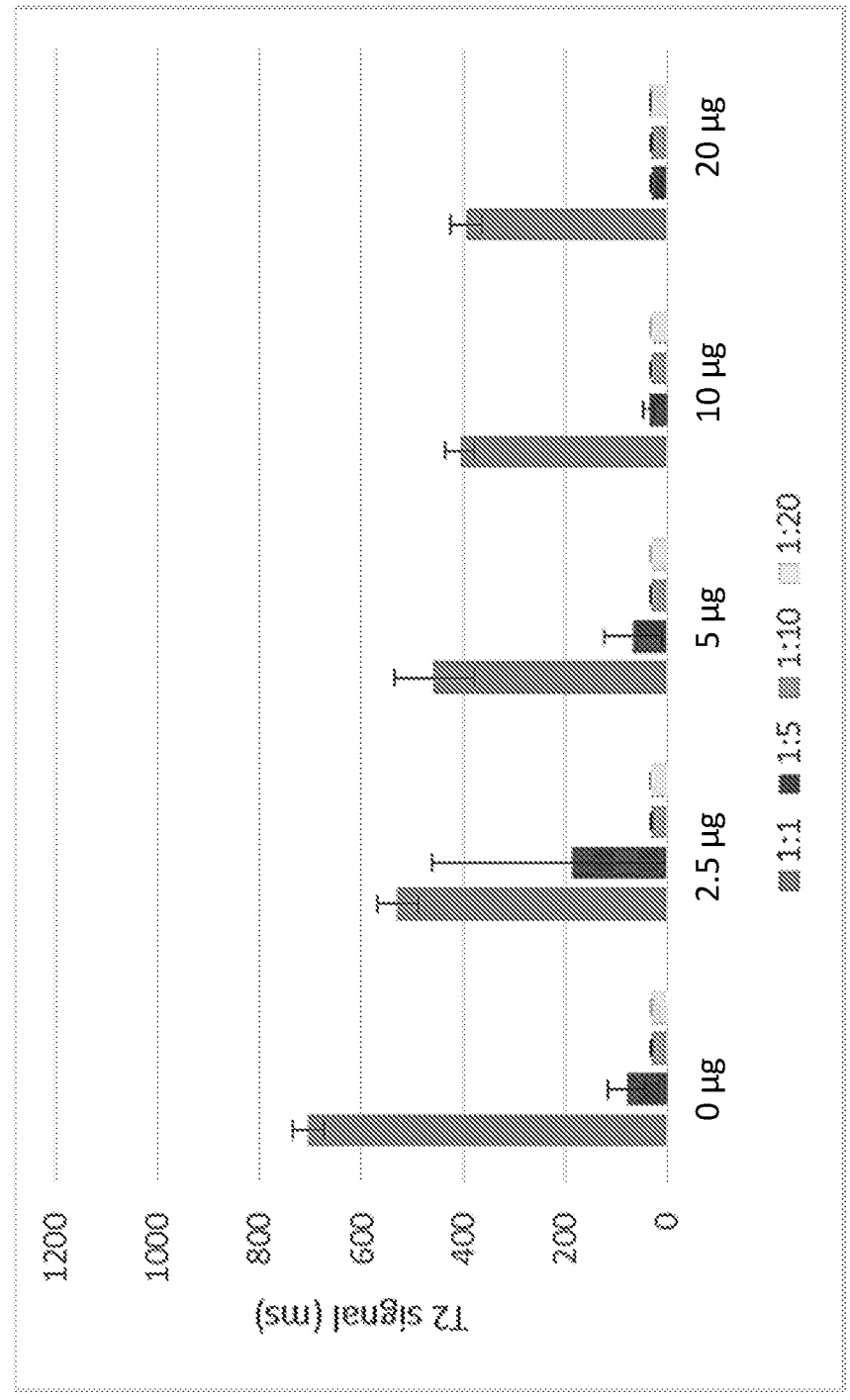

As expected, addition of exogenous DNA inhibited amplification of the *C. albicans* target, albeit at different concentrations in buffer as compared to in crude whole blood lysate (FIGS. 4A-4D). In buffer, 20 µg of salmon sperm DNA was needed to see an impact on assay sensitivity (FIGS. 4A and 4B). However, in the case of Taq, this effect was only observed at low polymerase concentrations, i.e., 0.025 U/µl, and was overcome when enzyme concentrations were increased by 2- to 5-fold (FIG. 4B). The impact of exogenous DNA addition on the mutant thermostable DNA polymerase was clear when the enzyme was present at a 1:10 dilution compared to the concentration used in Neely et al. 2013, supra (FIG. 4A). Addition of 5 µg exogenous DNA had an impact on assay sensitivity when the mutant thermostable DNA polymerase is present at a 1:5 dilution as compared to the concentration used in Neely et al. 2013, supra.

Figure 4D:
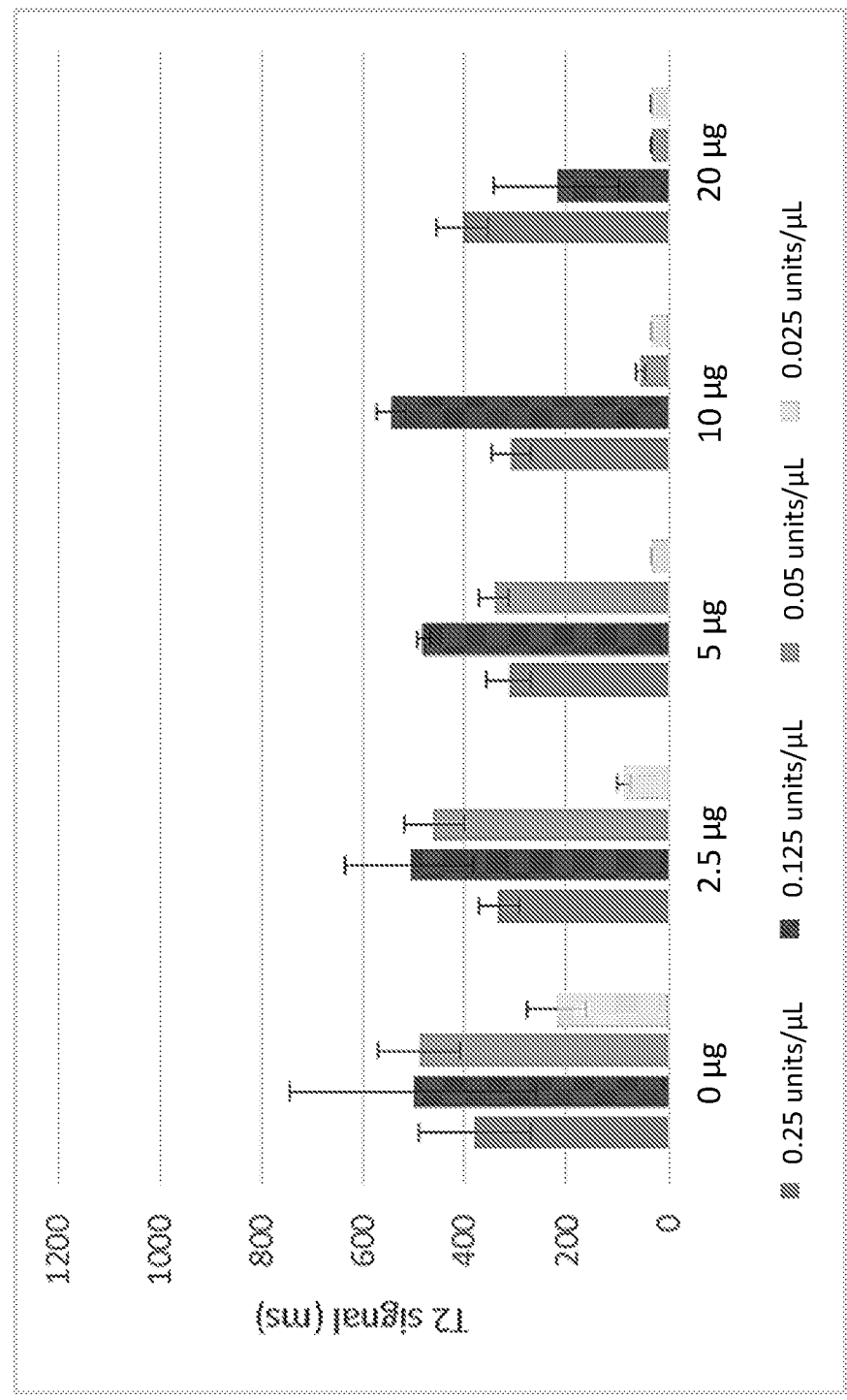

The impact of additional DNA on amplification in crude whole blood lysate was more dramatic, as the starting concentration of DNA is already high due to the endogenous DNA. In crude whole blood lysate, an addition of 2.5 µg of additional DNA resulted in a decline in sensitivity in the case of 0.125 units/µL Taq polymerase (FIG. 4D). In the case of the mutant thermostable DNA polymerase, a 1:5 dilution of mutant polymerase concentration as compared to the conditions described in Neely et al. 2013, supra resulted in almost complete inhibition of amplification in crude whole blood lysate.

The polymerases were influenced to a greater extent by addition of exogenous DNA to crude whole blood lysates compared to buffer, likely due to the high background of endogenous cellular DNA in the crude whole blood lysate as well as other inhibitors. The mechanism of DNA inhibition is likely stoichiometric since higher polymerase concentrations can resist the inhibition, i.e., form more initiation complexes, regardless of specificity, so that specific amplification is still possible. In other words, an increase in polymerase concentration is considered to counter non-specific binding/sequestering of enzyme.

Example 5: Comparison of Hot Start Thermostable DNA Polymerases

Multiplex PCR is commonly used for diagnostic assays. Hot start thermostable DNA polymerases may be used in multiplex PCR reactions. Hot start PCR avoids the formation of primer-dimer or non-specific extension at lower temperatures due to the intrinsic residual activity of Taq, Taq mutant enzymes, and other thermostable DNA polymerases. In some cases, such residual activity may completely inhibit formation of specific products since primers are used up by converting them into non-specific extension products at temperatures below annealing to specific template.

A hot start Taq/Aptamer formulation (APTATAQ™, Roche Molecular Systems) was evaluated and compared a mutant hot start thermostable DNA polymerase ("mutant HS polymerase") in a 7-plex PCR reaction that allows amplification of target nucleic acids specific for a panel of 6 bacterial species along with an Internal Control. Reactions containing 10 genome equivalents of purified *K. pneumoniae* DNA and 200 copies of IC in TE buffer were prepared as described in Example 1. Reagent B was substituted for Reagent A. Reagent B contains the reaction buffer and a seven-plex primer mix. The reactions contained either a 1× formulation of mutant HS polymerase/dNTP mix or APTATAQ™/dNTP mix concentrations varying 10-fold (0.025 U/µl to 0.25 U/µl APTATAQ™ final).

Figure 5:
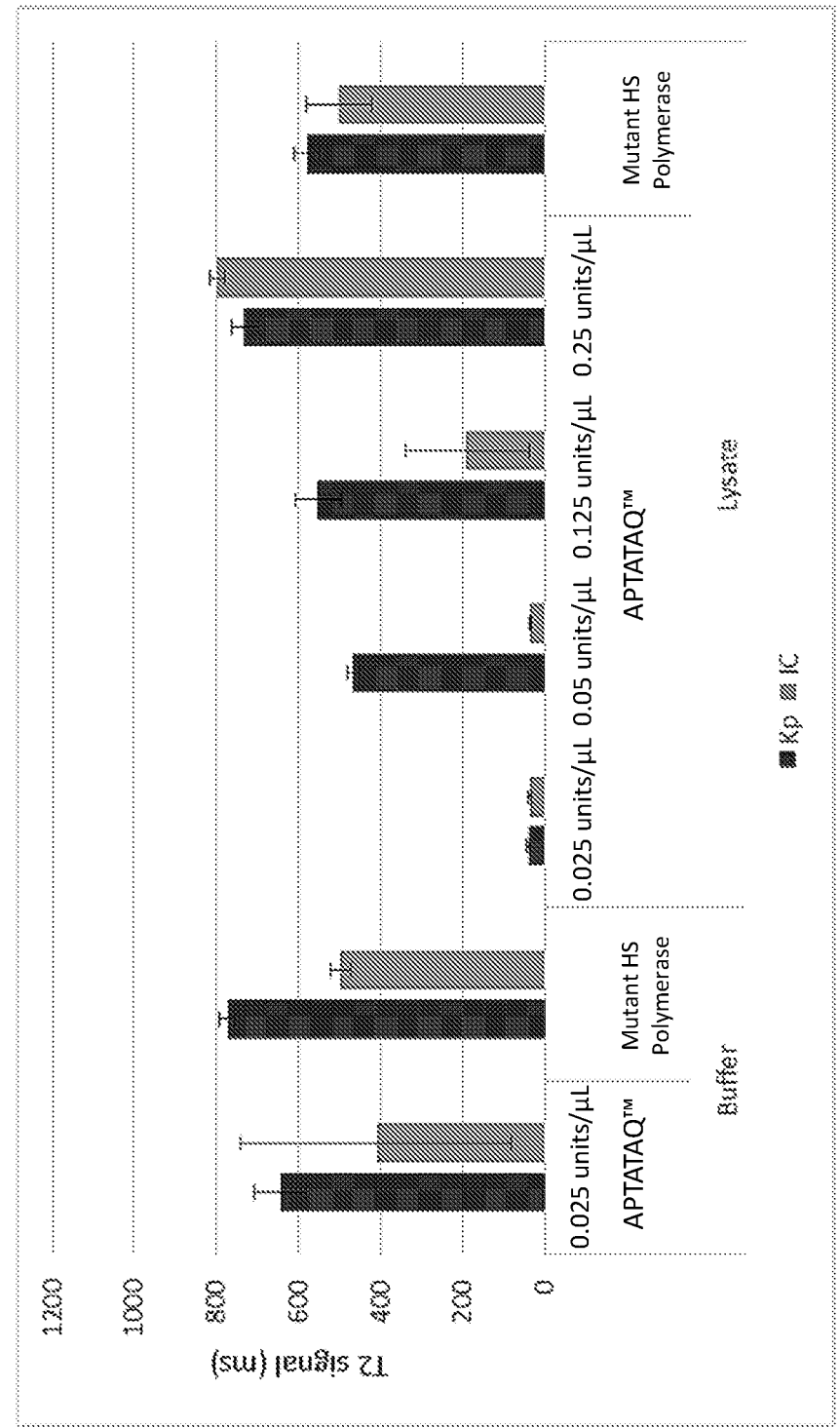
FIG. 5 is a graph showing functionality of APTATAQ™ and a mutant hot start thermostable DNA polymerase ("mutant HS polymerase") amplification in buffer (left) and crude whole blood lysates (center right) spiked with *K. pneumoniae* genomic DNA and IC. (n=4, "Kp" indicates *K. pneumoniae* T2MR signal, "IC" indicates Internal Control T2MR signal).

In buffer, the manufacturer's recommended APTATAQ™ concentration of 0.025 units/µL was sufficient for sensitivities, as measured by the $T_2$ signals, that were indistinguishable from those obtained with the mutant HS polymerase (FIG. 5). However, the same concentration was not sufficient for reactions containing crude whole blood lysate (FIG. 5). This was similar to observations made with Taq in crude whole blood lysate (see Example 3) as compared to buffer (Example 1). However, when the APTATAQ™ concentration was raised 5-fold to 0.125 units/µL, amplification was restored, as indicated by the sensitivity of the *K. pneumoniae* signal (FIG. 5). At 10× concentration (0.25 U/µl final), the $T_2$ signals of IC and Kp were indistinguishable from that obtained with the mutant HS polymerase (FIG. 5).

In conclusion, as already observed with Taq polymerase (see Example 3), increasing APTATAQ™ concentrations in lysate not only overcame inhibition by blood components but also countered the impact of high endogenous host DNA concentration on amplification sensitivity and specificity.

Example 6: Importance of Assay Matrix

A workflow for amplifying and detecting DNA (e.g., *Candida* DNA) in whole blood or whole blood lysate is described in Example 3. The sequence of reagent and lysate addition and treatment steps is important for obtaining optimized results.

These steps are as follows:
a. Addition of 30 µl of Reagent A to 50 µl of crude blood lysate
b. Denaturation of the resulting mixture at 95° C. for 5 minutes. This step results in a solid-appearing matrix, which is a mixture of coagulated proteins, membrane fragments, and the like that is present in the blood lysate that appears dark brown.
c. Centrifugation at high speed (>10,000 g) for 5 min. This step results in precipitation of solids into a dark brown pellet and separation of a light-to-dark brown but transparent supernatant.
d. Addition of 20 µl of thermostable DNA polymerase
e. Amplification in the thermocycler
f. Detection of the amplicon.

The sequence of reagent addition and the denaturation step is important for success. Several modifications of the workflow were investigated to evaluate the critical steps/sequence.

Table 4 shows variations of the above workflow that were tested using crude whole blood lysate. FIG. 6 depicts the results as indicated by T2MR signals. The sequence started with addition of 50 µl spiked crude whole blood lysate (as described in Example 2) to PCR tubes. The eight pairs of reaction buffers shown in Table 4 were prepared for addition before or after denaturation at 95° C. Crude whole blood lysate was prepared as described in Example 2. Crude whole blood lysate was spiked to a final concentration of 2 genome copy equivalents of *C. albicans* genomic DNA and 200 copies of Internal Control DNA per reaction. Reagent addition before the denaturation step is to crude whole blood lysate containing spiked target DNA. Samples were then denatured for 5 min at 95° C. and centrifuged for 5 min at 8000 rpm. Reagent addition after the denaturation step was done without disturbing the pellet. Workflow variation #8 is the workflow used in Example 3.

TABLE 4

Workflow variations

| Workflow Variation | Addition before Denaturation at 95° C. | Addition after Denaturation at 95° C. |
|---|---|---|
| 1 | 5.45 µl Water | 44.55 µl dNTPs, Primers, PCR Buffer, Enzyme |
| 2 | 6.25 µl dNTPs | 43.75 µl Primers, PCR Buffer, Enzyme |
| 3 | 9.2 µl Primers | 40.8 µl dNTPs, Reaction Buffer, Enzyme |
| 4 | 25.45 µl PCR Buffer | 24.55 µl dNTPs, Primers, Enzyme |
| 5 | 10 µl dNTPs/Primers | 40 µl PCR Buffer, Enzyme |
| 6 | 26.25 µl dNTPs in PCR Buffer | 23.75 µl Primers, Enzyme |
| 7 | 29.2 µl Primers in PCR Buffer | 20.8 µl dNTPs, Enzyme |
| 8 (Standard Workflow) | 30 µl dNTPs and Primers in PCR Buffer | 20 µl mutant thermostable DNA polymerase |

In general, assays in which the PCR buffer was added prior to the denaturation step (workflow variations 4, 6, 7, and 8) showed good amplification as measured by T2MR signals of *C. albicans* (NT) and Internal Control (IC) (FIG. 6). This includes the workflow #8 as described in Example 3.

The denaturation step, which is considered to inactivate PCR inhibitors such as IgGs and the like, solidifies the previously transparent lysate and transforms it in pseudo-solid matrix. The addition of PCR buffers that contain magnesium chloride, glycerol, and a buffering agent may prevent a trapping of target DNA in the pseudo-solid matrix and subsequent removal during centrifugation. The moderately alkaline pH of the lysate in presence of the PCR buffer (pH of about 8.7 at ambient temperature) is considered to contribute to the additional inactivation of heme compounds. It is known in the art that pH of PCR buffers drops to below pH 7 upon heating due to the intrinsic nature of the buffering compound. This is corroborated by the change in color of the pellet from red to brown after denaturation/centrifugation only when the PCR buffer had been added prior to denaturation. Without wishing to be bound by theory, it is considered that hydroxylizing or reducing the heme may result in heme inactivation and/or removal during the denaturation/centrifugation step, thereby reducing or preventing PCR inhibition. A mechanism involving pH-based reduction or removal of inhibitory substances from blood lysate during denaturation/centrifugation is further supported by the observation of relatively poor amplification performance (as assessed by T2MR signal) when alternate PCR reaction buffers were substituted for the reaction buffer described above. No amplification was seen when the manufacturer's Taq reaction buffer, which has pH 8.0, is used with Taq polymerase in crude whole blood lysate.

Example 7: Use of Taq DNA Polymerase in Reactions Containing Unprocessed Whole Blood Previous reports indicated that Taq polymerase can sometimes be inhibited when more than 1% of whole (unprocessed) blood is added to a PCR reaction (Panaccio et al. *Nucl. Acids Res.* 19(5):1151, 1991). In contrast, the mutant thermostable DNA polymerase tolerates up to 30% whole blood per reaction. While the blood processing methods described above results in a reduction of inhibitors and the ability to amplify target nucleic acids in the presence of crude whole blood lysate, we also tested whether inhibitors can be outcompeted by increased thermostable DNA polymerase concentrations and denatured by alkaline pH buffers (see Example 6) by testing a series of whole blood additions to reaction mixes.

The PCR components (PCR buffer pH 8.7, dNTPs, primers, and enzyme) were mixed before addition of blood. Whole (unprocessed) blood was spiked in a manner such that 5 genome copies of *C. albicans* DNA were added to each sample regardless of blood addition percentage. The whole blood was carefully added to each tube and allowed to sink below the PCR components without mixing. Concentrations of whole unprocessed blood in 100 μl reactions were 10%, 20%, 30%, and 40%, respectively. The performance of the mutant thermostable DNA polymerase, as determined by T2MR signals, was compared to Taq at the manufacturer-recommended concentration (0.025 units/μL) and at 5× the recommended concentration (0.125 units/μL).

Figure 7:
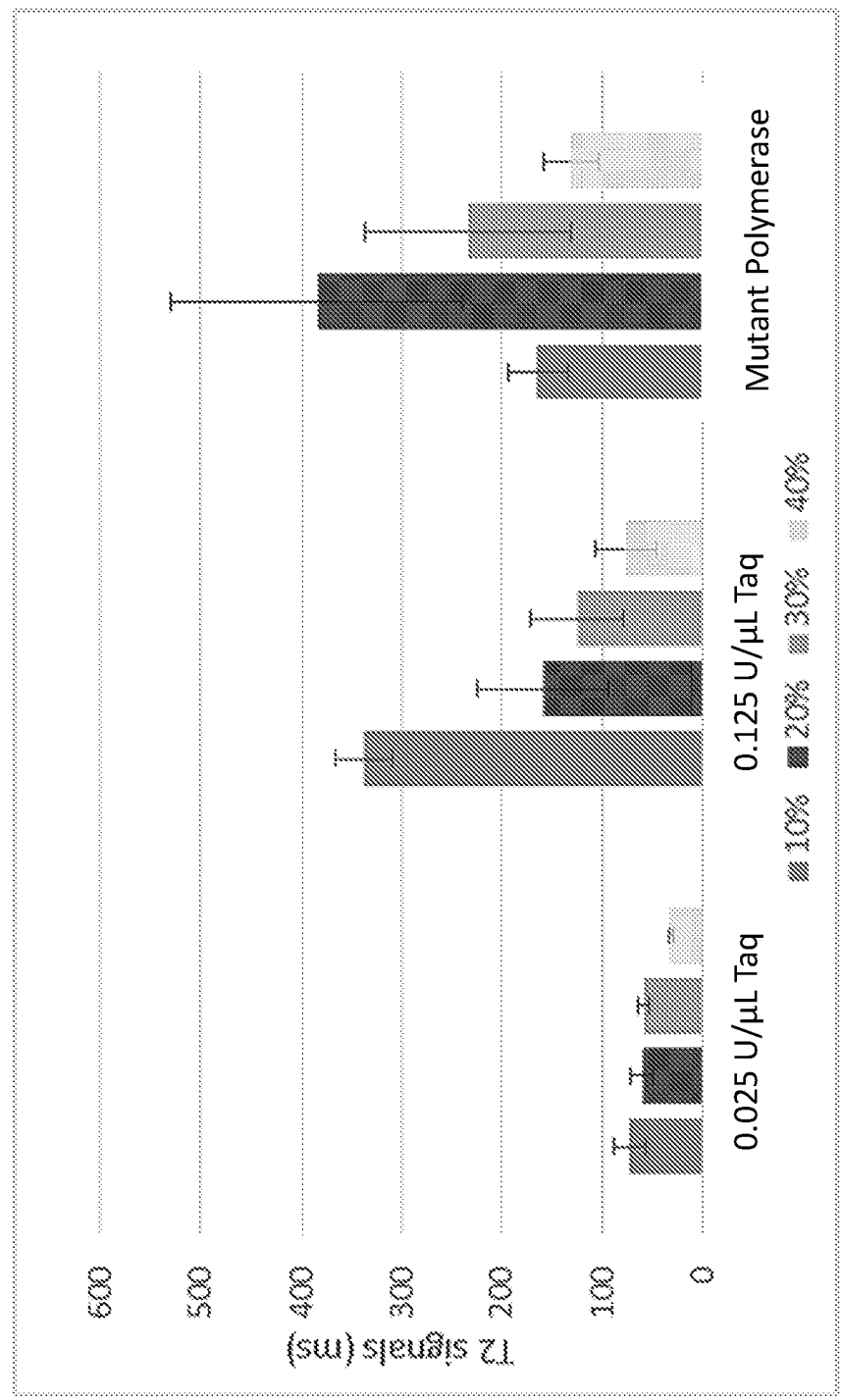
FIG. 7 is a graph showing the results of experiments in which whole blood was added to PCR reactions containing a mutant thermostable DNA polymerase (1× concentration) or Taq polymerase (final: 0.025 or 0.125 U/µl) (n=4, *C. albicans* T2MR signals). Note that the apparent reduction of the T2MR signal obtained from the reaction containing the mutant polymerase and 10% whole blood is considered to be due to an oversaturation of product, thereby suppressing the T2MR signal (hook effect).

At the manufacturer-recommended concentration, Taq performed poorly at all blood additions tested (FIG. 7). Increased amplification, as indicated by higher T2MR signals, was achieved by raising the concentration of Taq to 5× of that recommended by the manufacturer (FIG. 7). However, Taq was inhibited at higher blood concentrations. The upper tolerance limit as seen by T2 values above baseline appeared to be 30% whole blood for 0.125 U/μL Taq and 40% whole blood for the mutant thermostable DNA polymerase (FIG. 7).

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method for amplifying a target nucleic acid characteristic of a pathogen in a whole blood sample obtained from a subject, wherein the whole blood sample comprises subject-derived cells or cell debris, the method comprising:
   (a) lysing the cells in the whole blood sample to form a lysate;
   (b) adding to the lysate a buffer solution comprising a buffering agent to form a reaction mixture, wherein the buffer solution has a moderately alkaline pH of 8.5 to 9.5 at ambient temperature;
   (c) following step (b), heating the reaction mixture to form a denatured reaction mixture and centrifuging the denatured reaction mixture prior to step (d);
   (d) adding a thermostable nucleic acid polymerase to the denatured reaction mixture, wherein the final concentration of the thermostable nucleic acid polymerase is at least 0.02 units per microliter of the denatured reaction mixture, or at least $2.4 \times 10^{-5}$ micrograms of a thermostable nucleic acid polymerase per microliter of denatured reaction mixture; and
   (e) amplifying the target nucleic acid characteristic of a pathogen to form an amplified solution comprising an amplicon, wherein the amplifying is performed by polymerase chain reaction (PCR),
   wherein the whole blood sample is about 0.2 mL to about 5 mL.

2. The method of claim 1, wherein:
   (i) step (c) further comprises centrifuging the denatured reaction mixture prior to step (d);
   (ii) the method comprises adding deoxynucleotide triphosphates (dNTPs), magnesium, a forward primer, and/or a reverse primer during step (b) or during step (d).

3. The method of claim 1, wherein:
   (i) the final concentration of the thermostable nucleic acid polymerase ranges from about 0.02 to about 0.8 units/μL; and/or
   (ii) the final concentration of thermostable nucleic acid polymerase is from about $2.4 \times 10^{-5}$ micrograms to about 0.01 micrograms per microliter of denatured reaction mixture or reaction mixture.

4. The method of claim 1, wherein:
   (i) the thermostable nucleic acid polymerase is a thermostable DNA polymerase;
   (ii) the thermostable nucleic acid polymerase is inhibited by the presence of subject-derived cells or cell debris under normal reaction conditions;
   (iii) the method further comprises amplifying one or more additional target nucleic acids in a multiplexed PCR reaction to generate one or more additional amplicons;
   (iv) an amplicon is produced in the presence of at least 10 μg of subject DNA;
   (v) the method results in the production of at least $10^6$ copies of the amplicon; and/or
   (vi) the method further comprises detecting the amplicon or the one or more additional amplicons.

5. The method of claim 4, wherein the thermostable DNA polymerase is a wild-type thermostable DNA polymerase or a mutant thermostable DNA polymerase.

6. The method of claim 5, wherein:
   (i) the wild-type thermostable DNA polymerase is *Thermus aquaticus* (Taq) DNA polymerase, *Thermus thermophilus* (Tth) DNA polymerase, *Thermus filiformis* (Tfi) DNA polymerase, *Thermus flavus* (Tfl) DNA polymerase, *Thermatoga maritima* (Tma) DNA polymerase, *Thermus* spp. Z05 DNA polymerase, or an archael polymerase;
   or
   (ii) the mutant thermostable DNA polymerase is a hot start thermostable DNA polymerase.

7. The method of claim 4, wherein:
   (i) the amplicon or the one or more additional amplicons is detected by optical, fluorescent, mass, density, magnetic, chromatographic, and/or electrochemical measurement; and/or
   (ii) the method is capable of detecting $10^9$ copies of the amplicon.

8. The method of claim 1, wherein detecting the amplicon comprises the following steps:
   (a') preparing an assay sample by adding to a portion of the amplified solution from $1 \times 10^6$ to $1 \times 10^{13}$ magnetic particles per milliliter of the amplified solution, wherein the magnetic particles have a mean diameter of from 700 nm to 950 nm and binding moieties on their surface, the binding moieties operative to alter aggregation of the magnetic particles in the presence of the amplicon, wherein said magnetic particles have a $T_2$ relaxivity per particle of from $1\times10^9$ to $1\times10^{12}$ mM$^{-1}$s$^{-1}$;

(b') providing the assay sample in a detection tube within a device, the device comprising a support defining a well for holding the detection tube comprising the assay sample, and having an RF coil configured to detect a signal produced by exposing the mixture to a bias magnetic field created using one or more magnets and an RF pulse sequence;

(c') exposing the assay sample to a bias magnetic field and an RF pulse sequence;

(d') following step (c'), measuring the signal produced by the assay sample, thereby detecting the presence or absence of the amplicon.

9. The method of claim 8, wherein:
(i) the magnetic particles comprise a first population of magnetic particles conjugated to a first probe, and a second population of magnetic particles conjugated to a second probe, the first probe operative to bind to a first segment of the amplicon and the second probe operative to bind to a second segment of the amplicon, wherein the magnetic particles form aggregates in the presence of the amplicon; and/or
(ii) the detection occurs within 4 hours from the start of step (a).

10. The method of claim 1, wherein the pathogen is a fungal pathogen, a bacterial pathogen, a protozoan pathogen, or a viral pathogen.

11. The method of claim 10, wherein:
(i) the fungal pathogen is a *Candida* spp.;
(ii) the bacterial pathogen is selected from the group consisting of *Acinetobacter baumannii, Escherichia coli, Enterococcus faecalis, Enterococcus faecium, Klebsiella pneumoniae, Pseudomonas aeruginosa, Staphylococcus aureus, Borrelia burgdorferi, Borrelia afzelii, Borrelia garinii, Rickettsia rickettsii, Anaplasma phagocytophilum, Coxiella burnetii, Ehrlichia chaffeensis, Ehrlichia ewingii, Francisella tularensis, Streptococcus pneumoniae*, and *Neisseria meningitides*; or
(iii) the protozoan pathogen is *Babesia microti* or *Babesia divergens*.

12. The method of claim 11, wherein the *Candida* spp. is selected from the group consisting of *Candida albicans, Candida guilliermondii, Candida glabrata, Candida krusei, Candida lusitaniae, Candida parapsilosis*, and *Candida tropicalis*.

13. The method of claim 1, wherein:
(i) the method is capable of detecting a concentration of about 10 colony-forming units (CFU)/mL of the pathogen species in the whole blood sample; and/or
(ii) the method further comprises diagnosing the subject based on the detection of the amplicon, wherein the presence of the amplicon indicates that the subject is suffering from a disease associated with the pathogen and/or administering to the subject a suitable therapy.

14. A method for amplifying a target nucleic acid characteristic of a pathogen in a whole blood sample, the method comprising:
(a) providing a crude blood lysate produced by lysing the red blood cells in a whole blood sample from a subject, centrifuging the sample to form a supernatant and a pellet comprising cells, discarding some or all of the supernatant, optionally washing the pellet, and lysing the cells in the pellet;
(b) adding to the crude blood lysate a buffer solution comprising a buffering agent to form a reaction mixture, wherein the buffer solution has a moderately alkaline pH of 8.5 to 9.5 at ambient temperature;
(c) following step (b), heating the reaction mixture to form a denatured reaction mixture and centrifuging the denatured reaction mixture prior to step (d);
(d) adding a thermostable nucleic acid polymerase to the denatured reaction mixture, wherein the final concentration of the thermostable nucleic acid polymerase is at least 0.02 units per microliter of the denatured reaction mixture, or at least $2.4\times10^{-5}$ micrograms of a thermostable nucleic acid polymerase per microliter of denatured reaction mixture; and
(e) amplifying the target nucleic acid characteristic of a pathogen to form an amplified solution comprising an amplicon, wherein the amplifying is performed by PCR),
wherein (i) the whole blood sample is about 0.2 mL to about 5 mL; (ii) the crude blood lysate produced from the whole blood sample has a volume of about 10 µL to about 500 µL; and (iii) the reaction mixture of step (b) contains about 1% to about 70% crude blood lysate.

\* \* \* \* \*